US009916420B2

(12) United States Patent
Cardoza et al.

(10) Patent No.: US 9,916,420 B2
(45) **Date of Patent: *Mar. 13, 2018**

(54) PHYSICIAN AND CLINICAL DOCUMENTATION SPECIALIST WORKFLOW INTEGRATION

(71) Applicant: Nuance Communications, Inc., Burlington, MA (US)

(72) Inventors: Timothy Cardoza, Hollis, NH (US); James R. Flanagan, Iowa City, IA (US); Brian P. Boyer, Smyrna, GA (US)

(73) Assignee: Nuance Communications, Inc., Burlington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/921,038

(22) Filed: Jun. 18, 2013

(65) Prior Publication Data

US 2013/0297348 A1 Nov. 7, 2013

Related U.S. Application Data

(63) Continuation-in-part of application No. 13/030,959, filed on Feb. 18, 2011, now Pat. No. 8,768,723.

(51) Int. Cl.
*G06Q 50/22* (2012.01)
*G06Q 50/24* (2012.01)
(Continued)

(52) U.S. Cl.
CPC ............ *G06F 19/322* (2013.01); *G06F 19/32* (2013.01); *G10L 15/1822* (2013.01); *G10L 15/26* (2013.01); *G10L 2015/221* (2013.01)

(58) Field of Classification Search
CPC ........ G06Q 50/22; G06Q 50/24; G06Q 10/10; G06Q 10/00; G06K 9/62; H04N 21/466;
(Continued)

(56) References Cited

U.S. PATENT DOCUMENTS 4,477,698 A 10/1984 Szlam et al.
4,965,763 A 10/1990 Zamora
(Continued)

FOREIGN PATENT DOCUMENTS

WO WO 2010/117424 A2 10/2010

OTHER PUBLICATIONS

Meta Health Technology, Feb. 4, 2010 "Jump Start Your Clinical Documentation Improvement Program with META's eCDI Application" http://streamlinehealth.net/assets/pdftsMeta.JumpStartYourCDIProcess.pdf.*
(Continued)

*Primary Examiner* — Maroun Kanaan
(74) *Attorney, Agent, or Firm* — Wolf, Greenfield & Sacks, P.C.

(57) ABSTRACT

A medical documentation system and a CDI system may be linked together, or integrated, so there is a tie between the two systems that allows for a much more efficient and effective CDI process. In one disclosed embodiment, a CDI system receives from a medical documentation system a structured data set including at least some information relating to one or more medical facts the medical documentation system automatically extracted from text documenting a patient encounter.

17 Claims, 20 Drawing Sheets

(51) Int. Cl.

| | |
|---|---|
| *G06K 9/62* | (2006.01) |
| *G06F 19/00* | (2018.01) |
| *G10L 15/26* | (2006.01) |
| *G10L 15/18* | (2013.01) |
| *G10L 15/22* | (2006.01) |

(58) Field of Classification Search

CPC ........ G06N 5/025; G06N 7/06; G06N 99/005; G06F 19/322; G06F 19/345; G06F 17/21; G06F 19/3487; G06F 17/2229; G06F 17/271; G06F 17/273; G06F 17/274; G06F 17/275; G06F 17/278; G06F 17/30516; G06F 19/328; G06F 17/27; G06F 19/18; G06F 19/28; G06F 19/3443; G06F 17/30011; G06F 17/30598; G06F 17/20; G06F 17/241; G06F 17/2785; G10L 15/26; G10L 2015/228; G10L 15/1822

USPC .......................................................... 705/2, 3

See application file for complete search history.

(56) References Cited

U.S. PATENT DOCUMENTS

| | | | | |
|---|---|---|---|---|
| 5,146,439 | A | 9/1992 | Jachmann et al. | |
| 5,253,164 | A | 10/1993 | Holloway et al. | |
| 5,325,293 | A | 6/1994 | Dorne | |
| 5,327,341 | A | 7/1994 | Whalen et al. | |
| 5,392,209 | A | 2/1995 | Eason et al. | |
| 5,519,808 | A | 5/1996 | Benton, Jr. et al. | |
| 5,544,360 | A | 8/1996 | Lewak et al. | |
| 5,602,982 | A | 2/1997 | Judd et al. | |
| 5,664,109 | A | 9/1997 | Johnson et al. | |
| 5,675,788 | A | 10/1997 | Husick et al. | |
| 5,748,888 | A | 5/1998 | Angelo et al. | |
| 5,799,268 | A | 8/1998 | Boguraev | |
| 5,809,476 | A | 9/1998 | Ryan | |
| 5,812,882 | A | 9/1998 | Raji et al. | |
| 5,832,450 | A | 11/1998 | Myers et al. | |
| 5,857,212 | A | 1/1999 | Van De Vanter | |
| 5,875,448 | A | 1/1999 | Boys et al. | |
| 5,893,109 | A | 4/1999 | DeRose et al. | |
| 5,970,463 | A | 10/1999 | Cave et al. | |
| 5,974,412 | A | 10/1999 | Hazlehurst et al. | |
| 6,006,221 | A | 12/1999 | Liddy et al. | |
| 6,014,663 | A | 1/2000 | Rivette et al. | |
| 6,021,202 | A | 2/2000 | Anderson et al. | |
| 6,052,693 | A | 4/2000 | Smith et al. | |
| 6,055,494 | A | 4/2000 | Friedman | |
| 6,088,437 | A | 7/2000 | Amick | |
| 6,182,029 | B1 | 1/2001 | Friedman | |
| 6,192,112 | B1 | 2/2001 | Rapaport et al. | |
| 6,289,353 | B1 | 9/2001 | Hazlehurst et al. | |
| 6,292,771 | B1 | 9/2001 | Haug et al. | |
| 6,347,329 | B1 | 2/2002 | Evans | |
| 6,360,215 | B1 | 3/2002 | Judd et al. | |
| 6,374,225 | B1 | 4/2002 | Hejna, Jr. | |
| 6,405,165 | B1 | 6/2002 | Blum et al. | |
| 6,415,256 | B1 | 7/2002 | Ditzik | |
| 6,434,547 | B1 | 8/2002 | Mishelevich et al. | |
| 6,438,533 | B1 | 8/2002 | Spackman et al. | |
| 6,438,545 | B1 | 8/2002 | Beauregard et al. | |
| 6,553,385 | B2 | 4/2003 | Johnson et al. | |
| 6,854,086 | B2 | 2/2005 | Umen et al. | |
| 6,865,258 | B1 | 3/2005 | Polcyn | |
| 6,915,254 | B1 | 7/2005 | Heinze et al. | |
| 6,925,436 | B1 | 8/2005 | Franz et al. | |
| 6,947,936 | B1 | 9/2005 | Suermondt et al. | |
| 6,950,994 | B2 | 9/2005 | Dharap | |
| 6,961,699 | B1 | 11/2005 | Kahn et al. | |
| 6,996,445 | B1 | 2/2006 | Kamijo | |
| 7,016,844 | B2 | 3/2006 | Othmer et al. | |
| 7,124,144 | B2 | 10/2006 | Christianson et al. | |
| 7,233,938 | B2 | 6/2007 | Carus et al. | |
| 7,236,932 | B1 | 6/2007 | Grajski | |
| 7,299,110 | B2 | 11/2007 | Gupta et al. | |
| 7,379,946 | B2 | 5/2008 | Carus et al. | |
| 7,493,253 | B1 | 2/2009 | Ceusters et al. | |
| 7,610,192 | B1 | 10/2009 | Jamieson | |
| 2002/0007285 | A1 | 1/2002 | Rappaport | |
| 2002/0095313 | A1 | 7/2002 | Haq | |
| 2002/0128861 | A1 | 9/2002 | Lau et al. | |
| 2002/0143824 | A1 | 10/2002 | Lee et al. | |
| 2002/0169764 | A1 | 11/2002 | Kincaid et al. | |
| 2003/0046080 | A1 | 3/2003 | Hejna, Jr. | |
| 2003/0046264 | A1 | 3/2003 | Kauffman | |
| 2003/0061201 | A1 | 3/2003 | Grefenstette et al. | |
| 2003/0067495 | A1 | 4/2003 | Pu et al. | |
| 2003/0079186 | A1 | 4/2003 | Gondo et al. | |
| 2003/0115080 | A1 | 6/2003 | Kasravi et al. | |
| 2003/0208382 | A1 | 11/2003 | Westfall | |
| 2003/0233345 | A1 | 12/2003 | Perisic et al. | |
| 2004/0103075 | A1 | 5/2004 | Kim et al. | |
| 2004/0139400 | A1 | 7/2004 | Allam et al. | |
| 2004/0186746 | A1 | 9/2004 | Angst et al. | |
| 2004/0186747 | A1 | 9/2004 | Nakano et al. | |
| 2004/0205638 | A1 | 10/2004 | Thomas et al. | |
| 2004/0220895 | A1 | 11/2004 | Carus et al. | |
| 2004/0243545 | A1 | 12/2004 | Boone et al. | |
| 2004/0243551 | A1 | 12/2004 | Boone et al. | |
| 2004/0243552 | A1 | 12/2004 | Titemore et al. | |
| 2004/0243614 | A1 | 12/2004 | Boone et al. | |
| 2005/0108010 | A1 | 5/2005 | Frankel et al. | |
| 2005/0114122 | A1 | 5/2005 | Uhrbach et al. | |
| 2005/0120020 | A1 | 6/2005 | Carus et al. | |
| 2005/0120300 | A1 | 6/2005 | Schwager et al. | |
| 2005/0137910 | A1* | 6/2005 | Rao et al. | 705/3 |
| 2005/0144184 | A1 | 6/2005 | Carus et al. | |
| 2005/0149747 | A1 | 7/2005 | Wesinger, Jr. et al. | |
| 2006/0206943 | A1 | 9/2006 | Ellison et al. | |
| 2006/0253895 | A1 | 11/2006 | Brandofino et al. | |
| 2006/0272025 | A1 | 11/2006 | Mononen | |
| 2007/0143857 | A1 | 6/2007 | Ansari | |
| 2007/0283444 | A1 | 12/2007 | Jang | |
| 2007/0294745 | A1 | 12/2007 | Tan et al. | |
| 2007/0300287 | A1 | 12/2007 | Wynne et al. | |
| 2009/0192822 | A1 | 7/2009 | Regulapati et al. | |
| 2009/0192954 | A1* | 7/2009 | Katukuri et al. | 706/11 |
| 2010/0094657 | A1 | 4/2010 | Stern et al. | |
| 2010/0114597 | A1 | 5/2010 | Shreiber et al. | |
| 2010/0250236 | A1 | 9/2010 | Jagannathan et al. | |
| 2012/0212337 | A1 | 8/2012 | Montyne et al. | |
| 2012/0215558 | A1 | 8/2012 | Flanagan et al. | |
| 2012/0323598 | A1 | 12/2012 | Koll et al. | |
| 2013/0041685 | A1 | 2/2013 | Yegnanarayanan | |
| 2013/0297347 | A1 | 11/2013 | Cardoza et al. | |

OTHER PUBLICATIONS

U.S. Appl. No. 10/413,405, filed Apr. 15, 2003, Carus.
U.S. Appl. No. 10/447,290, filed May 2, 2003, Boone.
U.S. Appl. No. 10/448,317, filed May 30, 2003, Boone.
U.S. Appl. No. 10/448,320, filed May 30, 2003, Boone.
U.S. Appl. No. 10/448,325, filed May 30, 2003, Titemore.
U.S. Appl. No. 10/787,889, filed Feb. 27, 2004, Carus.
U.S. Appl. No. 10/840,428, filed Oct. 13, 2005, Carus et al.
U.S. Appl. No. 10/948,625, filed Sep. 23, 2004, Schwager.
U.S. Appl. No. 10/951,281, filed Sep. 22, 2005, Cote et al.
U.S. Appl. No. 10/951,291, filed Sep. 27, 2004, Uhrbach.
U.S. Appl. No. 10/953,448, filed Sep. 30, 2004, Carus.
U.S. Appl. No. 10/953,471, filed Jul. 28, 2005, Cote et al.
U.S. Appl. No. 10/953,474, filed Sep. 29, 2004, Frankel.
U.S. Appl. No. 11/007,626, filed Jul. 28, 2005, Cote et al.
U.S. Appl. No. 11/068,493, filed Sep. 1, 2005, Carus et al.
U.S. Appl. No. 11/069,203, filed Sep. 1, 2005, Cote et al.
International Search Report dated Mar. 9, 2005 for PCT Application Serial No. PCT/US2004/016878, International Filing Date May 28, 2004.
[No Author Listed] Customizing D/41 Call Analysis:, date unknown, Intel Corp., Santa Clara, California, available at http //

(56) References Cited

OTHER PUBLICATIONS resource intel com/telecom/support/appnotes/custd41d htm, (last accessed Jul. 25, 2005).
[No Author Listed] Case Study: Massachusetts Medical Society http://www.microsoft.com/resources/casestudies/CaseStudy.asp?CaseStudyID=14931 posted Jan. 13, 2004.
[No Author Listed] Category III CPT Codes, American Medical Association, http // www ama-assn org/ama/pub/article/3885-4897 html, printed Mar. 22, 2004.
[No Author Listed] Code Information and Education web page, American Medical Association, http://www.ama-assn.org/ama/pub/category/3884.html printed Mar. 22, 2004.
[No Author Listed] Continuity of Care Record (CCR), AADP Center for Health Information Technology, http // www centerforhit or /x201 xml, posted Aug. 20, 2004.
[No Author Listed] Continuity of Care Record (CCR): The Concept Paper of the CCR, v. 2. 1b, http://www.bhtinfo.com/CCR.Concept%20Paper.1.5.doc.
[No Author Listed] Continuity of Care Record, American Academy of Family Physicians, http://www.aafp.org/x24962.xml?printxml posted Nov. 12, 2003.
[No Author Listed] Core Measures web page, Joint Commission on Accreditation of Healthcare Organizations, http://www.jcaho.org/pms/core+measures/ printed Mar. 22, 2004.
[No Author Listed] Epic Web Training Manual, pp. 1-33, 2002.
[No Author Listed] Hardware Reference Manual, Release 3 for DOS, revised Jan. 1994, PIKA Technologies, Inc., Ontario, Canada, available at http://www.pikatechnologies.com/downloads/legacy/AVA%20B-Series%20Hardware%20Manual.pdf (last accessed Jul. 25, 2005).
[No Author Listed] http://www.comp.lancs.ac.uk/computing/research/stemming/general/index.htm printed Jul. 19, 2004.
[No Author Listed] http://www.comp.lancs.ac.uk/computing/research/stemming/general/performance.htm printed Jul. 19, 2004.
[No Author Listed] http://www.comp.lancs.ac.uk/computing/research/stemming/general/stemmingerrors.htm printed Jul. 19, 2004.
[No Author Listed] ICD-9-CM Official Guidelines for Coding and Reporting, effective Oct. 1, 2003.
[No Author Listed] ICD-9-CM Preface (FY04), http://ftp.cdc.gov/pub/Health_Statistics/NCHS/Publications/ICD9-CM/2004/Prefac05.RTF.
[No Author Listed] M*MODAL, Two-Minute Guide to M*Modal, 1 page.
[No Author Listed] Press Release: Kryptiq Announces Support of CCR Initiative and Introduces New Solutions that Enable Information Portability, Accessibility and Clinical System Interoperability, http://www.kryptiq.com/News/PressReleases/27.html posted Feb. 17, 2004.
[No Author Listed] Specifications Manual for National Implementation of Hospital Core Measures, v. 2.0, *Joint Commission on Accreditation of Healthcare Organizations*, http://www.jcaho.org/pms/core+measures/information+on+final+specifications.htm.
[No Author Listed] Work Item Summary: WK4363 Standard Specification for the Continuity of Care Record (CCR), http // www astm org/cqi-bin/SoftCart exe/DATABASE.CART/WORKITEMS/WK4363htm?+mystore, Mar. 3, 2004.
Batty et al., "The development of a portable real-time display of voice source characteristics", IEEE, 2:419-422 (2000).
Braithwaite, Continuity of Care Record (CCR) http://www.h17.org/library/himss/2004Orlando/Continuityof CareRecord.pdf.
Brill, Some Advances in Transformation-Based Part-of-Speech Tagging, Spoken Language Systems Group.
Cimiano et al., "Learning concept hierarchies from text with a guided hierarchical clustering algorithm," In C. Biemann and G. Paas (eds.), Proceedings of the ICML 2005 Workshop on Learning and Extending Lexical Ontologies with Machine Learning Methods, Bonn, Germany, (2005).
Creutz, "Morphology and Finite-State Transducers", Oct. 31, 2001, Chapter 3, Jurafsky & Martin.
Cutting et al., A Practical Part-of-Speech, Xerox Palo Alto Research Center.
Daelemans, et al., TIMBL: Tiburg Memory Based Learner, Version 5,0, Reference Guide, ILK Research Group Technical Report Series No. 04-02 (ILK-0402), ILK Research Group, Tilbur University, Tilburg, Netherlands, 2004.
Day, Extracting Knowledge from Text Using Learning by Constraint Relaxation (LCR), CSI, www.csi-inc.com/CSI/pdf/jday_icim02.pdf.
Fan et al., "PRISMATIC: Inducing Knowledge from a Large Scale Lexicalized Relation Resource," Proceedings of the NAACL HLT 2010 First International Workshop on Formalisms and Methodology for Learning by Reading, pp. 122-127, Los Angeles, California, Jun. 2010.
Florian et al., "A Statistical Model for Multilingual Entity Detection and Tracking," Proceedings of the Human Language Technologies Conference 2004 (HLT-NAACL'04), (2004).
Gale et al., Discrimination Decisions for 100,000-Dimensional Spaces, *Current Issues in Computational Linguistics*, pp. 429-450, Kluwer Academic Publishers, 1994.
Gomez-Perez et al., "An overview of methods and tools for ontology learning from texts," Knowledge Engineering Review 19:3 p. 187-212, 2004.
Hieb, Research Note, NLP Basics for Healthcare, Aug. 16, 2002.
Lee et al., Cleansing Data for Mining and Warehousing, Lecture Notes in Computer Science vol. 1677 archive, *Proceedings of the 10th International Conference on Database and Expert Systems Applications*, pp. 751-760, Springer-Verlag, London, 1999.
Nevill-Manning et al., "The Development of Holte's 1R Classifier", Department of Computer Science.
Nivre, DAC723: Language Technology Finite State Morphology, Vaxjo University of Mathematics and Systems Engineering, p. 1-11.
Salton et al., "A Vector Space Model for Automatic Indexing," Communications of the ACM, vol. 18, No. 11, Nov. 1975.
Shalizi et al., Pattern Discovery in Time Series, Part I: Theory, Algorithm, Analysis, and Convergence, *Journal of Machine Learning* (2002)—Submitted Oct. 28, 2002;Published 2002.
Smith et al., "MICROARRAS: An Advanced Full-Text Retrieval and Analysis System", ACM 1987, p. 187-195.
Song et al., A Graphical Interface to a Semantic Medical Information System, Karp-95 Proceedings of the Second International Symposium on Knowledge Acquisition, Representation and Processing, pp. 107-109, 1995.
Song et al., A Cognitive Model for the Implementation of Medical Problem Lists, *Proceedings of the First Congress on Computational Medicine,Public Health and Biotechnology*, Austin, Texas, 1994.
Song et al., A Graphical Interface to a Semantic Medical Information System, *Journal of Foundations of Computing and Decision Sciences*, 22(2), 1997.
Van Rijsbergen, Information Retrival, 2nd Ed., Ch. 5, Butterworths, London, 1979.
Wagemann, EHR vs. CCR: What is the Difference Between the Electronic Health Record and the Continuity of Care Record?, Medical Records Institute, 2004.
Welty et al., "Large Scale Relation Detection," Proceedings of the NAACL HLT 2010 First International Workshop on Formalisms and Methodology for Learning by Reading, pp. 24-33, Los Angeles, California, Jun. 2010.
Yang et al., "Faster Algorithm of String Comparison", Pattern Analysis and Applications, vol. 6, No. 1, Apr. 2003, pp. 122-133.
Zavrel et al., Recent Advances in Memory-Based Part-of-Speech Tagging, ILK/Computational Linguistics.
International Search Report and Written Opinion for PCT/US2014/042943 dated Jan. 7, 2015.

* cited by examiner

200

Patient Name [John Doe]  Sex [M]  Creation Date [01-18-2011]
Document Type [Discharge Summary]

Chief complaint: Patient is presenting chest pain and shortness of breath.

Medical history: The patient is hypertensive. He is also obese.

Social history: He smokes one pack per day. Drinks occasionally.

220

⊟Problems(:)
| Name | Status |
Add Fact

⊟Medications(0)
| Name | Status | Schedules |
Add Fact

⊟Allergies(0)
| Name | Type | Status | Substance | Reactions |
Add Fact

⊟Social History (:)
Add Alcohol Fact | Add Tobacco Fact

230

[Process] [Cancel]

240

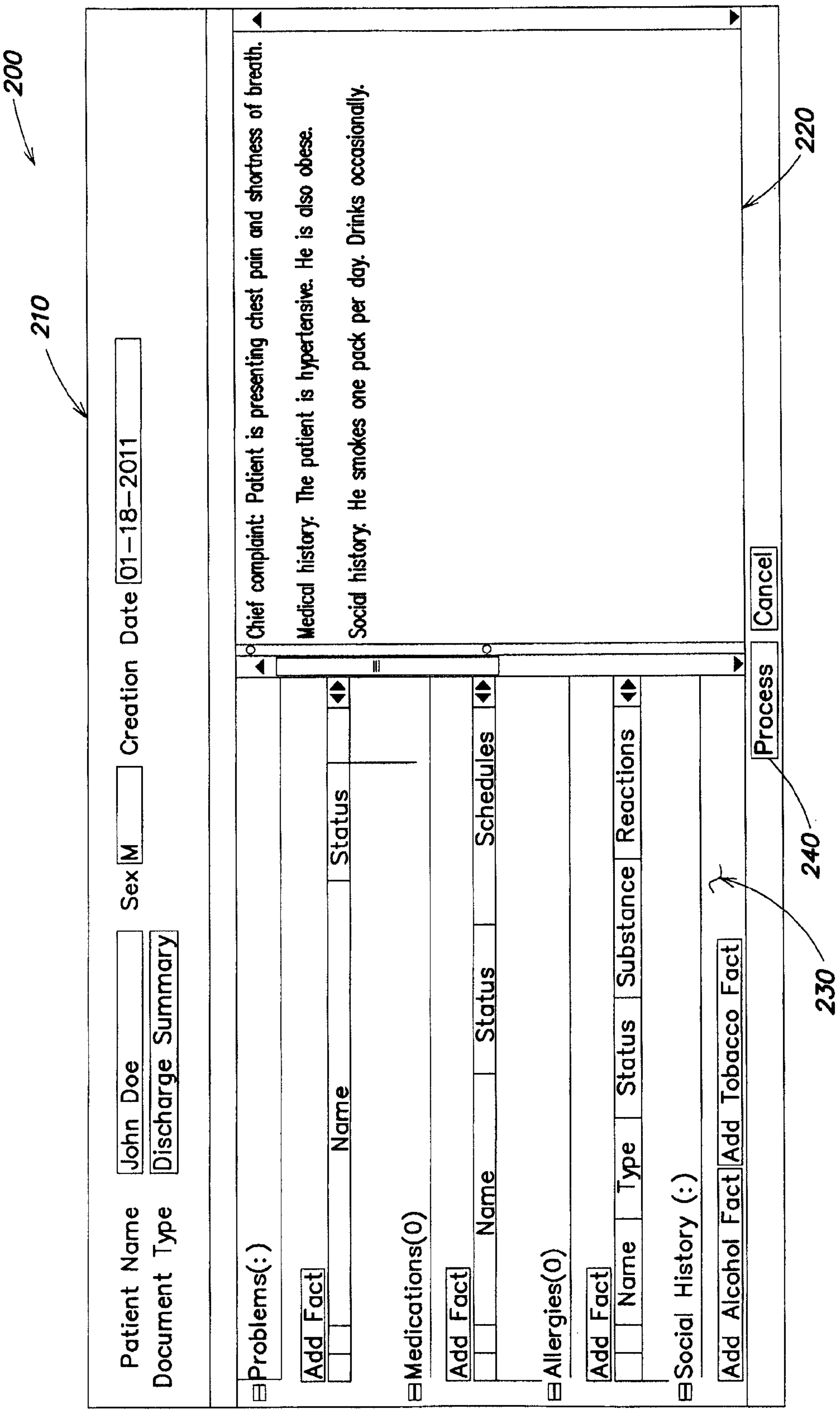

FIG. 2

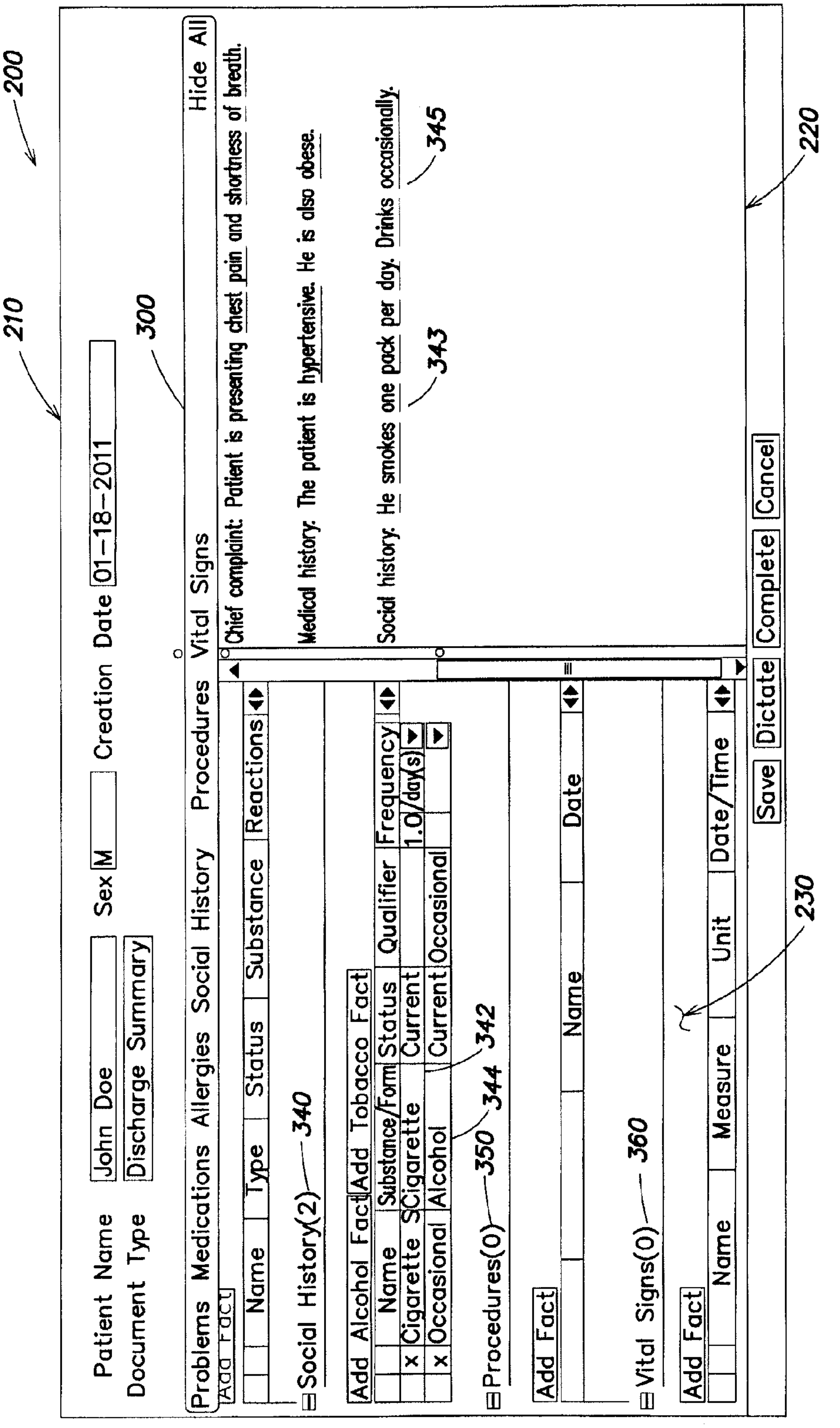

FIG. 3B

Patient Name [John Doe] Sex [M] Creation Date [01-18-2011] — 210
Document Type [Discharge Summary] — 300

Problems | Medications | Allergies | Social History | Substance | Procedures | Vital Signs  Hide All Add Fact
| Name | Type | Status | Substance | Reactions |

⊟ Social History(2) — 340

Add Alcohol Fact | Add Tobacco Fact
| Name | Substance/Form | Status | Qualifier | Frequency |
| x | Cigarette | S Cigarette | Current | | 1.0/day(s) |
| x | Occasional | Alcohol | Current | Occasional | |
                 350   344  342

Chief complaint: Patient is presenting chest pain and shortness of breath.

Medical history: The patient is hypertensive. He is also obese.

Social history: He smokes one pack per day. Drinks occasionally.
                              343                      345

⊟ Procedures(0) — 350

Add Fact
| Name | Date |

⊟ Vital Signs(0) — 360

Add Fact
| Name | Measure | Unit | Date/Time |

[Save] [Dictate] [Complete] [Cancel]
— 230

— 200
— 220

PHYSICIAN AND CLINICAL DOCUMENTATION SPECIALIST WORKFLOW INTEGRATION

CROSS-REFERENCE TO RELATED APPLICATIONS

This application is a continuation-in-part of U.S. patent application Ser. No. 13/030,959, filed Feb. 18, 2011, entitled "Methods and Apparatus for Formatting Text for Clinical Fact Extraction," which is incorporated herein by reference in its entirety.

BACKGROUND

1. Field

The techniques described herein are directed generally to the field of medical documentation, and more particularly to techniques for the creation and use of patient records in medical settings.

2. Description of the Related Art

Medical documentation is an important process in the healthcare industry. Most healthcare institutions maintain a longitudinal medical record (e.g., spanning multiple observations or treatments over time) for each of their patients, documenting, for example, the patient's history, encounters with clinical staff within the institution, treatment received, and/or plans for future treatment. Such documentation facilitates maintaining continuity of care for the patient across multiple encounters with various clinicians over time. In addition, when an institution's medical records for large numbers of patients are considered in the aggregate, the information contained therein can be useful for educating clinicians as to treatment efficacy and best practices, for internal auditing within the institution, for quality assurance, etc.

Historically, each patient's medical record was maintained as a physical paper folder, often referred to as a "medical chart," or "chart." Each patient's chart would include a stack of paper reports, such as intake forms, history and immunization records, laboratory results, and clinicians' notes. Following an encounter with the patient, such as an office visit, a hospital round, or a surgical procedure, the clinician conducting the encounter would provide a narrative note about the encounter to be included in the patient's chart. Such a note could include, for example, a description of the reason(s) for the patient encounter, an account of any vital signs, test results and/or other clinical data collected during the encounter, one or more diagnoses determined by the clinician from the encounter, and a description of a plan for further treatment. Often, the clinician would verbally dictate the note into an audio recording device or a telephone giving access to such a recording device, to spare the clinician the time it would take to prepare the note in written form. Later, a medical transcriptionist would listen to the audio recording and transcribe it into a text document, which would be inserted on a piece of paper into the patient's chart for later reference.

Currently, many healthcare institutions are transitioning or have transitioned from paper documentation to electronic medical record systems, in which patients' longitudinal medical information is stored in a data repository in electronic form. Besides the significant physical space savings afforded by the replacement of paper record-keeping with electronic storage methods, the use of electronic medical records also provides beneficial time savings and other opportunities to clinicians and other healthcare personnel.

For example, when updating a patient's electronic medical record to reflect a current patient encounter, a clinician need only document the new information obtained from the encounter, and need not spend time entering unchanged information such as the patient's age, gender, medical history, etc. Electronic medical records can also be shared, accessed, and updated by multiple different personnel from local and remote locations through suitable user interfaces and network connections, eliminating the need to retrieve and deliver paper files from a crowded file room.

Most hospitals today have a Clinical Documentation Improvement (CDI) process in place to ensure they have complete and accurate clinical documentation. This process is a manual process involving a trained Clinical Documentation Specialist (CDS). A CDS, also sometimes referred to as a CDI specialist, is a professional trained in reviewing clinical documentation (such as physician's notes) for completeness to ensure the proper detail exists so that the correct supporting information is included to support a given diagnosis or that the proper diagnosis is reflected in the documentation. This aids with more accurate documentation to reflect the patient diagnosis and ultimately helps feed into the process to ensure the hospital is appropriately billing and being reimbursed for the appropriate diagnosis.

When, as a result of his or her manual review of clinical documentation, a CDS identifies areas where the documentation may not provide the required information, the CDI process will involve the CDS following up manually with the clinician to get the required information. Such a follow up process requires a manual action of some sort by the CDS (such as an email, a message to the clinician's inbox, or even sometimes a sticky note in the patient chart) to get the required information.

Specialized software tools have been developed that can be installed at the customer site (e.g., a hospital or clinic) to allow the CDS to review clinical documentation for completeness. The CDS will use such a tool to review the various to factors reflected in the clinical documentation and ensure that the proper diagnosis based on the known information can be made. If the information does not exist, the CDS will manually use the tool to generate a clarification request to the clinician to get the required information to ensure the documentation reflects the diagnosis as accurately as possible. An example of such a specialized software tool for use by a CDS is the Compliant Document Management Program Guide (CDMP Guide) product offered by J. A. Thomas & Associates (JATA), a wholly owned subsidiary of Nuance Communications, Inc. ("Nuance"), of Burlington, Mass.

SUMMARY

One embodiment is direct to a method comprising an act of: with a CDI system, receiving from a medical documentation system a structured data set including at least some information relating to one or more medical facts the medical documentation system automatically extracted from text documenting a patient encounter.

Another embodiment is directed to a CDI system comprising at least one processor configured to allow the CDI system to receive from a medical documentation system a structured data set including at least some information relating to one or more medical facts the medical documentation system automatically extracted from text documenting a patient encounter Another embodiment is directed to a non-transitory, computer-readable medium having a plurality of instructions encoded thereon which, when executed by at least one processor, cause the at least one processor to allow a CDI system to receive from a medical documentation system a structured data set including at least some information relating to one or more medical facts the medical documentation system automatically extracted from text documenting a patient encounter.

Another embodiment is directed to a method comprising an act of: with a medical documentation system, transmitting to a CDI system a structured data set including at least some information relating to one or more medical facts the medical documentation system automatically extracted from text documenting a patient encounter.

Another embodiment is directed to a medical documentation system comprising at least one processor configured to cause the medical documentation system to transmit to a CDI system a structured data set including at least some information relating to one or more medical facts the medical documentation system automatically extracted from text documenting a patient encounter.

Another embodiment is directed to a non-transitory, computer-readable medium having a plurality of instructions encoded thereon which, when executed by at least one processor, cause the at least one processor to cause a medical documentation system to transmit to a CDI system a structured data set including at least some information relating to one or more medical facts the medical documentation system automatically extracted from text documenting a patient encounter.

Another embodiment is directed to a method comprising: identifying, using at least one statistical fact extraction model applied by at least one processor, a plurality of alternative hypotheses for a medical fact to be extracted from a portion of text documenting a patient encounter; selecting at least two of the alternative hypotheses; and presenting the selected hypotheses to a user documenting the patient encounter.

Another embodiment is directed to apparatus comprising at least one processor, and at least one memory storing processor-executable instructions that, when executed by the at least one processor, perform a method comprising: identifying, using at least one statistical fact extraction model, a plurality of alternative hypotheses for a medical fact to be extracted from a portion of text documenting a patient encounter; selecting at least two of the alternative hypotheses; and presenting the selected hypotheses to a user documenting the patient encounter.

Another embodiment is directed to at least one computer-readable storage medium encoded with computer-executable instructions that, when executed, perform a method comprising: identifying, using at least one statistical fact extraction model a plurality of alternative hypotheses for a medical fact to be extracted from a portion of text documenting a patient encounter; selecting at least two of the alternative hypotheses; and presenting the selected hypotheses to a user documenting the patient encounter.

Another embodiment is directed to a method comprising: extracting, using at least one processor, a first set of one or more medical facts from a first portion of a text documenting a patient encounter; receiving, from a user, a correction to the first set of medical facts, wherein the correction identifies a fact that should be associated with the first portion of the text; and extracting a second set of one or more medical facts from a second portion of the text based at least in part on the user's correction to the first set of medical facts, wherein extracting the second set of facts comprises extracting one or more facts similar to the identified fact from the second portion of the text.

Another embodiment is directed to apparatus comprising at least one processor, and at least one memory storing processor-executable instructions that, when executed by the at least one processor, perform a method comprising: extracting a first set of one or more medical facts from a first portion of a text documenting a patient encounter; receiving, from a user, a correction to the first set of medical facts, wherein the correction identifies a fact that should be associated with the first portion of the text; and extracting a second set of one or more medical facts from a second portion of the text based at least in part on the user's correction to the first set of medical facts, wherein extracting the second set of facts comprises extracting one or more facts similar to the identified fact from the second portion of the text.

Another embodiment is directed to at least one computer-readable storage medium encoded with computer-executable instructions that, when executed, perform a method comprising: extracting a first set of one or more medical facts from a first portion of a text documenting a patient encounter; receiving, from a user, a correction to the first set of medical facts, wherein the correction identifies a fact that should be associated with the first portion of the text; and extracting a second set of one or more medical facts from a second portion of the text based at least in part on the user's correction to the first set of medical facts, wherein extracting the second set of facts comprises extracting one or more facts similar to the identified fact from the second portion of the text.

Another embodiment is directed to a method comprising: receiving an original text that is a representation of a narration of a patient encounter provided by a clinician; re-formatting the original text, using at least one processor, to produce a formatted text; extracting one or more clinical facts from the formatted text, wherein a first fact of the one or more clinical facts is extracted from a first portion of the formatted text, wherein the first portion of the formatted text is a formatted version of a first portion of the original text; and maintaining a linkage between the first fact and the first portion of the original text.

Another embodiment is directed to apparatus comprising at least one processor, and a memory storing processor-executable instructions that, when executed by the at least one processor, perform a method comprising: receiving an original text that is a representation of a narration of a patient encounter provided by a clinician; re-formatting the original text to produce a formatted text; extracting one or more clinical facts from the formatted text, wherein a first fact of the one or more clinical facts is extracted from a first portion of the formatted text, wherein the first portion of the formatted text is a formatted version of a first portion of the original text; and maintaining a linkage between the first fact and the first portion of the original text.

Another embodiment is directed to at least one computer-readable storage medium encoded with a plurality of computer-executable instructions that, when executed, perform a method comprising: receiving an original text that is a representation of a narration of a patient encounter provided by a clinician; re-formatting the original text to produce a formatted text; extracting one or more clinical facts from the formatted text, wherein a first fact of the one or more clinical facts is extracted from a first portion of the formatted text, wherein the first portion of the formatted text is a formatted version of a first portion of the original text; and maintaining a linkage between the first fact and the first portion of the original text.

Another embodiment is directed to a method comprising: extracting, using at least one processor, a plurality of clinical facts from a free-form narration of a patient encounter provided by a clinician, wherein the plurality of clinical facts comprises a first fact and a second fact, wherein the first fact is extracted from a first portion of the free-form narration, and wherein the second fact is extracted from a second portion of the free-form narration; and providing to a user a first indicator that indicates a first linkage between the first fact and the first portion of the free-form narration, and a second indicator, different from the first indicator, that indicates a second linkage between the second fact and the second portion of the free-form narration.

Another embodiment is directed to apparatus comprising at least one processor, and a memory storing processor-executable instructions that, when executed by the at least one processor, perform a method comprising: extracting a plurality of clinical facts from a free-form narration of a patient encounter provided by a clinician, wherein the plurality of clinical facts comprises a first fact and a second fact, wherein the first fact is extracted from a first portion of the free-form narration, and wherein the second fact is extracted from a second portion of the free-form narration; and providing to a user a first indicator that indicates a first linkage between the first fact and the first portion of the free-form narration, and a second indicator, different from the first indicator, that indicates a second linkage between the second fact and the second portion of the free-form narration.

Another embodiment is directed to at least one computer-readable storage medium encoded with a plurality of computer-executable instructions that, when executed, perform a method comprising: extracting a plurality of clinical facts from a free-form narration of a patient encounter provided by a clinician, wherein the plurality of clinical facts comprises a first fact and a second fact, wherein the first fact is extracted from a first portion of the free-form narration, and wherein the second fact is extracted from a second portion of the free-form narration; and providing to a user a first indicator that indicates a first linkage between the first fact and the first portion of the free-form narration, and a second indicator, different from the first indicator, that indicates a second linkage between the second fact and the second portion of the free-form narration.

Another embodiment is directed to a method comprising: collecting a set of one or more clinical facts from a clinician's encounter with a patient; determining from the set of facts, using at least one processor, that an additional fact that provides additional specificity to the set of facts may possibly be ascertained from the patient encounter; and alerting a user that the additional fact may possibly be ascertained from the patient encounter.

Another embodiment is directed to apparatus comprising at least one processor, and a memory storing processor-executable instructions that, when executed by the at least one processor, perform a method comprising: collecting a set of one or more clinical facts from a clinician's encounter with a patient; determining from the set of facts that an additional fact that provides additional specificity to the set of facts may possibly be ascertained from the patient encounter; and alerting a user that the additional fact may possibly be ascertained from the patient encounter.

Another embodiment is directed to at least one computer-readable storage medium encoded with a plurality of computer-executable instructions that, when executed, perform a method comprising: collecting a set of one or more clinical facts from a clinician's encounter with a patient; determining from the set of facts that an additional fact that provides additional specificity to the set of facts may possibly be ascertained from the patient encounter; and alerting a user that the additional fact may possibly be ascertained from the patient encounter.

Another embodiment is directed to a method comprising: collecting a set of one or more clinical facts from a clinician's encounter with a patient; determining, using at least one processor, that an unspecified diagnosis not included in the set of facts may possibly be ascertained from the patient encounter; and alerting a user that the unspecified diagnosis may possibly be ascertained from the patient encounter.

Another embodiment is directed to apparatus comprising at least one processor, and a memory storing processor-executable instructions that, when executed by the at least one processor, perform a method comprising: collecting a set of one or more clinical facts from a clinician's encounter with a patient; determining that an unspecified diagnosis not included in the set of facts may possibly be ascertained from the patient encounter; and alerting a user that the unspecified diagnosis may possibly be ascertained from the patient encounter.

Another embodiment is directed to at least one computer-readable storage medium encoded with a plurality of computer-executable instructions that, when executed, perform a method comprising: collecting a set of one or more clinical facts from a clinician's encounter with a patient; determining that an unspecified diagnosis not included in the set of facts may possibly be ascertained from the patient encounter; and alerting a user that the unspecified diagnosis may possibly be ascertained from the patient encounter.

Another embodiment is directed to a method comprising: determining, based on a free-form narration of a patient encounter provided by a clinician, that one or more clinical facts could possibly be ascertained from the patient encounter; providing to a user one or more options corresponding to the one or more clinical facts; receiving from the user a selection of a first option of the one or more options, the first option corresponding to a first fact of the one or more clinical facts; and updating a textual representation of the free-form narration, using at least one processor, to identify the first fact as having been ascertained from the patient encounter.

Another embodiment is directed to apparatus comprising at least one processor, and a memory storing processor-executable instructions that, when executed by the at least one processor, perform a method comprising: determining, based on a free-form narration of a patient encounter provided by a clinician, that one or more clinical facts could possibly be ascertained from the patient encounter; providing to a user one or more options corresponding to the one or more clinical facts; receiving from the user a selection of a first option of the one or more options, the first option corresponding to a first fact of the one or more clinical facts; and updating a textual representation of the free-form narration to identify the first fact as having been ascertained from the patient encounter.

Another embodiment is directed to at least one computer-readable storage medium encoded with a plurality of computer-executable instructions that, when executed, perform a method comprising: determining, based on a free-form narration of a patient encounter provided by a clinician, that one or more clinical facts could possibly be ascertained from the patient encounter; providing to a user one or more options corresponding to the one or more clinical facts; receiving from the user a selection of a first option of the one or more options, the first option corresponding to a first fact of the one or more clinical facts; and updating a textual representation of the free-form narration to identify the first fact as having been ascertained from the patient encounter.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 2 is a screenshot illustrating an exemplary graphical user interface for a medical fact review system in accordance with some embodiments of the present invention;

FIGS. 3A and 3B are screenshots illustrating an exemplary display of medical facts in a user interface in accordance with some embodiments of the present invention;

DETAILED DESCRIPTION

Figure 1:
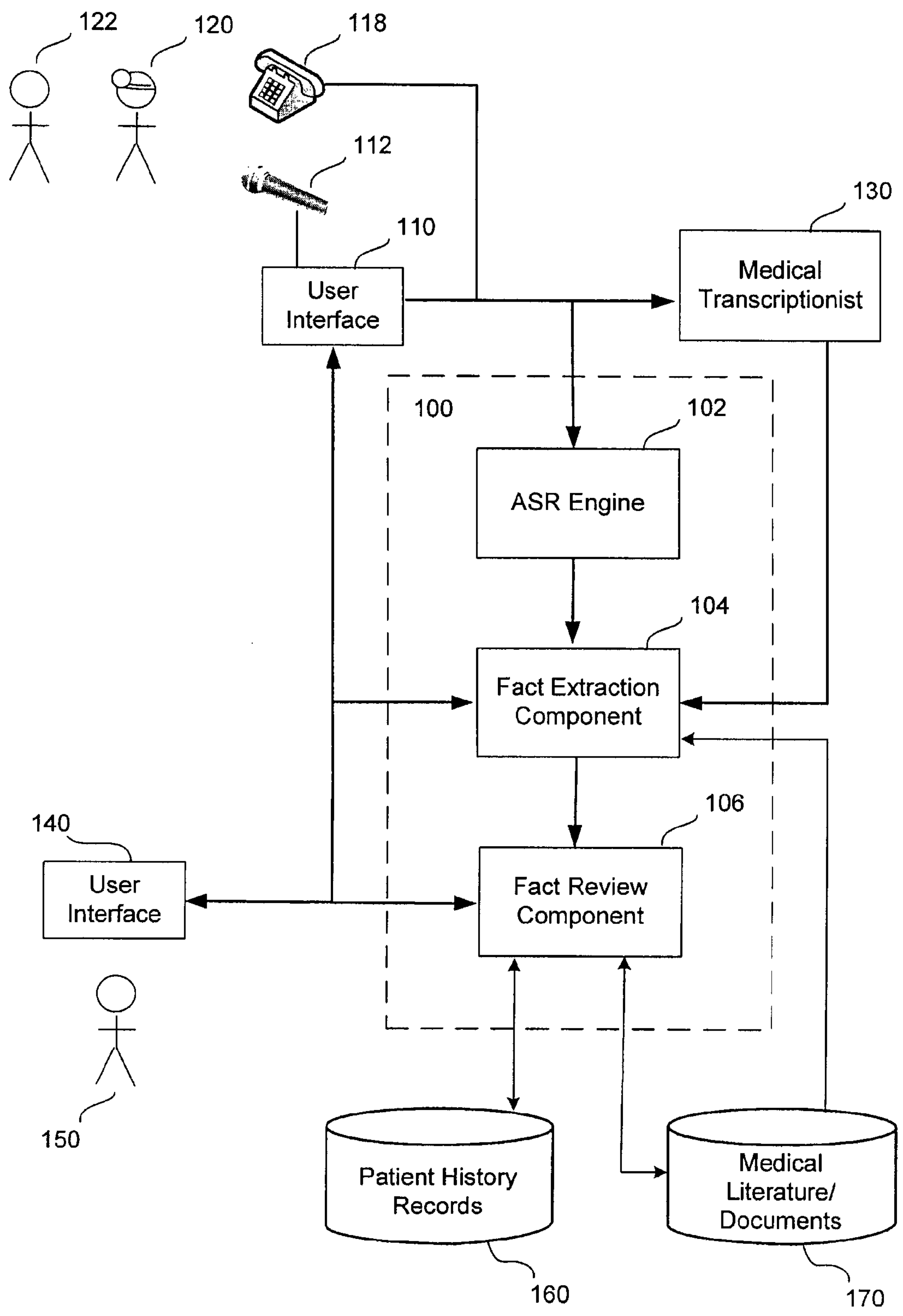
FIG. 1 is a block diagram of an exemplary operating environment for a medical documentation system that may be employed in connection with some embodiments of the present invention.

Software has been developed primarily for use by clinicians to facilitate and automate the process of inputting new entries into clinical documentation, and for increasing the accuracy and completeness of such documentation. Examples of medical documentation systems employing such software are described, for example, in co-pending U.S. patent application Ser. No. 13/030,959, incorporated by reference above, and in U.S. Patent Application Publication No. 2013/0041685, which is also incorporated herein by reference in its entirety. An example of a commercial implementation of this type of system is the Computer Aided Physician Documentation (CAPD) system developed by Nuance. CAPD is a specific use of the Clinical Language Understanding (CLU) engine technology developed by Nuance. CLU is a natural language processing engine that automates the extraction of medical facts and contextual information from the provided clinical documentation.

CAPD takes clinical documentation and processes it thru a CLU engine and, based on the facts and contextual information present in the documentation, evaluates the completeness and accuracy of the documentation. If gaps or issues are found, the CAPD product may automatically generate clarification questions that are presented to the clinician to help clarify and ultimately provide more complete and accurate documentation. CAPD thus provides an automated process for reviewing clinical documentation and presenting any questions to the clinicians interactively and at the time the documentation is generated.

As outlined below, the inventors have recognized certain limitations and drawbacks of current implementations of clinical documentation and review systems that restrict the operability and functionality of such systems in various ways. In current implementations, medical documentation systems, such as the CAPD system, and CDI systems, such as the CDMP Guide, are both used for the purpose of ensuring the accuracy and completeness of medical records. Although the goal for CAPD has been to automate as much of the CDI process as possible, it is not currently feasible to automate the entire process with 100% accuracy. Examples of factors that necessitate the continued use of a separate CDI process are the continued use of handwritten records that cannot be readily interpreted with precision, the availability of certain information, e.g., lab feeds, not supplied to or considered by the medical documentation system, and the lack of 100% precision of the interpreting engine being used, e.g., the CLU engine.

In current implementations, the CDI system and the medical documentation system operate independently. While the CDS who is performing a CDI process may have access to both software platforms concurrently, e.g., by opening them in separate windows on his or her computer, the two platforms are not integrated in any fashion. The CDS must therefore manually input or transfer information from one platform to the other.

In addition, in current implementations, the clinician needs to respond to clarification requests originating from two separate platforms. That is, the clinician receives clarification requests generated automatically by the medical documentation system, e.g., the CAPD system, and will also receive clarification requests generated by the CDS using the CDI system, e.g., the CDMP Guide. This need to interface with multiple separate systems to respond to clarification requests can thus present an inconvenience for clinicians.

Furthermore, in current implementations, clinicians may be prompted by the medical documentation system to provide a clarification that could have readily been addressed by a CDS in the first instance. This lack of initial review by a CDS of at least some such automatically generated clarification requests can thus require the clinician to unnecessarily spend time responding to certain requests.

Some or all of the above limitations and drawbacks of existing implementations may be obviated by embodiments of the systems described herein. In some embodiments, for example, a medical documentation system, e.g., the CAPD system, and a CDI system, e.g., the CDMP Guide, may be linked together, or integrated, so there is a tie between the two systems that allows for a much more efficient and effective CDI process. This disclosure will first describe example implementations of various components that may be employed as the medical documentation system and the CDI system in illustrative embodiments, and will then describe illustrative examples of integration techniques that may be used to interlink or integrate two such systems, as well as example work flows that may be employed using such interlinked or integrated systems.

Medical Documentation System

An Electronic Health Record (EHR) is an electronic medical record that generally is maintained by a specific healthcare institution and contains data documenting the care that a specific patient has received from that institution over time. Typically, an EHR is maintained as a structured data representation, such as a database with structured fields. Each piece of information stored in such an EHR is typically represented as a discrete (e.g., separate) data item occupying a field of the EHR database. For example, a 55-year old male patient named John Doe may have an EHR database record with "John Doe" stored in the patient_name field, "55" stored in the patient_age field, and "Male" stored in the patient_gender field. Data items or fields in such an EHR are structured in the sense that only a certain limited set of valid inputs is allowed for each field. For example, the patient_name field may require an alphabetic string as input, and may have a maximum length limit; the patient_age field may require a string of three numerals, and the leading numeral may have to be "0" or "1"; the patient_gender field may only allow one of two inputs, "Male" and "Female"; a patient_birth_date field may require input in a "MM/DD/YYYY" format; etc.

Typical EHRs are also structured in terms of the vocabulary they use, as medical terms are normalized to a standard set of terms utilized by the institution maintaining the EHR. The standard set of terms may be specific to the institution, or may be a more widely used standard. For example, a clinician dictating or writing a free-form note may use any of a number of different terms for the condition of a patient currently suffering from an interruption of blood supply to the heart, including "heart attack," "acute myocardial infarction," "acute MI" and "AMI." To facilitate interoperability of EHR data between various departments and users in the institution, and/or to allow identical conditions to be identified as such across patient records for data analysis, a typical EHR may use only one standardized term to represent each individual medical concept. For example, "acute myocardial infarction" may be the standard term stored in the EHR for every case of a heart attack occurring at the time of a clinical encounter. Some EHRs may represent medical terms in a data format corresponding to a coding standard, such as the International Classification of Disease (ICD) standard. For example, "acute myocardial infarction" may be represented in an EHR as "ICD-9 410," where 410 is the code number for "acute myocardial infarction" according to the ninth edition of the ICD standard.

To allow clinicians and other healthcare personnel to enter medical documentation data directly into an EHR in its discrete structured data format, many EHRs are accessed through user interfaces that make extensive use of point-and-click input methods. While some data items, such as the patient's name, may require input in (structured) textual or numeric form, many data items can be input simply through the use of a mouse or other pointing input device (e.g., a touch screen) to make selections from pre-set options in drop-down menus and/or sets of checkboxes and/or radio buttons or the like.

Although some clinicians may appreciate the ability to directly enter structured data into an EHR through a point-and-click interface, many clinicians may prefer being unconstrained in what they can say and in what terms they can use in a free-form note, and many may be reluctant to take the time to learn where all the boxes and buttons are and what they all mean in an EHR user interface. In addition, many clinicians may prefer to take advantage of the time savings that can be gained by providing notes through verbal dictation, as speech can often be a faster form of data communication than typing or clicking through forms.

Accordingly, some embodiments described herein relate to techniques for enhancing the creation and use of structured electronic medical records, using techniques that enable a clinician to provide input and observations via a free-form narrative clinician's note. Some embodiments involve the automatic extraction of discrete medical facts (e.g., clinical facts), such as could be stored as discrete structured data items in an electronic medical record, from a clinician's free-form narration of a patient encounter. In this manner, free-form input may be provided, but the advantages of storage, maintenance, and accessing of medical documentation data in electronic forms may be maintained. For example, the storage of a patient's medical documentation data as a collection of discrete structured data items may provide the benefits of being able to query for individual data items of interest, and being able to assemble arbitrary subsets of the patient's data items into new reports, orders, invoices, etc., in an automated and efficient manner.

Automatic extraction of medical facts (e.g., clinical facts) from a free-form narration may be performed in any suitable way using any suitable technique(s), as aspects of the present invention are not limited in this respect. In some embodiments, pre-processing may be performed on a free-form narration prior to performing automatic fact extraction, to determine the sequence of words represented by the free-form narration. Such pre-processing may also be performed in any suitable way using any suitable technique(s), as aspects of the present invention are not limited in this respect. For example, in some embodiments, the clinician may provide the free-form narration directly in textual form (e.g., using a keyboard or other text entry device), and the textual free-form narration may be automatically parsed to determine its sequence of words. In other embodiments, the clinician may provide the free-form narration in audio form as a spoken dictation, and an audio recording of the clinician's spoken dictation may be received and/or stored. The audio input may be processed in any suitable way prior to or in the process of performing fact extraction, as aspects of the invention are not limited in this respect. In some embodiments, the audio input may be processed to form a textual representation, and fact extraction may be performed on the textual representation. Such processing to produce a textual representation may be performed in any suitable way. For example, in some embodiments, the audio recording may be transcribed by a human transcriptionist, while in other embodiments, automatic speech recognition (ASR) may be performed on the audio recording to obtain a textual representation of the free-form narration provided via the clinician's dictation. Any suitable automatic speech recognition technique may be used, as aspects of the present invention are not limited in this respect. In other embodiments, speech-to-text conversion of the clinician's audio dictation may not be required, as a technique that does not involve processing the audio to produce a textual representation may be used to determine what was spoken. In one example, the sequence of words that was spoken may be determined directly from the audio recording, e.g., by comparing the audio recording to stored waveform templates to determine the sequence of words. In other examples, the clinician's speech may not be recognized as words, but may be recognized in another form such as a sequence or collection of abstract concepts. It should be appreciated that the words and/or concepts represented in the clinician's free-form narration may be represented and/or stored as data in any suitable form, including forms other than a textual representation, as aspects of the present invention are not limited in this respect.

In some embodiments, one or more medical facts (e.g., clinical facts) may be automatically extracted from the free-form narration (in audio or textual form) or from a pre-processed data representation of the free-form narration using a fact extraction component applying natural language understanding techniques. In some embodiments, the medical facts to be extracted may be defined by a set of fact categories (also referred to herein as "fact types" or "entity types") commonly used by clinicians in documenting patient encounters. In some embodiments, a suitable set of fact categories may be defined by any of various known healthcare standards. For example, in some embodiments, the medical facts to be extracted may include facts that are required to be documented by Meaningful Use standards promulgated by the U.S. government, e.g., under 42 C.F.R. §495, which sets forth "Objectives" specifying items of medical information to be recorded for medical patients. Such facts currently required by the Meaningful Use standards include social history facts, allergy facts, diagnostic test result facts, medication facts, problem facts, procedure facts, and vital sign facts. However, these are merely exemplary, as aspects of the invention are not limited to any particular set of fact categories. Some embodiments may not use one or more of the above-listed fact categories, and some embodiments may use any other suitable fact categories. Other non-limiting examples of suitable categories of medical facts include findings, disorders, body sites, medical devices, subdivided categories such as observable findings and measurable findings, etc. The fact extraction component may be implemented in any suitable form, as aspects of the present invention are not limited in this respect. Exemplary implementations for a fact extraction component are described in detail below.

The automatic extraction of medical facts (e.g., clinical facts) directly from a free-form narration of a patient encounter provided by a clinician may create the opportunity for numerous enhancements to processes involved in medical documentation in healthcare institutions. Some such enhancements may help make it possible for a clinician to efficiently oversee a process involving deriving any one or combination of updated patient records, billing information, ordering information, quality of care assurances, decision support, etc., directly from a free-form narration in a single interactive session with a medical fact review system.

In some embodiments, automatic extraction of clinical facts from a textual representation of a clinician's free-form narration (e.g., from a text narrative) of a patient encounter may be enhanced by re-formatting the text narrative to facilitate the automatic extraction of the clinical facts. For example, in some embodiments a fact extraction component that performs the automatic fact extraction may make use of linguistic knowledge that has some dependency on accurate placement of sentence boundaries in the text narrative. Accordingly, in some embodiments, the fact extraction may be enhanced by adding, removing, and/or correcting sentence boundaries in the text narrative to comply with the linguistic structure expected by the fact extraction component. Examples of ways in which sentence boundary preprocessing can be implemented are described below. In another example, automatic fact extraction may be enhanced by normalizing section headings in the text narrative to comply with standard section headings used by the healthcare institution for which the clinical documentation is being performed.

In some embodiments, a linkage may be maintained between each extracted clinical fact and the portion of the free-form narration from which that fact was extracted. For example, if a fact corresponding to "acute myocardial infarction" is extracted from a free-form narration because it included the term "heart attack," a linkage may be maintained between that extracted fact and the words "heart attack" in the free-form narration. In some embodiments, while the clinician or another user is reviewing the extracted clinical facts via a user interface to a fact review system, the system may provide one or more indicators to the user (who may be the clinician himself or a different person) of the different linkages between the different extracted facts and the portions of the free-form narration from which they were extracted. Such indicators may be visual indicators, audio indicators, or any other suitable type of indicators, as aspects of the present invention are not limited in this respect. In some embodiments, such linkage indicators may enhance the ability of the clinician or other user to review the extracted facts for accuracy, with reference to the specific parts of the free-form narration that generated them. In some embodiments, if a textual representation of the free-form narration has been re-formatted prior to fact extraction, linkages may still be maintained between the extracted facts and the original text narrative, to allow the user to relate the extracted facts to the narration as it was originally given by the clinician. While some embodiments provide linkage information for each extracted fact, it should be appreciated that aspects of the invention relating to providing linkage information are not so limited, as linkage information may be provided for one or any subset of the extracted facts.

In some embodiments, automatically extracted clinical facts may also be automatically reviewed, and automatic alerts may be provided to the clinician or other user if opportunities are identified for the clinical documentation of the patient encounter to be improved. Such alerts may be visual alerts, audio alerts, or any other suitable type of alerts, as aspects of the present invention are not limited in this respect. In some embodiments, such alerts may be provided to the clinician or other user at a time subsequent to the completion of the patient encounter, and may provide the opportunity for the clinician or other user to provide additional information that was ascertained from the patient encounter but was not originally specified in the free-form narration. In other embodiments, such alerts may be provided to the clinician while the patient encounter is still in progress, and may provide the opportunity for the clinician to initiate further interaction with the patient to ascertain additional information to include in the clinical documentation.

In some embodiments, a fact review system may be programmed with a set of deterministic rules to trigger alerts. For example, a set of deterministic rules may specify that certain extracted facts, certain combinations of extracted facts, certain combinations of extracted facts and terms in the free-form narration, and/or certain combinations of facts extracted from the current patient encounter and facts from the patient's previous history automatically trigger alerts to the user. In other embodiments, the fact review system may be programmed to undertake a probabilistic analysis or apply a statistical model to determine whether information specified in the free-form narration will trigger alerts to the user. It should be appreciated, however, that a fact review system in accordance with embodiments described herein is not limited to any particular programming technique, as any suitable such technique may be used. In addition, it should be appreciated that automatic alerts may also be provided in embodiments that do not involve automatic extraction of clinical facts from a free-form narration. For example, such alerts may also be triggered by clinical facts received as discrete structured data items, such as direct input to an electronic medical record such as an EHR. It should thus be appreciated that alerts may be provided based on analysis of clinical facts collected in any suitable way, as aspects of the present invention are not limited in this respect.

In some embodiments, an alert may be provided when a set of one or more clinical facts is collected from a patient encounter, and it is determined that there is an opportunity to increase the specificity of the set of facts. In some embodiments, it may be determined that an additional fact may possibly be ascertained from the patient encounter, and that the additional fact would add specificity to the set of clinical facts already collected from the patient encounter. In one example, such an additional fact may be a more specific version of one of the original facts, and the specificity of the set of facts may be increased by replacing the original fact with its more specific version, provided that it can truly be ascertained from the patient encounter. For instance, the original fact may describe a condition, and the more specific version may describe the same condition as "acute" or "chronic." In another example, two or more of the original facts, when appearing in combination, may imply an additional fact, and documenting the additional fact may increase the specificity of the record of the patient encounter. In some embodiments, an alert may query the user as to whether an additional fact should actually be ascertained from the patient encounter, and may allow the user to increase the specificity of the facts by documenting the additional fact.

In some embodiments, an alert may be provided when a set of one or more clinical facts is collected from a patient encounter, and it is determined that a diagnosis that was not specified in the set of facts may possibly be ascertained from the patient encounter. In one example, such an unspecified diagnosis may be a known comorbidity of a diagnosis that was included in the set of facts. In another example, the unspecified diagnosis may be a known complication of a procedure or diagnosis included in the set of facts. In yet another example, the unspecified diagnosis may be an identification of the fact that a diagnosis included in the set of facts is actually a complication of a procedure or other diagnosis included in the set of facts, or of a procedure or other diagnosis included in facts from the patient's history prior to the current encounter. Similarly, the unspecified diagnosis may be an identification of the fact that a diagnosis included in facts from the patient's previous history is a complication of a diagnosis ascertained during the current patient encounter. In some embodiments, when the possibility or likelihood of such an unspecified diagnosis is determined from the original set of facts collected from the patient encounter, an alert may query the user (e.g., the clinician or another user) as to whether the unspecified diagnosis should be ascertained from the patient encounter.

In some embodiments, an alert may be provided when a set of one or more clinical facts is collected from a patient encounter, and it is determined that two or more of the facts in the set conflict with each other in some way, or it is determined that one or more of the facts in the set conflict with one or more facts in the patient's history. In some embodiments, a fact review system may be programmed to automatically generate such alerts based on a known set of combinations of facts that have undesirable interactions. For example, an alert may be generated when the set of facts indicate that the patient has been prescribed a certain medication (drug A) in addition to a certain other medication (drug B) with which it negatively interacts, such that the two medications should not be prescribed together. In some embodiments, the prescriptions of both drug A and drug B may be specified in the set of facts collected from the current patient encounter, while in other embodiments, the prescription of drug A may be specified in a fact from the current patient encounter, and the prescription of drug B may be specified in a fact contained in a record of the patient's history with the institution. Thus, in some embodiments, the fact review system may access both facts collected from a current patient encounter and facts from the patient's historical records to determine whether alerts should be generated. In some embodiments, an alert to a conflict may be triggered by a combination of facts, at least one of which does not correspond to a medication. For example, alerts may be provided for contraindications related to a combination of a medication with an allergy, a medication with a diagnosis, a medication with a patient's age or gender, a medication with a condition indicated in the patient's history, a medical procedure with any of the foregoing characteristics, or any other combination of a planned treatment with another clinical fact from the current patient encounter or from the patient's history for which the planned treatment is known to be contraindicated.

In some embodiments, an alert may be provided when a set of one or more clinical facts is collected from a patient encounter, and it is determined that there is an opportunity to add to the clinical documentation of the patient encounter for quality review purposes. In some embodiments, a fact review system may be programmed with a set of deterministic rules to generate automatic alerts in response to certain facts or certain combinations of facts, based on a standard set of quality of care measures. Such a quality of care standard may be proprietary and unique to the specific healthcare institution or may be a standard that is not institution specific, such as that of the Physician Quality Reporting Initiative (PQRI) or that of the Joint Commission on Accreditation of Healthcare Organizations (JCAHO). Any suitable quality of care standard may be used, as aspects of the present invention are not limited to any particular quality of care standard. In some embodiments, when a collected fact or combination of facts is associated with a certain recommended action on the part of the clinician according to the quality of care standard, an alert may be provided to query the user as to whether the recommended action was performed.

In some embodiments, a mechanism may be provided to adaptively filter the automatic alerts generated by the fact review system, by learning from the clinician's or other user's interaction with the system over time. For example, if it is determined that a particular user consistently ignores a particular type of alert, the system may stop issuing similar alerts when they are triggered by future facts. In some embodiments, the adaptive learning may be specific to each individual user and may help to prevent alert fatigue, which may involve frustration at repeatedly being bothered by an alert that the user does not find relevant. In some embodiments, the adaptive learning may involve the collection of data regarding patterns of facts that tend to be present when the user ignores alerts, and the system may filter out future alerts that match those patterns of facts. In some embodiments, adaptive alert filtering may be performed based on rules or statistical usage patterns on an institutional level, such that alerts not considered relevant for the specific healthcare institution in which the fact review system is operating are not provided.

In some embodiments, a human user other than the clinician may review the set of clinical facts collected from a patient encounter, and may manually (e.g., not automatically, but involving human action) cause one or more alerts to be issued to the clinician that were not issued automatically by the fact review system. Such a human user may manually cause alerts to be issued in any suitable way, as aspects of the invention are not limited in this respect. In one example, the human user may provide instructional input to the fact review system to cause the fact review system to generate an alert specified by the human user. In other examples, the human user may use a different method and/or system, other than the fact review system, to issue an alert to the clinician. Such a different method in some embodiments need not be machine-based, as aspects of the invention are not limited in this respect. In some embodiments, the human user may have access to the patient's past medical history within and/or external to the healthcare institution, for example in the form of an electronic medical record and/or past clinical documents relating to the patient's care at the institution and/or elsewhere. In some embodiments, the human user may make reference to this past medical history, in addition to the clinical facts from the current patient encounter, to determine whether to manually cause an alert to be issued to the clinician. In some embodiments, the human user may determine to issue an alert, similar to any of the various types of automatic alerts described above, if the facts and the patient's history indicate a situation in which the automatic fact review system should have generated an automatic alert, but it failed to accurately recognize the situation. In some embodiments, if the clinician chose to ignore an alert automatically generated by the fact review system, but ignoring such an alert was contrary to the policy of the institution, the human reviewer may determine to manually issue a follow-up alert to the clinician. Thus, in some embodiments, an automatic fact review system may coexist in an institutional setting with a manual review process involving a human user, and the manual review process may provide back-up and/or additional functionality to complement the automatic fact review processes.

In some embodiments, when medical facts are extracted from a free-form narration, a fact extraction component may encounter situations in which disambiguation is desired between multiple facts that could potentially be extracted from the same portion of the free-form narration. In one example, a term in the free-form narration might be linked to two different concepts in a formal ontology (described below) used by the fact extraction component, and it might not be likely that both of those concepts were intended to coexist in the free-form narration. In another example, the fact extraction component may apply a statistical model (examples of which are described below) to identify facts to be extracted from a certain portion of text, and the statistical model may come up with multiple alternative hypotheses for a single fact to be extracted. In some embodiments, the statistical model may be used to score the alternative hypotheses based on probability, confidence, or any other suitable measure of an estimated likelihood that each alternative accurately represents an intended semantic meaning of the portion of text from which it is to be extracted. In such situations, a fact review system in some embodiments may provide an interface to receive user input to disambiguate between multiple facts tentatively extracted by the fact extraction component. Such a user interface can be in any suitable form, as aspects of the invention are not limited in this respect. In one non-limiting example, the fact review system may present to the user a certain number of the alternative hypotheses having high estimated likelihood scores. In some embodiments, each of the options provided may correspond to one of the multiple tentative facts, and the user may choose one of the options to specify which fact should actually be extracted from the free-form narration.

In some cases, when the user makes a selection of a fact presented through a structured choice provided by the fact review system, the set of facts extracted by the fact extraction component may be updated accordingly, but the original free-form narration from which the facts were extracted may remain unchanged. In some embodiments, in other cases, a textual representation of the clinician's free-form narration may automatically be updated (e.g., changed) to explicitly identify the user's selected fact as having been ascertained from the patient encounter. For example, if the free-form narration originally included a term linked to two different concepts in the fact extraction component's ontology, the fact review system could present the user a structured choice between a different term linked only to one of the concepts and a different term linked only to the other of the concepts. When the user selects one of the different terms in the structured choice presented, in some embodiments the text narrative may automatically be updated to replace the original term with the selected term. In another example, if application of a statistical fact extraction model resulted in multiple alternative hypotheses for a fact to be extracted from a certain portion of the free-form narration, the fact review system could present the user a choice between at least two of the alternative hypotheses (e.g., the N alternative hypotheses having the highest scores). In some cases in some embodiments, the text narrative may automatically be updated to better reflect the alternative hypothesis selected by the user. For example, if the original text narrative included the term "asthma," the fact extraction component might present alternative fact hypotheses of "chronic obstructive asthma" and "asthma unspecified." If the user then selects the "chronic obstructive asthma" hypothesis (representing a more specific asthma fact), then the text narrative could automatically be updated to replace the original "asthma" term with "chronic obstructive asthma." In some embodiments, such updating of the text narrative may be performed in response to any type of user selection of an option provided by the fact review system, corresponding to a medical fact that could possibly be ascertained from the patient encounter. Some examples include disambiguating options, options corresponding to additional facts for increased specificity and options corresponding to unspecified diagnoses, as discussed above. In some embodiments, rather than replacing text in the narrative, new text corresponding to the selected fact may be generated and simply added to the narrative in one or more appropriate locations. In some embodiments, the location(s) at which to insert text identifying the selected fact may be automatically determined by identifying one or more section headings in the text narrative, and by inserting the text in the section or sections most closely corresponding to the selected fact.

In some embodiments, a fact review system may allow a clinician or other user to directly add a clinical fact as a discrete structured data item, and to indicate a linkage to a portion of the clinician's free-form narration of the patient encounter from which the added fact should have been extracted. For example, the user may specify a clinical fact as a discrete structured data element, select a word or set of words (which need not be contiguous) in the free-form narration, and indicate that the specified fact is ascertained from that portion (e.g., that word or set of words) of the free-form narration. In some embodiments, when such a fact is added, the fact extraction component may be updated for that user (or for the clinician who provided the free-form narration), e.g., to link the selected word(s) from the free-form narration to one or more concepts in a formal ontology corresponding to the added fact, or to re-train a statistical fact extraction model to associate the selected word(s) with the added fact. In some embodiments, the free-form narration may further be re-processed by the updated fact extraction component to extract any further additional facts that may be determined based on the updated terminology. In one example, if the user selected a word in the patient history section of the free-form narration, and added a fact specifying that the patient has a history of a particular condition, the updated fact extraction component re-processing the free-form narration might identify the same word in the family history section, and extract an additional fact that the patient has a family history of the same condition. In some embodiments, such automatic re-processing may spare the clinician or other user the time and effort that otherwise would be required to define multiple facts corresponding to the same terminology in the free-form narration. In some embodiments, similar re-processing may be performed when the user edits or deletes a fact originally extracted automatically from the free-form narration, when the fact is linked to terminology that appears in multiple parts of the free-form narration.

In some embodiments, as discussed above, a fact review system may allow a user to add, delete and/or modify (collectively referred to as "change") a medical fact extracted from a free-form narration of a patient encounter provided by a clinician, resulting in a change to the set of extracted facts. For example, in some embodiments, a user may add a fact to the set of extracted facts, e.g., by specifying a portion of the free-form narration and specifying a particular fact that should be extracted from that portion of the narration. In some embodiments, a user may specify an added fact directly, e.g., by typing, speaking, or otherwise inputting the particular fact to be added, or by selecting the fact and/or components of the fact from menu options. Alternatively or additionally, as described above, in some embodiments the system may present the user with a choice between multiple alternative hypotheses for a fact to be extracted from a portion of the free-form narration, and the user may select one of the presented hypotheses to add that fact to the set of extracted facts. In another example, a user may modify a fact already automatically extracted from the free-form narration, e.g., by selecting the extracted fact and inputting a different fact with which it should be replaced, or by selecting a component of the extracted fact and inputting a change to that component, etc. In another example, a user may delete an extracted fact, e.g., by selecting the extracted fact and selecting a "delete" option, or otherwise indicating that that fact should not have been extracted from the corresponding portion of the free-form narration. It should be appreciated, however, that the foregoing are merely examples, and a user may be allowed to add, delete and/or modify one or more facts in a set of extracted medical facts in any suitable way, as aspects of the invention are not limited in this respect.

When a user inputs a change (e.g., an addition, deletion, or modification) to a set of one or more facts already automatically extracted from a free-form narration, such a change is referred to herein as a "correction" to the set of extracted facts. In some embodiments, a user may input a correction to an extracted set of medical facts in any suitable way, and the fact review system may then apply the user's correction throughout the free-form narration. In such a way, in some embodiments, a user may be able to correct the fact extraction component's treatment of one portion of the narrative text, and similar corrections may then be applied automatically to other portions of the text, without the user having to directly specify the same type of correction for every similar portion of text in the document. For a non-limiting example, consider the exemplary narrative text below:

CHIEF COMPLAINT: Epileptic myoclonic twitches of the upper extremity.

PAST MEDICAL HISTORY: History of developmental delay and myoclonic seizure involving the upper extremities.

ASSESSMENT: Myoclonic jerks involving the upper extremities.

Assume that an automatic fact extraction component failed to extract the clinician's intended meaning (the intended medical fact) from the text portion "Epileptic myoclonic twitches of the upper extremity." The text portions "myoclonic seizure involving the upper extremities" and "Myoclonic jerks involving the upper extremities" communicate similar semantic meanings, so the automatic fact extraction component is unlikely to successfully extract the intended medical fact from these text portions either. In some embodiments, a user could correct the fact extraction by selecting the text portion "Epileptic myoclonic twitches," and adding a corresponding medical fact "myoclonic epileptic seizure," which corresponds to ICD-9 code 345.1. In some embodiments, upon analyzing the user's correction to the fact extraction from the first portion of the text, the fact review system may learn from the association and may automatically apply similar corrections to the rest of the narrative text. For example, the fact review system may identify the other text portions "myoclonic seizure" and "myoclonic jerks" as being similar to the first text portion "Epileptic myoclonic seizures," and may automatically extract the fact "myoclonic epileptic seizure," corresponding to ICD-9 code 345.1, from the other two text portions as well. In this example, in some embodiments, the system may extract similar facts (e.g., facts that are not necessarily identical to the fact added by the user) from the other portions of the text, since the other text portions may have similar, but not necessarily identical, intended semantic meanings as the first text portion. For example, in the above narrative, both text portions "Epileptic myoclonic twitches" and "myoclonic seizure" indicate a medical problem with a normalized form of "myoclonic epileptic seizure," but the second portion occurs in the "PAST MEDICAL HISTORY" section, while the first portion occurs in the "CHIEF COMPLAINT" section. Thus, in some embodiments, the system may automatically extract a similar medical fact from the second portion, but the fact extracted from the second portion may indicate that the problem is a past history problem rather than a current problem.

Thus, in some embodiments, a user may identify a fact that should be associated with a first portion of the narrative text, and the system may then automatically extract one or more similar facts from one or more other portions of the narrative text. The user may identify the fact that should be associated with the first text portion in any suitable way. For example, as discussed above, in some cases the user may select a portion of the narrative text, and may directly specify a fact that should be extracted from that portion of the text. In other cases, the fact extraction component may present to the user multiple options corresponding to alternative hypotheses for a fact to be extracted from the portion of the narrative text, and the user may identify the fact that should be associated with that text portion by selecting one of the alternative hypotheses presented. In still other cases, a user may select a fact that was already extracted from a portion of the narrative text, and may specify a modification that should be made to the extracted fact, thus identifying the correct fact that should be associated with the text portion. It should be appreciated, however, that the foregoing are merely examples, and a user may identify a fact that should be associated with a portion of the narrative text in any suitable way, as aspects of the invention are not limited in this respect.

In still other examples, a user may delete a fact that was extracted from a first portion of the narrative text, and the system may then automatically delete one or more other instances of the same extracted fact (or of similar extracted facts) from one or more other portions of the narrative text. It should further be appreciated, however, that adding, deleting, and modifying facts as described above are only examples, and the user may be permitted to correct a set of extracted medical facts in any suitable way, as aspects of the invention are not limited in this respect. In some embodiments, any suitable type of correction made by a user to one or more facts extracted from a first portion of a narrative text may then automatically be applied to one or more other portions of the narrative text. Furthermore, in some embodiments, any suitable type of correction made by a user to a set of facts extracted from a first narrative text may alternatively or additionally be automatically applied to other narrative texts processed by the fact extraction component in the future. In some embodiments, one or more fact extraction models used by the fact extraction component may be re-trained such that the correction applied to the first text may be reflected in the manner of processing later texts. Exemplary techniques for applying a user correction throughout the text in which it occurs, as well as exemplary techniques for reflecting such a correction in the processing of other texts, are described below.

In some instances, one or more such changes made to the set of facts corresponding to the current patient encounter may create one or more inconsistencies between the set of facts and the semantic content of the original free-form narration. For example, a clinician may originally specify a particular diagnosis in a free-form narration, and a fact extraction component may extract a clinical fact corresponding to that diagnosis. If the clinician later changes his mind and would like to replace the original diagnosis with a different diagnosis, he may have the option in some embodiments of simply editing the extracted fact directly, rather than editing the data representation of the free-form narration itself. Such a situation may create an inconsistency between the free-form narration and the corresponding set of clinical facts, as the facts may now specify the new diagnosis, and the free-form narration may still specify the original diagnosis. In such situations, the fact review system in some embodiments may alert the clinician or other user to the inconsistency, and/or may provide any of several options to the user to address the inconsistency. One option may be to ignore the inconsistency and allow it to persist in the clinical documentation. Another option may be to allow the user to edit the data representation of the free-form narration to be consistent with the current set of clinical facts. Another option may be to allow the system to automatically update the data representation of the free-form narration by adding, deleting or replacing one or more portions of the free-form narration. Yet another option may be simply to append a note to the free-form narration, indicating and optionally explaining the inconsistency.

In some embodiments, as discussed above, a medical fact review system may provide various tools for a clinician to review and/or edit facts corresponding to a current patient encounter, receive alerts generated based on those facts, review and/or edit a free-form narration of the patient encounter provided by the clinician, and/or review the linkages maintained between medical facts extracted by a fact extraction component and the portions of the free-form narration from which the medical facts were extracted. Such tools may be provided in any suitable form, including visual forms, audio forms, combined forms, or any other form providing the functionality described herein, as aspects of the present invention are not limited in this respect. When the tools are provided in visual form, their functionality may be accessed through a graphical user interface (GUI). In some embodiments, the GUI may be organized in a way to allow the human user(s) to efficiently process the information displayed. For example, in some embodiments, text narratives, facts, and alerts may be displayed in consistent locations within the user interface and organized by type and/or priority. Different colors, textual styles, and/or graphical styles may be utilized to direct the user's attention to high-priority alerts, and/or to make linkages between related items in the display easily recognizable. In some embodiments, the organization and/or composition of such a visual display may be determined in accordance with principles used in the development of heads-up displays (HUDs).

In some embodiments, a fact review system operating on a set of clinical facts ascertained from a patient encounter may provide tools for promoting efficiency in the workflow of the clinician and/or other personnel beyond the conclusion of the patient encounter. For example, in some embodiments, the fact review system may interface with one or more Computerized Physician Order Entry (CPOE) systems to automatically place orders for prescriptions, laboratory tests, radiology screenings, surgical or other medical procedures and/or other planned treatment action items, based on such items (e.g., medication names, dosages, procedure names, dates, etc.) being specified in the set of facts corresponding to the current patient encounter. In some embodiments, such items may be identified based on their being extracted from a "plan" section of a free-form narration. In some embodiments, the fact review system may interface with one or more scheduling systems to schedule appointments for medical procedures and/or future office visits within or external to the institution. In some embodiments, the fact review system may format one or more facts into a standard or proprietary messaging format to facilitate interfacing with any of such systems. In some embodiments, billing reports, patient discharge instructions and/or other documents may be automatically generated or initially populated based on the set of clinical facts. In some embodiments with any of the above-described functionality, the fact review system may provide an alert to the user and/or may prompt for user or clinician approval prior to taking any of the above actions.

In some embodiments, a fact review system may provide tools for evidence-based clinical decision support based on the set of clinical facts collected for the current patient encounter. In some embodiments, the fact review system may have access to one or more data sets of past patient reports and/or one or more archives of medical literature documents that may provide information regarding various conditions, treatment outcomes and the like that are relevant to the current patient encounter. In some embodiments, the available documents may have been processed by the fact extraction component and indexed using the same system of terminology used to extract clinical facts from free-form clinical narrations. As such, in some embodiments, the facts corresponding to the current patient encounter may be efficiently matched to relevant available documents, and those documents or a subset thereof may be retrieved for display or otherwise provided to the clinician to aid in his determination of a treatment plan for the current patient. In some embodiments, a statistical model may be trained on the data set of past patient outcomes and/or on data in the medical literature, such that the system may go beyond mere presentation of references to actually predict best courses of treatment by applying the statistical model to the collection of facts corresponding to the current patient encounter and/or to the patient's medical history. In some embodiments, treatment recommendations may be provided to the clinician along with links to references in the literature or other available data supporting the recommendations. In some embodiments, clinical language understanding (CLU) indexing of large quantities of patient records and/or literature documents may also be used to facilitate clinical research studies, as available natural language documents may be efficiently mapped to an ad hoc query corresponding to a research question. From the resulting corpus of conceptually relevant documents, treatment outcomes and/or other required information or facts may be extracted using CLU technology to aid in synthesizing an answer to the research question.

While a number of features for clinical documentation processes are described above, it should be appreciated that embodiments of the present invention may include any one of these features, any combination of two or more features, or all of the features, as aspects of the invention are not limited to any particular number or combination of the above-described features. The aspects of the present invention described herein can be implemented in any of numerous ways, and are not limited to any particular implementation techniques. Described below are examples of specific implementation techniques; however, it should be appreciated that these examples are provided merely for purposes of illustration, and that other implementations are possible.

One illustrative application for the techniques described herein is for use in a system for enhancing medical documentation processes. An exemplary operating environment for such a clinician documentation system is illustrated in FIG. 1. The exemplary operating environment includes a medical documentation system 100, which may be implemented in any suitable form, as aspects of the present invention are not limited in this respect. For example, system 100 may be implemented as a single stand-alone machine, or may be implemented by multiple distributed machines that share processing tasks in any suitable manner. System 100 may be implemented as one or more computers; an example of a suitable computer is described below. In some embodiments, system 100 may include one or more tangible, non-transitory computer-readable storage devices storing processor-executable instructions, and one or more processors that execute the processor-executable instructions to perform the functions described herein. The storage devices may be implemented as computer-readable storage media encoded with the processor-executable instructions; examples of suitable computer-readable storage media are discussed below.

As depicted, exemplary system 100 includes an ASR engine 102, a fact extraction component 104, and a fact review component 106. Each of these processing components of system 100 may be implemented in software, hardware, or a combination of software and hardware. Components implemented in software may comprise sets of processor-executable instructions that may be executed by the one or more processors of system 100 to perform the functionality described herein. Each of ASR engine 102, fact extraction component 104, and fact review component 106 may be implemented as a separate component of system 100, or any combination of these components may be integrated into a single component or a set of distributed components. In addition, any one of ASR engine 102, fact extraction component 104, and fact review component 106 may be implemented as a set of multiple software and/or hardware components. It should be understood that any such component depicted in FIG. 1 is not limited to any particular software and/or hardware implementation and/or configuration.

As illustrated in FIG. 1, user interface 110 is presented to a clinician 120, who may be a physician, a physician's aide, a nurse, or any other personnel involved in the evaluation and/or treatment of a patient 122 in a clinical setting. During the course of a clinical encounter with patient 122, or at some point thereafter, clinician 120 may wish to document the patient encounter. Such a patient encounter may include any interaction between clinician 120 and patient 122 in a clinical evaluation and/or treatment setting, including, but not limited to, an office visit, an interaction during hospital rounds, an outpatient or inpatient procedure (surgical or non-surgical), a follow-up evaluation, a visit for laboratory or radiology testing, etc. One method that clinician 120 may use to document the patient encounter may be to enter medical facts that can be ascertained from the patient encounter into user interface 110 as discrete structured data items. The set of medical facts, once entered, may be transmitted in some embodiments via any suitable communication medium or media (e.g., local and/or network connection(s) that may include wired and/or wireless connection(s)) to system 100. Specifically, in some embodiments, the set of medical facts may be received at system 100 by a fact review component 106, exemplary functions of which are described below.

Another method that may be used by clinician 120 to document the patient encounter is to provide a free-form narration of the patient encounter. In some embodiments, the narration may be free-form in the sense that clinician 120 may be unconstrained with regard to the structure and content of the narration, and may be free to provide any sequence of words, sentences, paragraphs, sections, etc., that he would like. In some embodiments, there may be no limitation on the length of the free-form narration, or the length may be limited only by the processing capabilities of the user interface into which it is entered or of the later processing components that will operate upon it. In other embodiments, the free-form narration may be constrained in length (e.g., limited to a particular number of characters).

A free-form narration of the patient encounter may be provided by clinician 120 in any of various ways. One way may be to manually enter the free-form narration in textual form into user interface 110, e.g., using a keyboard. In this respect, the one or more processors of system 100 and/or of a client device in communication with system 100 may in some embodiments be programmed to present a user interface including a text editor/word processor to clinician 120. Such a text editor/word processor may be implemented in any suitable way, as aspects of the present invention are not limited in this respect.

Another way to provide a free-form narration of the patient encounter may be to verbally speak a dictation of the patient encounter. Such a spoken dictation may be provided in any suitable way, as aspects of the present invention are not limited in this respect. As illustrated in FIG. 1, one way that clinician 120 may provide a spoken dictation of the free-form narration may be to speak the dictation into a microphone 112 providing input (e.g., via a direct wired connection, a direct wireless connection, or via a connection through an intermediate device) to user interface 110. An audio recording of the spoken dictation may then be stored in any suitable data format, and transmitted to system 100 and/or to medical transcriptionist 130. Another way that clinician 120 may provide the spoken dictation may be to speak into a telephone 118, from which an audio signal may be transmitted to be recorded at system 100, at the site of medical transcriptionist 130, or at any other suitable location. Alternatively, the audio signal may be recorded in any suitable data format at an intermediate facility, and the audio data may then be relayed to system 100 and/or to medical transcriptionist 130.

In some embodiments, medical transcriptionist 130 may receive the audio recording of the dictation provided by clinician 120, and may transcribe it into a textual representation of the free-form narration (e.g., into a text narrative). Medical transcriptionist 130 may be any human who listens to the audio dictation and writes or types what was spoken into a text document. In some embodiments, medical transcriptionist 130 may be specifically trained in the field of medical transcription, and may be well-versed in medical terminology. In some embodiments, medical transcriptionist 130 may transcribe exactly what she hears in the audio dictation, while in other embodiments medical transcriptionist 130 may add formatting to the text transcription to comply with generally accepted medical document standards. When medical transcriptionist 130 has completed the transcription of the free-form narration into a textual representation, the resulting text narrative may in some embodiments be transmitted to system 100 or any other suitable location (e.g., to a storage location accessible to system 100). Specifically, in some embodiments the text narrative may be received from medical transcriptionist 130 by fact extraction component 104 within system 100. Exemplary functionality of fact extraction component 104 is described below.

In some other embodiments, the audio recording of the spoken dictation may be received, at system 100 or any other suitable location, by automatic speech recognition (ASR) engine 102. In some embodiments, ASR engine 102 may then process the audio recording to determine what was spoken. As discussed above, such processing may involve any suitable speech recognition technique, as aspects of the present invention are not limited in this respect. In some embodiments, the audio recording may be automatically converted to a textual representation, while in other embodiments, words identified directly from the audio recording may be represented in a data format other than text, or abstract concepts may be identified instead of words. Examples of further processing are described below with reference to a text narrative that is a textual representation of the free-form narration; however, it should be appreciated that similar processing may be performed on other representations of the free-form narration as discussed above. When a textual representation is produced, in some embodiments it may be reviewed by a human (e.g., a transcriptionist) for accuracy, while in other embodiments the output of ASR engine 102 may be accepted as accurate without human review. As discussed above, some embodiments are not limited to any particular method for transcribing audio data; an audio recording of a spoken dictation may be transcribed manually by a human transcriptionist, automatically by ASR, or semi-automatically by human editing of a draft transcription produced by ASR. Transcriptions produced by ASR engine 102 and/or by transcriptionist 130 may be encoded or otherwise represented as data in any suitable form, as aspects of the invention are not limited in this respect.

In some embodiments, ASR engine 102 may make use of a lexicon of medical terms (which may be part of, or in addition to, another more general speech recognition lexicon) while determining the sequence of words that were spoken in the free-form narration provided by clinician 120. However, aspects of the invention are not limited to the use of a lexicon, or any particular type of lexicon, for ASR. When used, the medical lexicon in some embodiments may be linked to a knowledge representation model such as a clinical language understanding ontology utilized by fact extraction component 104, such that ASR engine 102 might produce a text narrative containing terms in a form understandable to fact extraction component 104. In some embodiments, a more general speech recognition lexicon might also be shared between ASR engine 102 and fact extraction component 104. However, in other embodiments, ASR engine 102 may not have any lexicon developed to be in common with fact extraction component 104. In some embodiments, a lexicon used by ASR engine 102 may be linked to a different type of medical knowledge representation model, such as one not designed or used for language understanding. It should be appreciated that any lexicon used by ASR engine 102 and/or fact extraction component 104 may be implemented and/or represented as data in any suitable way, as aspects of the invention are not limited in this respect.

In some embodiments, a text narrative, whether produced by ASR engine 102 (and optionally verified or not by a human), produced by medical transcriptionist 130, directly entered in textual form through user interface 110, or produced in any other way, may be re-formatted in one or more ways before being received by fact extraction component 104. Such re-formatting may be performed by ASR engine 102, by a component of fact extraction component 104, by a combination of ASR engine 102 and fact extraction component 104, or by any other suitable software and/or hardware component. In some embodiments, the re-formatting may be performed in a way known to facilitate fact extraction, and may be performed for the purpose of facilitating the extraction of clinical facts from the text narrative by fact extraction component 104. For example, in some embodiments, processing to perform fact extraction may be improved if sentence boundaries in the text narrative are accurate. Accordingly, in some embodiments, the text narrative may be re-formatted prior to fact extraction to add, remove, or correct one or more sentence boundaries within the text narrative. In some embodiments, this may involve altering the punctuation in at least one location within the text narrative. In another example, fact extraction may be improved if the text narrative is organized into sections with headings, and thus the re-formatting may include determining one or more section boundaries in the text narrative and adding, removing or to correcting one or more corresponding section headings. In some embodiments, the re-formatting may include normalizing one or more section headings (which may have been present in the original text narrative and/or added or corrected as part of the re-formatting) according to a standard for the healthcare institution corresponding to the patient encounter (which may be an institution-specific standard or a more general standard for section headings in clinical documents). In some embodiments, a user (such as clinician 120, medical transcriptionist 130, or another user) may be prompted to approve the re-formatted text.

Any suitable technique(s) for implementing re-formatting, examples of which are described above, may be employed, as aspects of the invention are not limited in this respect. One exemplary technique suitable for performing re-formatting of a text narrative is described in U.S. patent application Ser. No. 11/322,971, filed on Dec. 30, 2005, entitled "Translating Literal Speech to Formatted Text," which is incorporated herein by reference in its entirety. Another exemplary technique that may be used in some embodiments for performing re-formatting of a text narrative involves the use of word N-gram statistical models to predict sentence and/or section boundaries in a text narrative. Such statistical models may be trained on a corpus of documents (e.g., past medical records) with correct punctuation and/or section headings (e.g., supplied by a medical transcriptionist).

In some embodiments, a statistical model may add punctuation (e.g., periods, exclamation points, question marks, etc.) to add one or more sentence boundaries to a text narrative by computing a probability, for each word in the text narrative, that a particular punctuation mark should follow that word. In computing the probability that a word should be followed by a punctuation mark, the statistical model may consider the N-word sequence from the text narrative that ends with that word, and determine the frequency with which that N-word sequence is followed by that punctuation mark in the training data for the statistical model. A lattice may then be constructed using the computed probabilities for all the words in the text narrative, or in a portion of the text narrative, and the best path in terms of combined probability through the lattice may be determined. Where punctuation marks are located in the best path through the lattice, those punctuation marks may be added in those locations to the text narrative in producing the formatted text. In some embodiments, another statistical model may add section headings, corresponding to section boundaries, in a similar fashion. For example, in some embodiments, a statistical model for section headings may compute probabilities, for each word, that the word should be followed by a section boundary. In some embodiments, in computing probabilities, a statistical model for section headings may consider more words that follow the current word than words that precede the current word. In some embodiments, one or more separate statistical models may be trained to delete incorrect sentence and/or section boundaries. Those models in some embodiments may be trained through feedback from clinician 120 or another user, by observing word sequences (initially including punctuation and/or section boundaries) from which clinician 120 or another user tends to remove the punctuation and/or section boundaries when editing.

In some embodiments, either an original or a re-formatted text narrative may be received by fact extraction component 104, which may perform processing to extract one or more medical facts (e.g., clinical facts) from the text narrative. The text narrative may be received from ASR engine 102, from medical transcriptionist 130, directly from clinician 120 via user interface 110, or in any other suitable way. Any suitable technique(s) for extracting facts from the text narrative may be used, as aspects of the present invention are not limited in this respect. Exemplary techniques for medical fact extraction are described below.

In some embodiments, a fact extraction component may be implemented using techniques such as those described in U.S. Pat. No. 7,493,253, entitled "Conceptual World Representation Natural Language Understanding System and Method," which is incorporated herein by reference in its entirety. Such a fact extraction component may make use of a formal ontology linked to a lexicon of clinical terms. The formal ontology may be implemented as a relational database, or in any other suitable form, and may represent semantic concepts relevant to the medical domain, as well as linguistic concepts related to ways the semantic concepts may be expressed in natural language.

In some embodiments, concepts in a formal ontology used by a fact extraction component may be linked to a lexicon of medical terms and/or codes, such that each medical term and each code is linked to at least one concept in the formal ontology. In some embodiments, the lexicon may include the standard medical terms and/or codes used by the institution in which the fact extraction component is applied. For example, the standard medical terms and/or codes used by an EHR maintained by the institution may be included in the lexicon linked to the fact extraction component's formal ontology. In some embodiments, the lexicon may also include additional medical terms used by the various clinicians within the institution, and/or used by clinicians generally, when describing medical issues in a free-form narration. Such additional medical terms may be linked, along with their corresponding standard medical terms, to the appropriate shared concepts within the formal ontology. For example, the standard term "acute myocardial infarction" as well as other corresponding terms such as "heart attack," "acute MI" and "AMI" may all be linked to the same abstract concept in the formal ontology—a concept representing an interruption of blood supply to the heart. Such linkage of multiple medical terms to the same abstract concept in some embodiments may relieve the clinician of the burden of ensuring that only standard medical terms preferred by the institution appear in the free-form narration. For example, in some embodiments, a clinician may be free to use the abbreviation "AMI" or the colloquial "heart attack" in his free-form narration, and the shared concept linkage may allow the fact extraction component to nevertheless automatically extract a fact corresponding to "acute myocardial infarction."

In some embodiments, a formal ontology used by a fact extraction component may also represent various types of relationships between the concepts represented. One type of relationship between two concepts may be a parent-child relationship, in which the child concept is a more specific version of the parent concept. More formally, in a parent-child relationship, the child concept inherits all necessary properties of the parent concept, while the child concept may have necessary properties that are not shared by the parent concept. For example, "heart failure" may be a parent concept, and "congestive heart failure" may be a child concept of "heart failure." In some embodiments, any other type(s) of relationship useful to the process of medical documentation may also be represented in the formal ontology. For example, one type of relationship may be a symptom relationship. In one example of a symptom relationship, a concept linked to the term "chest pain" may have a relationship of "is-symptom-of" to the concept linked to the term "heart attack." Other types of relationships may include complication relationships, comorbidity relationships, interaction relationships (e.g., among medications), and many others. Any number and type(s) of concept relationships may be included in such a formal ontology, as aspects of the present invention are not limited in this respect.

In some embodiments, automatic extraction of medical facts from a clinician's free-form narration may involve parsing the free-form narration to identify medical terms that are represented in the lexicon of the fact extraction component. Concepts in the formal ontology linked to the medical terms that appear in the free-form narration may then be identified, and concept relationships in the formal ontology may be traced to identify further relevant concepts. Through these relationships, as well as the linguistic knowledge represented in the formal ontology, one or more medical facts may be extracted. For example, if the free-form narration includes the medical term "hypertension" and the linguistic context relates to the patient's past, the fact extraction component may automatically extract a fact indicating that the patient has a history of hypertension. On the other hand, if the free-form narration includes the medical term "hypertension" in a sentence about the patient's mother, the fact extraction component may automatically extract a fact indicating that the patient has a family history of hypertension. In some embodiments, relationships between concepts in the formal ontology may also allow the fact extraction component to automatically extract facts containing medical terms that were not explicitly included in the free-form narration. For example, the medical term "meningitis" can also be described as inflammation in the brain. If the free-form narration includes the terms "inflammation" and "brain" in proximity to each other, then relationships in the formal ontology between concepts linked to the terms "inflammation," "brain" and "meningitis" may allow the fact extraction component to automatically extract a fact corresponding to "meningitis," despite the fact that the term "meningitis" was not stated in the free-form narration.

It should be appreciated that the foregoing descriptions are provided by way of example only, and that any suitable technique(s) for extracting a set of one or more medical facts from a free-form narration may be used, as aspects of the present invention are not limited to any particular fact extraction technique. For instance, it should be appreciated that fact extraction component 104 is not limited to the use of an ontology, as other forms of knowledge representation models, including statistical models and/or rule-based models, may also be used. The knowledge representation model may also be represented as data in any suitable format, and may be stored in any suitable location, such as in a storage medium of system 100 accessible by fact extraction component 104, as aspects of the invention are not limited in this respect. In addition, a knowledge representation model such as an ontology used by fact extraction component 104 may be constructed in any suitable way, as aspects of the invention are not limited in this respect.

For instance, in some embodiments a knowledge representation model may be constructed manually by one or more human developers with access to expert knowledge about medical facts, diagnoses, problems, potential complications, comorbidities, appropriate observations and/or clinical findings, and/or any other relevant information. In other embodiments, a knowledge representation model may be generated automatically, for example through statistical analysis of past medical reports documenting patient encounters, of medical literature and/or of other medical documents. Thus, in some embodiments, fact extraction component 104 may have access to a data set 170 of medical literature and/or other documents such as past patient encounter reports. In some embodiments, past reports and/or other text documents may be marked up (e.g., by a human) with labels indicating the nature of the relevance of particular statements in the text to the patient encounter or medical topic to which the text relates. A statistical knowledge representation model may then be trained to form associations based on the prevalence of particular labels corresponding to similar text within an aggregate set of multiple marked up documents. For example, if "pneumothorax" is labeled as a "complication" in a large enough proportion of clinical procedure reports documenting pacemaker implantation procedures, a statistical knowledge representation model may generate and store a concept relationship that "pneumothorax is-complication-of pacemaker implantation." In some embodiments, automatically generated and hard coded (e.g., by a human developer) concepts and/or relationships may both be included in a knowledge representation model used by fact extraction component 104.

As discussed above, it should be appreciated that aspects of the invention are not limited to any particular technique(s) for constructing knowledge representation models. Examples of suitable techniques include those disclosed in the following:

Gómez-Pérez, A., and Manzano-Macho, D. (2005). *An overview of methods and tools for ontology learning from texts*. Knowledge Engineering Review 19, p. 187-212.

Cimiano, P., and Staab, S. (2005). *Learning concept hierarchies from text with a guided hierarchical clustering algorithm*. In C. Biemann and G. Paas (eds.), Proceedings of the ICML 2005 Workshop on Learning and Extending Lexical Ontologies with Machine Learning Methods, Bonn, Germany.

Fan, J., Ferrucci, D., Gondek, D., and Kalyanpur, A. (2010). *PRISMATIC: Inducing Knowledge from a Lange Scale Lexicalized Relation Resource*. NAACL Workshop on Formalisms and Methodology for Learning by Reading.

Welty, C., Fan, J., Gondek, D. and Schlaikjer, A. (2010). *Large scale relation detection*. NAACL Workshop on Formalisms and Methodology for Learning by Reading.

Each of the foregoing publications is incorporated herein by reference in its entirety.

Alternatively or additionally, in some embodiments a fact extraction component may make use of one or more statistical models to extract semantic entities from natural language input. In general, a statistical model can be described as a functional component designed and/or trained to analyze new inputs based on probabilistic patterns observed in prior training inputs. In this sense, statistical models differ from "rule-based" models, which typically apply hard-coded deterministic rules to map from inputs having particular characteristics to particular outputs. By contrast, a statistical model may operate to determine a particular output for an input with particular characteristics by considering how often (e.g., with what probability) training inputs with those same characteristics (or similar characteristics) were associated with that particular output in the statistical model's training data. To supply the probabilistic data that allows a statistical model to extrapolate from the tendency of particular input characteristics to be associated with particular outputs in past examples, statistical models are typically trained (or "built") on large training corpuses with great numbers of example inputs. Typically the example inputs are labeled with the known outputs with which they should be associated, usually by a human labeler with expert knowledge of the domain. Characteristics of interest (known as "features") are identified ("extracted") from the inputs, and the statistical model learns the probabilities with which different features are associated with different outputs, based on how often training inputs with those features are associated with those outputs. When the same features are extracted from a new input (e.g., an input that has not been labeled with a known output by a human), the statistical model can then use the learned probabilities for the extracted features (as learned from the training data) to determine which output is most likely correct for the new input. Exemplary implementations of a fact extraction component using one or more statistical models are described further below.

In some embodiments, fact extraction component 104 may utilize a statistical fact extraction model based on entity detection and/or tracking techniques, such as those disclosed in: Florian, R., Hassan, H., Ittycheriah, A., Jing, H., Kambhatla, N., Luo, X., Nicolov, N., and Roukos, S. (2004). *A Statistical Model for Multilingual Entity Detection and Tracking*. Proceedings of the Human Language Technologies Conference 2004 (HLT-NAACL '04). This publication is incorporated herein by reference in its entirety.

For example, in some embodiments, a list of fact types of interest for generating medical reports may be defined, e.g., by a developer of fact extraction component 104. Such fact types (also referred to herein as "entity types") may include, for example, problems, disorders (a disorder is a type of problem), diagnoses (a diagnosis may be a disorder that a clinician has identified as a problem for a particular patient), findings (a finding is a type of problem that need not be a disorder), medications, body sites, social history facts, allergies, diagnostic test results, vital signs, procedures, procedure steps, observations, devices, and/or any other suitable medical fact types. It should be appreciated that any suitable list of fact types may be utilized, and may or may not include any of the fact types listed above, as aspects of the invention are not limited in this respect. In some embodiments, spans of text in a set of sample patient encounter reports may be labeled (e.g., by a human) with appropriate fact types from the list. A statistical model may then be trained on the corpus of labeled sample reports to detect and/or track such fact types as semantic entities, using entity detection and/or tracking techniques, examples of which are described below.

For example, in some embodiments, a large number of past free-form narrations created by clinicians may be manually labeled to form a corpus of training data for a statistical entity detection model. As discussed above, in some embodiments, a list of suitable entities may be defined (e.g., by a domain administrator) to include medical fact types that are to be extracted from future clinician narrations. One or more human labelers (e.g., who may have specific knowledge about medical information and typical clinician narration content) may then manually label portions of the training texts with the particular defined entities to which they correspond. For example, given the training text, "Patient is complaining of acute sinusitis," a human labeler may label the text portion "acute sinusitis" with the entity label "Problem." In another example, given the training text, "He has sinusitis, which appears to be chronic," a human labeler may label the text "sinusitis" and "chronic" with a single label indicating that both words together correspond to a "Problem" entity. As should be clear from these examples, the portion of the text labeled as corresponding to a single conceptual entity need not be formed of contiguous words, but may have words split up within the text, having non-entity words in between.

In some embodiments, the labeled corpus of training data may then be processed to build a statistical model trained to detect mentions of the entities labeled in the training data. Each time the same conceptual entity appears in a text, that appearance is referred to as a mention of that entity. For example, consider the text, "Patient has sinusitis. His sinusitis appears to be chronic." In this example, the entity detection model may be trained to identify each appearance of the word "sinusitis" in the text as a separate mention of the same "Problem" entity.

In some embodiments, the process of training a statistical entity detection model on labeled training data may involve a number of steps to analyze each training text and probabilistically associate its characteristics with the corresponding entity labels. In some embodiments, each training text (e.g., free-form clinician narration) may be tokenized to break it down into various levels of syntactic substructure. For example, in some embodiments, a tokenizer module may be implemented to designate spans of the text as representing structural/syntactic units such as document sections, paragraphs, sentences, clauses, phrases, individual tokens, words, sub-word units such as affixes, etc. In some embodiments, individual tokens may often be single words, but some tokens may include a sequence of more than one word that is defined, e.g., in a dictionary, as a token. For example, the term "myocardial infarction" could be defined as a token, although it is a sequence of more than one word. In some embodiments, a token's identity (i.e., the word or sequence of words itself) may be used as a feature of that token. In some embodiments, the token's placement within particular syntactic units in the text (e.g., its section, paragraph, sentence, etc.) may also be used as features of the token.

In some embodiments, an individual token within the training text may be analyzed (e.g., in the context of the surrounding sentence) to determine its part of speech (e.g., noun, verb, adjective, adverb, preposition, etc.), and the token's part of speech may be used as a further feature of that token. In some embodiments, each token may be tagged with its part of speech, while in other embodiments, not every token may be tagged with a part of speech. In some embodiments, a list of relevant parts of speech may be pre-defined, e.g., by a developer of the statistical model, and any token having a part of speech listed as relevant may be tagged with that part of speech. In some embodiments, a parser module may be implemented to determine the syntactic structure of sentences in the text, and to designate positions within the sentence structure as features of individual tokens. For example, in some embodiments, the fact that a token is part of a noun phrase or a verb phrase may be used as a feature of that token. Any type of parser may be used, non-limiting examples of which include a bottom-up parser and/or a dependency parser, as aspects of the invention are not limited in this respect.

In some embodiments, section membership may be used as a feature of a token. In some embodiments, a section normalization module may be implemented to associate various portions of the narrative text with the proper section to which it should belong. In some embodiments, a set of standardized section types (e.g., identified by their section headings) may be defined for all texts, or a different set of normalized section headings may be defined for each of a number of different types of texts (e.g., corresponding to different types of documents). For example, in some embodiments, a different set of normalized section headings may be defined for each type of medical document in a defined set of medical document types. Non-limiting examples of medical document types include consultation reports, history & physical reports, discharge summaries, and emergency room reports, although there are also many other examples. In the medical field, the various types of medical documents are often referred to as "work types." In some cases, the standard set of sections for various types of medical documents may be established by a suitable system standard, institutional standard, or more widely applicable standard, such as the Meaningful Use standard (discussed above) or the Logical Observation Identifiers Names and Codes (LOINC) standard maintained by the Regenstrief Institute. For example, an expected set of section headings for a history & physical report under the Meaningful Use standard may include headings for a "Reason for Visit" section, a "History of Present Illness" section, a "History of Medication Use" section, an "Allergies, Adverse Reactions and Alerts" section, a "Review of Systems" section, a "Social History" section, a "Physical Findings" section, an "Assessment and Plan" section, and/or any other suitable section(s). Any suitable set of sections may be used, however, as aspects of the invention are not limited in this respect.

A section normalization module may use any suitable technique to associate portions of text with normalized document sections, as aspects of the invention are not limited in this respect. In some embodiments, the section normalization module may use a table (e.g., stored as data in a storage medium) to map text phrases that commonly occur in medical documents to the sections to which they should belong. In another example, a statistical model may be trained to determine the most likely section for a portion of text based on its semantic content, the semantic content of surrounding text portions, and/or the expected semantic content of the set of normalized sections. In some embodiments, once a normalized section for a portion of text has been identified, the membership in that section may be used as a feature of one or more tokens in that portion of text.

In some embodiments, other types of features may be extracted, i.e., identified and associated with tokens in the training text. For example, in some embodiments, an N-gram feature may identify the previous (N−1) words and/or tokens in the text as a feature of the current token. In another example, affixes (e.g., suffixes such as—ectomy, -oma, -itis, etc.) may be used as features of tokens. In another example, one or more predefined dictionaries and/or ontologies may be accessed, and a token's membership in any of those dictionaries may be used as a feature of that token. For example, a predefined dictionary of surgical procedures may be accessed, and/or a dictionary of body sites, and/or a dictionary of known diseases, etc. It should be appreciated, however, that all of the foregoing feature types are merely examples, and any suitable number and/or types of features of interest may be designated, e.g., by a developer of the statistical entity detection model, as aspects of the invention are not limited in this respect.

In some embodiments, the corpus of training text with its hand-labeled fact type entity labels, along with the collection of features extracted for tokens in the text, may be input to the statistical entity detection model for training. As discussed above, examples of suitable features include position within document structure, syntactic structure, parts of speech, parser features, N-gram features, affixes (e.g., prefixes and/or suffixes), membership in dictionaries (sometimes referred to as "gazetteers") and/or ontologies, surrounding token contexts (e.g., a certain number of tokens to the left and/or right of the current token), orthographic features (e.g., capitalization, letters vs. numbers, etc.), entity labels assigned to previous tokens in the text, etc. As one non-limiting example, consider the training sentence, "Patient is complaining of acute sinusitis," for which the word sequence "acute sinusitis" was hand-labeled as being a "Problem" entity. In one exemplary implementation, features extracted for the token "sinusitis" may include the token identity feature that the word is "sinusitis," a syntactic feature specifying that the token occurred at the end of a sentence (e.g., followed by a period), a part-of-speech feature of "noun," a parser feature that the token is part of a noun phrase ("acute sinusitis"), a trigram feature that the two preceding words are "of acute," an affix feature of "-itis," and a dictionary feature that the token is a member of a predefined dictionary of types of inflammation. It should be appreciated, however, that the foregoing list of features is merely exemplary, as any suitable features may be used. Aspects of the invention are not limited to any of the features listed above, and implementations including some, all, or none of the above features, as well as implementations including features not listed above, are possible.

In some embodiments, given the extracted features and manual entity labels for the entire training corpus as input, the statistical entity detection model may be trained to be able to probabilistically label new texts (e.g., texts not included in the training corpus) with automatic entity labels using the same feature extraction technique that was applied to the training corpus. In other words, by processing the input features and manual entity labels of the training corpus, the statistical model may learn probabilistic relationships between the features and the entity labels. When later presented with an input text without manual entity labels, the statistical model may then apply the same feature extraction techniques to extract features from the input text, and may apply the learned probabilistic relationships to automatically determine the most likely entity labels for word sequences in the input text. Any suitable statistical modeling technique may be used to learn such probabilistic relationships, as aspects of the invention are not limited in this respect. Non-limiting examples of suitable known statistical modeling techniques include machine learning techniques such as maximum entropy modeling, support vector machines, and conditional random fields, among others.

In some embodiments, training the statistical entity detection model may involve learning, for each extracted feature, a probability with which tokens having that feature are associated with each entity type. For example, for the suffix feature "-itis," the trained statistical entity detection model may store a probability p1 that a token with that feature should be labeled as being part of a "Problem" entity, a probability p2 that a token with that feature should be labeled as being part of a "Medication" entity, etc. In some embodiments, such probabilities may be learned by determining the frequency with which tokens having the "-itis" feature were hand-labeled with each different entity label in the training corpus. In some embodiments, the probabilities may be normalized such that, for each feature, the probabilities of being associated with each possible entity (fact type) may sum to 1. However, aspects of the invention are not limited to such normalization. In some embodiments, each feature may also have a probability p0 of not being associated with any fact type, such that the non-entity probability p0 plus the probabilities of being associated with each possible fact type sum to 1 for a given feature. In other embodiments, separate classifiers may be trained for each fact type, and the classifiers may be run in parallel. For example, the "-itis" feature may have probability p1 of being part of a "Problem" entity and probability (1−p1) of not being part of a "Problem" entity, probability p2 of being part of a "Medication" entity and probability (1−p2) of not being part of a "Medication" entity, and so on. In some embodiments, training separate classifiers may allow some word sequences to have a non-zero probability of being labeled with more than one fact type simultaneously; for example, "kidney failure" could be labeled as representing both a Body Site and a Problem. In some embodiments, classifiers may be trained to identify sub-portions of an entity label. For example, the feature "-itis" could have a probability $p_B$ of its token being at the beginning of a "Problem" entity label, a probability $p_I$ of its token being inside a "Problem" entity label (but not at the beginning of the label), and a probability $p_O$ of its token being outside a "Problem" entity label (i.e., of its token not being part of a "Problem" entity).

In some embodiments, the statistical entity detection model may be further trained to weight the individual features of a token to determine an overall probability that it should be associated with a particular entity label. For example, if the token "sinusitis" has n extracted features f1 . . . fn having respective probabilities p1 . . . pn of being associated with a "Problem" entity label, the statistical model may be trained to apply respective weights w1 . . . wn to the feature probabilities, and then combine the weighted feature probabilities in any suitable way to determine the overall probability that "sinusitis" should be part of a "Problem" entity. Any suitable technique for determining such weights may be used, including known modeling techniques such as maximum entropy modeling, support vector machines, conditional random fields, and/or others, as aspects of the invention are not limited in this respect.

In some embodiments, when an unlabeled text is input to the trained statistical entity detection model, the model may process the text to extract features and determine probabilities for individual tokens of being associated with various entity (e.g., fact type) labels. In some embodiments, the most probable label (including the non-entity label, if it is most probable) may be selected for each token in the input text. In other embodiments, labels may be selected through more contextual analysis, such as at the phrase level or sentence level, rather than at the token level. Any suitable technique, such as Viterbi techniques, or any other suitable technique, may be used, as aspects of the invention are not limited in this respect. In some embodiments, a lattice may be constructed of the associated probabilities for all entity types for all tokens in a sentence, and the best (e.g., highest combined probability) path through the lattice may be selected to determine which word sequences in the sentence are to be automatically labeled with which entity (e.g., fact type) labels. In some embodiments, not only the best path may be identified, but also the (N−1)-best alternative paths with the next highest associated probabilities. In some embodiments, this may result in an N-best list of alternative hypotheses for fact type labels to be associated with the same input text.

In some embodiments, a statistical model may also be trained to associate fact types extracted from new reports with particular facts to be extracted from those reports (e.g., to determine a particular concept represented by the text portion that has been labeled as an entity mention). For example, in some embodiments, a statistical fact extraction model may be applied to automatically label "acute sinusitis" not only with the "Problem" entity (fact type) label, but also with a label indicating the particular medical fact (e.g., concept) indicated by the word sequence (e.g., the medical fact "sinusitis, acute"). In such embodiments, for example, a single statistical model may be trained to detect specific particular facts as individual entities. For example, in some embodiments, the corpus of training text may be manually labeled by one or more human annotators with labels indicating specific medical facts, rather than labels indicating more general entities such as fact types or categories. However, in other embodiments, the process of detecting fact types as entities may be separated from the process of relating detected fact types to particular facts. For example, in some embodiments, a separate statistical model (e.g., an entity detection model) may be trained to automatically label portions of text with fact type labels, and another separate statistical model (e.g., a relation model) may be trained to identify which labeled entity (fact type) mentions together indicate a single specific medical fact. In some cases, the relation model may identify particular medical facts by relating together two or more mentions labeled with the same entity type.

For example, in the text, "Patient is complaining of acute sinusitis," in some embodiments an entity detection model may label the tokens "acute" and "sinusitis" as being part of a "Problem" entity. In some embodiments, a relation model, given that "acute" and "sinusitis" have been labeled as "Problem," may then relate the two tokens together to a single medical fact of "sinusitis, acute." For another example, consider the text, "Patient has sinusitis, which appears to be chronic." In some embodiments, an entity detection model may be applied to label the tokens "sinusitis" and "chronic" as "Problem" entity mentions. In some embodiments, a relation model may then be applied to determine that the two "Problem" entity mentions "sinusitis" and "chronic" are related (even though they are not contiguous in the text) to represent a single medical fact of "sinusitis, chronic." For yet another example, consider the text, "She has acute sinusitis; chronic attacks of asthma may be a factor." In some embodiments, an entity detection model may label each of the tokens "acute," "sinusitis," "chronic," and "asthma" as belonging to "Problem" entity mentions. In some embodiments, a relation model may then be applied to determine which mentions relate to the same medical fact. For example, the relation model may determine that the tokens "acute" and "sinusitis" relate to a first medical fact (e.g., "sinusitis, acute"), while the tokens "chronic" and "asthma" relate to a different medical fact (e.g., "asthma, chronic"), even though the token "chronic" is closer in the sentence to the token "sinusitis" than to the token "asthma."

In some embodiments, a relation model may be trained statistically using methods similar to those described above for training the statistical entity detection model. For example, in some embodiments, training texts may be manually labeled with various types of relations between entity mentions and/or tokens within entity mentions. For example, in the training text, "Patient has sinusitis, which appears to be chronic," a human annotator may label the "Problem" mention "chronic" as having a relation to the "Problem" mention "sinusitis," since both mentions refer to the same medical fact. In some embodiments, the relation annotations may simply indicate that certain mentions are related to each other, without specifying any particular type of relationship. In other embodiments, relation annotations may also indicate specific types of relations between entity mentions. Any suitable number and/or types of relation annotations may be used, as aspects of the invention are not limited in this respect. For example, in some embodiments, one type of relation annotation may be a "split" relation label. The tokens "sinusitis" and "chronic," for example, may be labeled as having a split relationship, because "sinusitis" and "chronic" together make up an entity, even though they are not contiguous within the text. In this case, "sinusitis" and "chronic" together indicate a specific type of sinusitis fact, i.e., one that it is chronic and not, e.g., acute. Another exemplary type of relation may be an "attribute" relation. In some embodiments, one or more system developers may define sets of attributes for particular fact types, corresponding to related information that may be specified for a fact type. For example, a "Medication" fact type may have attributes "dosage," "route," "frequency," "duration," etc. In another example, an "Allergy" fact type may have attributes "allergen," "reaction," "severity," etc. It should be appreciated, however, that the foregoing are merely examples, and that aspects of the invention are not limited to any particular attributes for any particular fact types. Also, other types of fact relations are possible, including family relative relations, causes-problem relations, improves-problem relations, and many others. Aspects of the invention are not limited to use of any particular relation types.

In some embodiments, using techniques similar to those described above, the labeled training text may be used as input to train the statistical relation model by extracting features from the text, and probabilistically associating the extracted features with the manually supplied labels. Any suitable set of features may be used, as aspects of the invention are not limited in this respect. For example, in some embodiments, features used by a statistical relation model may include entity (e.g., fact type) labels, parts of speech, parser features, N-gram features, token window size (e.g., a count of the number of words or tokens present between two tokens that are being related to each other), and/or any other suitable features. It should be appreciated, however, that the foregoing features are merely exemplary, as embodiments are not limited to any particular list of features. In some embodiments, rather than outputting only the best (e.g., most probable) hypothesis for relations between entity mentions, a statistical relation model may output a list of multiple alternative hypotheses, e.g., with corresponding probabilities, of how the entity mentions labeled in the input text are related to each other. In yet other embodiments, a relation model may be hard-coded and/or otherwise rule-based, while the entity detection model used to label text portions with fact types may be trained statistically.

In some embodiments, the relation model or another statistical model may also be trained to track mentions of the same entity from different sentences and/or document sections and to relate them together. Exemplary techniques for entity tracking are described in the publication by Florian cited above.

In some embodiments, further processing may be applied to normalize particular facts extracted from the text to standard forms and/or codes in which they are to be documented. For example, medical personnel often have many different ways of phrasing the same medical fact, and a normalization/coding process in some embodiments may be applied to identify the standard form and/or code corresponding to each extracted medical fact that was stated in a non-standard way. The standard form and/or code may be derived from any suitable source, as aspects of the invention are not limited in this respect. Some standard terms and/or codes may be derived from a government or profession-wide standard, such as SNOMED (Systematized Nomenclature of Medicine), UMLS (Unified Medical Language System), RxNorm, RadLex, etc. Other standard terms and/or codes may be more locally derived, such as from standard practices of a particular locality or institution. Still other standard terms and/or codes may be specific to the documentation system including the fact extraction component being applied.

For example, given the input text, "His sinuses are constantly inflamed," in some embodiments, an entity detection model together with a relation model (or a single model performing both functions) may identify the tokens "sinuses," "constantly" and "inflamed" as representing a medical fact. In some embodiments, a normalization/coding process may then be applied to identify the standard form for documenting "constantly inflamed sinuses" as "sinusitis, chronic." Alternatively or additionally, in some embodiments the normalization/coding process may identify a standard code used to document the identified fact. For example, the ICD-9 code for "sinusitis, chronic" is ICD-9 code #473. Any suitable coding system may be used, as aspects of the invention are not limited in this respect. Exemplary standard codes include ICD (International Classification of Diseases) codes, CPT (Current Procedural Terminology) codes, E&M (Evaluation and Management) codes, MedDRA (Medical Dictionary for Regulatory Activities) codes, SNOMED codes, LOINC (Logical Observation Identifiers Names and Codes) codes, RxNorm codes, NDC (National Drug Code) codes and RadLex codes.

In some embodiments, a normalization/coding process may be rule-based (e.g., using lists of possible ways of phrasing particular medical facts, and/or using an ontology of medical terms and/or other language units to normalize facts extracted from input text to their standard forms). For example, in some embodiments, the tokens identified in the text as corresponding to a medical fact may be matched to corresponding terms in an ontology. In some embodiments, a list of closest matching terms may be generated, and may be ranked by their similarity to the tokens in the text. The similarity may be scored in any suitable way. For example, in one suitable technique, one or more tokens in the text may be considered as a vector of its component elements, such as words, and each of the terms in the ontology may also be considered as a vector of component elements such as words. Similarity scores between the tokens may then be computed by comparing the corresponding vectors, e.g., by calculating the angle between the vectors, or a related measurement such as the cosine of the angle. In some embodiments, one or more concepts that are linked in the ontology to one or more of the higher ranking terms (e.g., the terms most similar to the identified tokens in the text) may then be identified as hypotheses for the medical fact to be extracted from that portion of the text. Exemplary techniques that may be used in some embodiments are described in Salton, Wong, & Yang: "A vector space model for automatic indexing," *Communications of the ACM*, November 1975. This publication is incorporated herein by reference in its entirety. However, these are merely examples, and any suitable technique(s) for normalizing entity tokens to standard terms may be utilized in some embodiments, as aspects of the invention are not limited in this respect.

In some embodiments, the normalization/coding process may output a single hypothesis for the standard form and/or code corresponding to each extracted fact. For example, the single output hypothesis may correspond to the concept linked in the ontology to the term that is most similar to the token(s) in the text from which the fact is extracted. However, in other embodiments, the normalization/coding process may output multiple alternative hypotheses, e.g., with corresponding probabilities, for the standard form and/or code corresponding to an individual extracted fact. Thus, it should be appreciated that in some embodiments multiple alternative hypotheses for a medical fact to be extracted from a portion of input text may be identified by fact extraction component 104. Such alternative hypotheses may be collected at any or all of various processing levels of fact extraction, including entity detection, entity relation, and/or normalization/coding stages. In some embodiments, the list of alternative hypotheses may be thresholded at any of the various levels, such that the final list output by fact extraction component 104 may represent the N-best alternative hypotheses for a particular medical fact to be extracted.

It should be appreciated that the foregoing are merely examples, and that fact extraction component 104 may be implemented in any suitable way and/or form, as aspects of the invention are not limited in this respect.

In some embodiments, a user such as clinician 120 may monitor, control and/or otherwise interact with the fact extraction and/or fact review process through a user interface provided in connection with system 100. For example, in some embodiments, user interface 140 may be provided by fact review component 106, e.g., through execution (e.g., by one or more processors of system 100) of programming instructions incorporated in fact review component 106. One exemplary implementation of such a user interface is graphical user interface (GUI) 200, illustrated in FIG. 2. In some embodiments, when the user is clinician 120, GUI 200 may be presented via user interface 110. In some embodiments, a user may be a person other than a clinician; for example, another person such as coding specialist 150 may be presented with GUI 200 via user interface 140. However, it should be appreciated that "user," as used herein, refers to an end user of system 100, as opposed to a software and/or hardware developer of any component of system 100.

The user interface is not limited to a graphical user interface, as other ways of providing data from system 100 to users may be used. For example, in some embodiments, audio indicators may be transmitted from system 100 and conveyed to a user. It should be appreciated that any type of user interface may be provided in connection with fact extraction, fact review and/or other related processes, as aspects of the invention are not limited in this respect. While the exemplary embodiments illustrated in FIG. 1 involve data processing at system 100 and data communication between system 100 and user interfaces 110 and/or 140, it should be appreciated that in other embodiments any or all processing components of system 100 may instead be implemented locally at user interface 110 and/or user interface 140, as aspects of the invention are not limited to any particular distribution of local and/or remote processing capabilities.

As depicted in FIG. 2, GUI 200 includes a number of separate panes displaying different types of data. Identifying information pane 210 includes general information identifying patient 222 as a male patient named John Doe. Such general patient identifying information may be entered by clinician 120, or by other user 150, or may be automatically populated from an electronic medical record for patient 122, or may be obtained from any other suitable source. Identifying information pane 210 also displays the creation date and document type of the report currently being worked on. This information may also be obtained from any suitable source, such as from stored data or by manual entry. When referring herein to entry of data by clinician 120 and/or other user 150, it should be appreciated that any suitable form of data entry may be used, including input via mouse, keyboard, touchscreen, stylus, voice, or any other suitable input form, as aspects of the invention are not limited in this respect.

GUI 200 as depicted in FIG. 2 includes a text panel 220 in which a text narrative referring to the encounter between clinician 120 and patient 122 is displayed. In some embodiments, text panel 220 may include text editor functionality, such that clinician 120 may directly enter the text narrative into text panel 220, either during the patient encounter or at some time thereafter. If ASR is used to produce the text narrative from a spoken dictation provided by clinician 120, in some embodiments the text may be displayed in text panel 220 as it is produced by ASR engine 102, either in real time while clinician 120 is dictating, or with a larger processing delay. In other embodiments, the text narrative may be received as stored data from another source, such as from medical transcriptionist 130, and may be displayed in completed form in text panel 220. In some embodiments, the text narrative may then be edited if desired by clinician 120 and/or other user 150 within text panel 220. However, text editing capability is not required, and in some embodiments text panel 220 may simply display the text narrative without providing the ability to edit it.

Exemplary GUI 200 further includes a fact panel 230 in which one or more medical facts, once extracted from the text narrative and/or entered in another suitable way, may be displayed as discrete structured data items. When clinician 120 and/or other user 150 is ready to direct fact extraction component 104 to extract one or more medical facts from the text narrative, in some embodiments he or she may select process button 240 via any suitable selection input method. However, a user indication to begin fact extraction is not limited to a button such as process button 240, as any suitable way to make such an indication may be provided by GUI 200. In some embodiments, no user indication to begin fact extraction may be required, and fact extraction component 104 may begin a fact extraction process as soon as a requisite amount of text (e.g., enough text for fact extraction component 104 to identify one or more clinical facts that can be ascertained therefrom) is entered and/or received. In some embodiments, a user may select process button 240 to cause fact extraction to be performed before the text narrative is complete. For example, clinician 120 may dictate, enter via manual input and/or otherwise provide a part of the text narrative, select process button 240 to have one or more facts extracted from that part of the text narrative, and then continue to provide further part(s) of the text narrative. In another example, clinician 120 may provide all or part of the text narrative, select process button 240 and review the resulting extracted facts, edit the text narrative within text pane 220, and then select process button 240 again to review how the extracted facts may change.

Figure 3A:
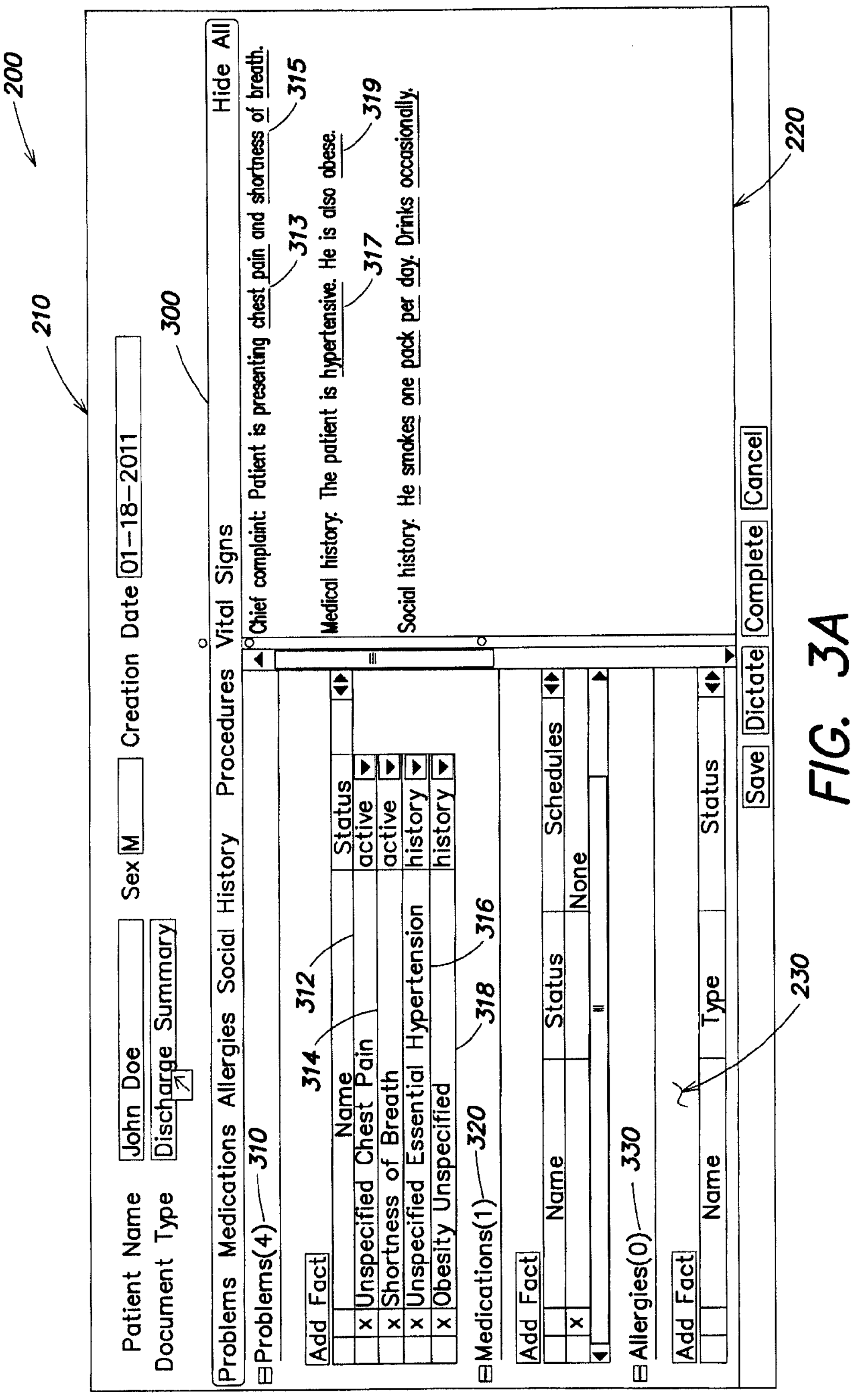

In some embodiments, one or more medical facts extracted from the text narrative by fact extraction component 104 may be displayed to the user via GUI 200 in fact panel 230. Screenshots illustrating an example display of medical facts extracted from an example text narrative are provided in FIGS. 3A and 3B. FIG. 3A is a screenshot with fact panel 230 scrolled to the top of a display listing medical facts extracted from the example text narrative, and FIG. 3B is a screenshot with fact panel 230 scrolled to the bottom of the display listing the extracted medical facts. In some embodiments, as depicted in FIGS. 3A and 3B, medical facts corresponding to a patient encounter may be displayed in fact panel 230, and organized into a number of separate categories of types of facts. An exemplary set of medical fact categories includes categories for problems, medications, allergies, social history, procedures and vital signs. However, it should be appreciated that any suitable fact categories may be used, as aspects of the invention are not limited in this respect. In addition, organization of facts into categories is not required, and displays without such organization are possible. As depicted in FIGS. 3A and 3B, in some embodiments GUI 200 may be configured to provide a navigation panel 300, with a selectable indication of each fact category available in the display of fact panel 230. In some embodiments, when the user selects one of the categories within navigation panel 300 (e.g., by clicking on it with a mouse, touchpad, stylus, or other input device), fact panel 230 may be scrolled to display the corresponding fact category. As depicted in FIGS. 3A and 3B, all available fact categories for the current document type are displayed, even if a particular fact category includes no extracted or otherwise entered medical facts. However, this is not required; in some embodiments, only those fact categories having facts ascertained from the patient encounter may be displayed in fact panel 230.

Fact panel 230 scrolled to the top of the display as depicted in FIG. 3A shows problem fact category 310, medications fact category 320, and allergies fact category 330. Within problem fact category 310, four clinical facts have been extracted from the example text narrative; no clinical facts have been extracted in medications fact category 320 or in allergies fact category 330. Within problem fact category 310, fact 312 indicates that patient 122 is currently presenting with unspecified chest pain; that the chest pain is a currently presenting condition is indicated by the status "active." Fact 314 indicates that patient 122 is currently presenting with shortness of breath. Fact 316 indicates that the patient has a history (status "history") of unspecified essential hypertension. Fact 318 indicates that the patient has a history of unspecified obesity. As illustrated in FIG. 3A, each clinical fact in problem fact category 310 has a name field and a status field. In some embodiments, each field of a clinical fact may be a structured component of that fact represented as a discrete structured data item. In this example, the name field may be structured such that only a standard set of medical terms for problems may be available to populate that field. For example, the status field may be structured such that only statuses in the Systematized Nomenclature of Medicine (SNOMED) standard (e.g., "active" and "history") may be selected within that field, although other standards (or no standard) could be employed. An exemplary list of fact categories and their component fields is given below. However, it should be appreciated that this list is provided by way of example only, as aspects of the invention are not limited to any particular organizational system for facts, fact categories and/or fact components.

Exemplary List of Fact Categories and Component Fields

Category: Problems. Fields: Name, SNOMED status, ICD code.

Category: Medications. Fields: Name, Status, Dose form, Frequency, Measures, RxNorm code, Administration condition, Application duration, Dose route.

Category: Allergies. Fields: Allergen name, Type, Status, SNOMED code, Allergic reaction, Allergen RxNorm.

Category: Social history—Tobacco use. Fields: Name, Substance, Form, Status, Qualifier, Frequency, Duration, Quantity, Unit type, Duration measure, Occurrence, SNOMED code, Norm value, Value.

Category: Social history—Alcohol use. Fields: Name, Substance, Form, Status, Qualifier, Frequency, Duration, Quantity, Quantifier, Unit type, Duration measure, Occurrence, SNOMED code, Norm value, Value.

Category: Procedures. Fields: Name, Date, SNOMED code.

Category: Vital signs. Fields: Name, Measure, Unit, Unit type, Date/Time, SNOMED code, Norm value, Value.

In some embodiments, a linkage may be maintained between one or more medical facts extracted by fact extraction component 104 and the portion(s) of the text narrative from which they were extracted. As discussed above, such a portion of the text narrative may consist of a single word or may include multiple words, which may be in a contiguous sequence or may be separated from each other by one or more intervening words, sentence boundaries, section boundaries, or the like. For example, fact 312 indicating that patient 122 is currently presenting with unspecified chest pain may have been extracted by fact extraction component 104 from the words "chest pain" in the text narrative. The "active" status of extracted fact 312 may have been determined by fact extraction component 104 based on the appearance of the words "chest pain" in the section of the text narrative with the section heading "Chief complaint." In some embodiments, fact extraction component 104 and/or another processing component may be programmed to maintain (e.g., by storing appropriate data) a linkage between an extracted fact (e.g., fact 312) and the corresponding text portion (e.g., "chest pain").

In some embodiments, GUI 200 may be configured to provide visual indicators of the linkage between one or more facts displayed in fact panel 230 and the corresponding portion(s) of the text narrative in text panel 220 from which they were extracted. In the example depicted in FIG. 3A, the visual indicators are graphical indicators consisting of lines placed under the appropriate portions of the text narrative in text panel 220. Indicator 313 indicates the linkage between fact 312 and the words "chest pain" in the "Chief complaint" section of the text narrative; indicator 315 indicates the linkage between fact 314 and the words "shortness of breath" in the "Chief complaint" section of the text narrative; indicator 317 indicates the linkage between fact 316 and the word "hypertensive" in the "Medical history" section of the text narrative; and indicator 319 indicates the linkage between fact 318 and the word "obese" in the "Medical history" section of the text narrative. However, these are merely examples of one way in which visual indicators may be provided, as other types of visual indicators may be provided. For example, different or additional types of graphical indicators may be provided, and/or linked text in text panel 220 may be displayed in a distinctive textual style (e.g., font, size, color, formatting, etc.). Aspects of the invention are not limited to any particular type of linkage indicator.

In some embodiments, when the textual representation of the free-form narration provided by clinician 120 has been re-formatted and fact extraction has been performed with reference to the re-formatted version, the original version may nevertheless be displayed in text panel 220, and linkages may be maintained and/or displayed with respect to the original version. For example, in some embodiments, each extracted clinical fact may be extracted by fact extraction component 104 from a corresponding portion of the re-formatted text, but that portion of the re-formatted text may have a corresponding portion of the original text of which it is a formatted version. A linkage may therefore be maintained between that portion of the original text and the extracted fact, despite the fact actually having been extracted from the re-formatted text. In some embodiments, providing an indicator of the linkage between the extracted fact and the original text may allow clinician 120 and/or other user 150 to appreciate how the extracted fact is related to what was actually said in the free-form narration. However, other embodiments may maintain linkages between extracted facts and the re-formatted text, as an alternative or in addition to the linkages between the extracted facts and the original text, as aspects of the invention are not limited in this respect.

Fact panel 230 scrolled to the bottom of the display as depicted in FIG. 3B shows social history fact category 340, procedures fact category 350, and vital signs fact category 360. Within social history fact category 340, two clinical facts have been extracted; no facts have been extracted in procedures fact category 350 and vital signs fact category 360. Within social history fact category 340, fact 342 indicates that patient 122 currently smokes cigarettes with a frequency of one pack per day. Fact 344 indicates that patient 122 currently occasionally drinks alcohol. Indicator 343 indicates that fact 342 was extracted from the words "He smokes one pack per day" in the "Social history" section of the text narrative; and indicator 345 indicates that fact 344 was extracted from the words "Drinks occasionally" in the "Social history" section of the text narrative. In some embodiments, visual indicators such as indicators 343 and 345 may be of a different textual and/or graphical style or of a different indicator type than visual indicators such as indicators 313, 315, 317 and 319, to indicate that they correspond to a different fact category. For example, in some embodiments indicators 343 and 345 corresponding to social history fact category 340 may be displayed in a different color than indicators 313, 315, 317 and 319 corresponding to problems fact category 310. In some embodiments, linkages for different individual facts may be displayed in different textual and/or graphical styles or indicator types to allow the user to easily appreciate which fact corresponds to which portion of the text narrative. For example, in some embodiments indicator 343 may be displayed in a different color than indicator 345 because they correspond to different facts, even though both correspond to the same fact category.

Figure 4:
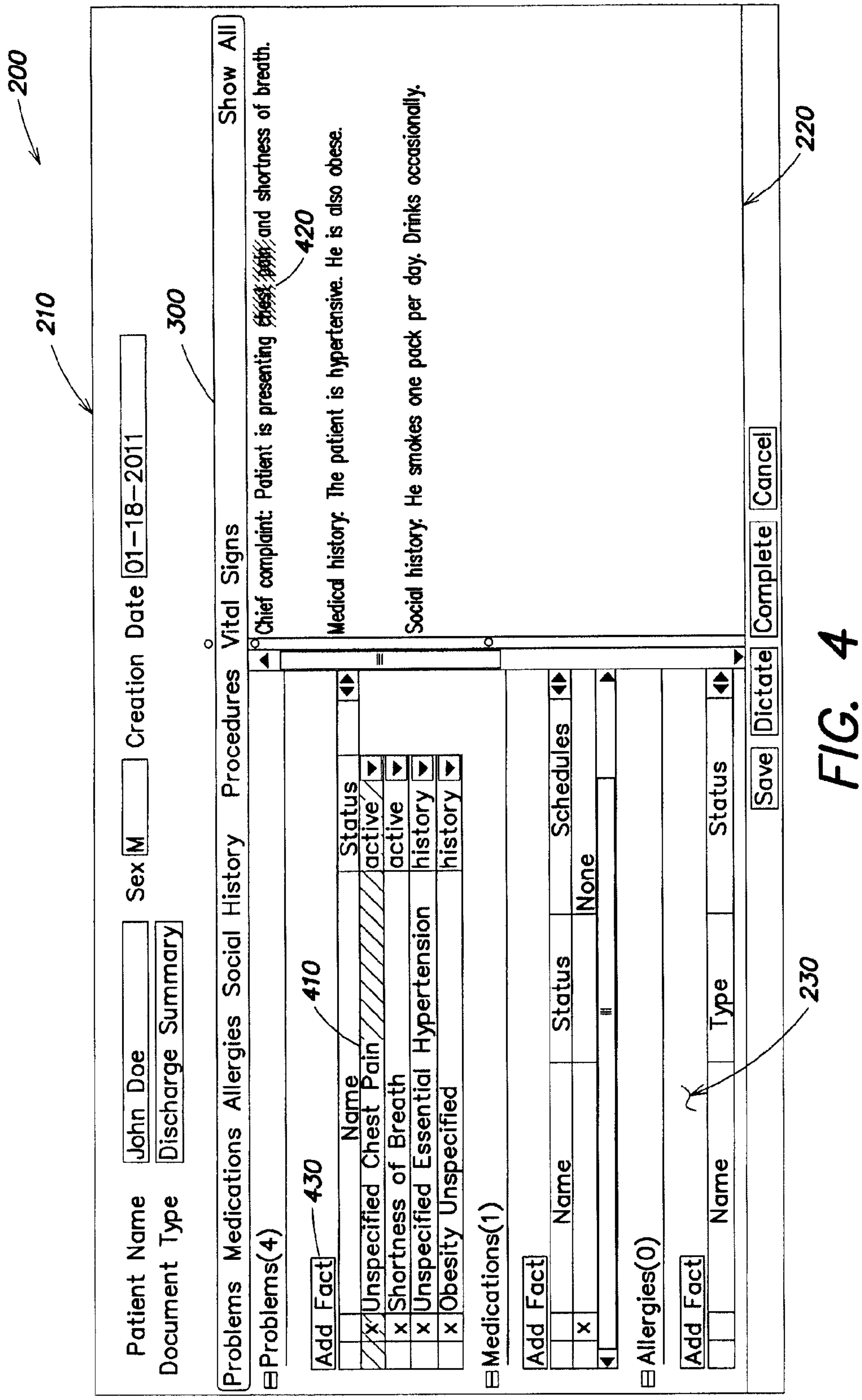
FIG. 4 is a screenshot illustrating an exemplary display of linkage between text and a clinical fact in accordance with some embodiments of the present invention.

In some embodiments, GUI 200 may be configured to allow the user to select one or more of the medical facts in fact panel 230, and in response to the selection, to provide an indication of the portion(s) of the text narrative from which those fact(s) were extracted. An example is illustrated in FIG. 4. In this example, fact 312 ("unspecified chest pain") has been selected by the user in fact panel 230, and in response visual indicator 420 of the portion of the text narrative from which fact 312 was extracted ("chest pain") is provided. Such a user selection may be made in any suitable way, as aspects of the invention are not limited in this respect. Examples include using an input device (e.g., mouse, keyboard, touchpad, stylus, etc.) to click on or otherwise select fact 312, hovering the mouse or other input mechanism above or nearby to fact 312, speaking a selection of fact 312 through voice, and/or any other suitable selection method. Similarly, in some embodiments GUI 200 may be configured to visually indicate the corresponding fact in fact panel 230 when the user selects a portion of the text narrative in text panel 220. In some embodiments, a visual indicator may include a line or other graphical connector between a fact and its corresponding portion of the text narrative. Any visual indicator may be provided in any suitable form (examples of which are given above) as aspects of the invention are not limited in this respect. In addition, aspects of the invention are not limited to visual indicators, as other forms of indicators may be provided. For example, in response to a user selection of fact 312, an audio indicator of the text portion "chest pain" may be provided in some embodiments. In some embodiments, the audio indicator may be provided by playing the portion of the audio recording of the clinician's spoken dictation comprising the words "chest pain." In other embodiments, the audio indicator may be provided by playing an audio version of the words "chest pain" generated using automatic speech synthesis. Any suitable form of indicator or technique for providing indicators may be used, as aspects of the invention are not limited in this respect.

In some embodiments, GUI 200 may be configured to present to the user multiple alternative hypotheses for a medical fact to be extracted from the text narrative. This may be done in any suitable way, as aspects of the invention are not limited in this respect. As described above, in some embodiments, alternative hypotheses may be generated by fact extraction component 104 through processing of the text narrative by one or more statistical fact extraction models. In some embodiments, each statistical model or model component applied may generate a list of alternative hypotheses for its output, and fact extraction component 104 may compile an N-best list of all of the combined alternative hypotheses using any suitable thresholding technique. For example, in some embodiments, an entity detection model may generate multiple alternative hypotheses, each of which may be processed by a relation model to generate multiple alternative hypotheses, each of which may be processed by a normalization/coding stage to generate multiple alternative hypotheses, and so on. In other embodiments, not all stages of fact extraction component 104 may output alternative hypotheses, but one or more particular processing stages of fact extraction may be selected (e.g., by one or more developers of fact extraction component 104) to generate alternative hypotheses to be carried through subsequent processing stages. It should be appreciated, however, that the foregoing are merely examples, and any suitable technique for generating multiple alternative hypotheses for a fact to be extracted may be used, as aspects of the invention are not limited in this respect.

In some embodiments, each of the alternative hypotheses output by fact extraction component 104 may represent a different semantic meaning, and only one of the alternative hypotheses may accurately represent the intended semantic meaning of the portion of the text narrative from which the alternative hypotheses were extracted. For example, consider the text, "She has acute sinusitis; chronic attacks of asthma may be a factor." In some embodiments, fact extraction component 104 may output "sinusitis," "sinusitis, acute," and "sinusitis, chronic" as alternative hypotheses for the intended semantic meaning of the text portion "acute sinusitis; chronic." In this case, only "sinusitis, acute" accurately represents the intended semantic meaning of the text. "Sinusitis, chronic" is incorrect because the text was not intended to indicate that the sinusitis is chronic, and "sinusitis" is inaccurate because the text was intended to indicate a more specific fact: that the sinusitis is acute. This example also illustrates that in some embodiments one of the alternative hypotheses may be a parent concept of another of the alternative hypotheses. In this example, "sinusitis" is a parent concept of "sinusitis, acute," as "sinusitis, acute" is a more specific type of "sinusitis." In formal semantic terms, the child concept shares all characteristics of the parent concept, and also has one or more additional characteristics (in this case, that of being "acute").

It should be appreciated that techniques described herein may in many cases provide significantly more functionality than simply identifying keywords in a narrative and mapping those keywords to standard codes such as billing codes (e.g., ICD codes). Extracting underlying semantic meanings (e.g., the medical facts being expressed by the narrative) may in many cases allow for more complex understanding of relationships between narrative expressions and the codes they produce. For example, in many cases, there may not be a simple one-to-one relationship between text and codes, or between extracted facts and codes. In some embodiments, two or more of the alternative hypotheses for a particular medical fact (only one of which may accurately represent the intended semantic meaning of the corresponding text) may correspond to the same billing code. For example, if a set of alternative fact hypotheses included "shoulder bursitis," "right shoulder bursitis," and "severe right shoulder bursitis," all three of those alternative hypotheses (each representing a different fact) would correspond to the same ICD9 billing code 726.10, "Disorders of bursae and tendons in shoulder region, unspecified." In some embodiments, one or more alternative hypotheses may not correspond to any billing code at all. For example, hypotheses for Problem and Procedure fact types may often correspond to billing codes, but hypotheses for other fact types such as Allergy fact types, Social History fact types, Vital Signs fact types, etc., often do not correspond to any billing codes.

In some embodiments, GUI 200 may be configured to provide any of various ways for multiple alternative hypotheses for a medical fact to be presented to the user. Examples are provided below; however, it should be appreciated that any suitable technique or combination of techniques for presenting alternative hypotheses may be used, as aspects of the invention are not limited in this respect. In one example, the user may select (e.g., using any suitable selection technique, examples of which are provided above) a portion of the text narrative in text panel 220, and GUI 200 may be configured to provide a list of alternative hypotheses for the medical fact to be extracted from that portion of the text narrative, e.g., in fact panel 230, in response to the user selection of the portion of the text narrative. In another example, GUI 200 may be configured to initially present one of the alternative hypotheses (e.g., the hypothesis with the greatest calculated likelihood of accurately representing the intended semantic meaning of the portion of the text narrative) in fact panel 230. In response to a user selection of the presented fact hypothesis, GUI 200 may then present a list of the other alternative hypotheses for the selected fact.

In some embodiments, an indicator of the linkage between an individual alternative hypothesis and the portion of text from which it could be extracted may be provided by GUI 200. Exemplary techniques for providing indicators of linkages between facts and text portions are described above. In some embodiments, the linkages may differ between different alternative hypotheses, such that different alternative hypotheses are linked to different tokens or collections of tokens in the text narrative. For instance, in the example given above for the text, "She has acute sinusitis; chronic attacks of asthma may be a factor," the linkage for the hypothesis "sinusitis, acute" may be with the token sequence "acute sinusitis." On the other hand, the linkage for the hypothesis "sinusitis, chronic" may be with the tokens "sinusitis" and "chronic," and the linkage for the hypothesis "sinusitis" may be simply with the token "sinusitis."

In some embodiments, each of the alternative hypotheses presented by GUI 200 may have a corresponding estimated likelihood of accurately representing the intended semantic meaning of the portion of the text narrative from which the fact could be extracted. In some embodiments, the estimated likelihoods may be presented along with the alternative hypotheses by GUI 200. In some embodiments, the list of alternative hypotheses presented by GUI 200 may be ranked according to the estimated likelihoods. In some embodiments, the estimated likelihood of each alternative hypothesis may be determined, e.g., by fact extraction component 104, as part of the probabilistic processing of the text narrative by one or more statistical models, as described in detail above.

When presenting the list of alternative hypotheses via GUI 200, the number of alternative hypotheses to be presented may be determined, e.g., by fact review component 106, in any suitable way, as aspects of the invention are not limited in this respect. In some embodiments, a predetermined number N of alternative hypotheses may always be presented, provided that N alternative hypotheses with non-zero likelihoods exist for a particular medical fact to be extracted. When the number of alternative hypotheses with non-zero likelihoods is less than N, in some embodiments all of the alternative hypotheses may be presented. When the number of alternative hypotheses with non-zero likelihoods is greater than N, in some embodiments the N alternative hypotheses with the greatest likelihoods may be presented to the user. Alternatively or additionally, in some embodiments there may be a threshold likelihood below which an alternative hypothesis will not be presented to the user. In some embodiments, all alternative hypotheses whose likelihoods are greater than the threshold may be presented. In other embodiments, the N-best alternative hypotheses or all alternative hypotheses with likelihoods greater than the threshold, whichever number is smaller, may be presented to the user. The foregoing are merely examples, however, and any suitable technique for determining which alternative hypotheses to present to the user may be used, as aspects of the invention are not limited in this respect.

In some embodiments, GUI 200 may be configured to allow the user, once the list of alternative hypotheses has been presented, to select one of the hypotheses from the list. In response to the user selection, in some embodiments system 100, e.g., via fact review component 106, may designate the selected hypothesis as accurately representing the semantic meaning of the portion of the text from which it was extracted. In some embodiments, this may involve updating the list of facts displayed in fact panel 230 to confirm the selected hypothesis as the finalized extracted fact corresponding to that portion of the text narrative.

In some embodiments, GUI 200 may be configured to provide any of various ways for the user to make one or more changes to the set of medical facts extracted from the text narrative by fact extraction component 104 and displayed in fact panel 230. For example, the user may be allowed to delete a fact from the set in fact panel 230, e.g., by selecting the "X" option appearing next to the fact. In some embodiments, the user may be allowed to edit a fact within fact panel 230. In one example, the user may edit the name field of fact 312 by selecting the fact and typing, speaking or otherwise providing a different name for that fact. As depicted in FIG. 3A and FIG. 4, in some embodiments the user may edit the status field of fact 312 by selecting a different status from the available drop-down menu, although other techniques for allowing editing of the status field are possible. In some embodiments, the user may alternatively or additionally be allowed to edit a fact by interacting with the text narrative in text panel 220. For example, the user may add, delete, or change one or more words in the text narrative, and then the text narrative may be re-processed by fact extraction component 104 to extract an updated set of medical facts. In some embodiments, the user may be allowed to select only a part of the text narrative in text panel 220 (e.g., by highlighting it), and have fact extraction component 104 re-extract facts only from that part, without disturbing facts already extracted from other parts of the text narrative.

Figure 5:
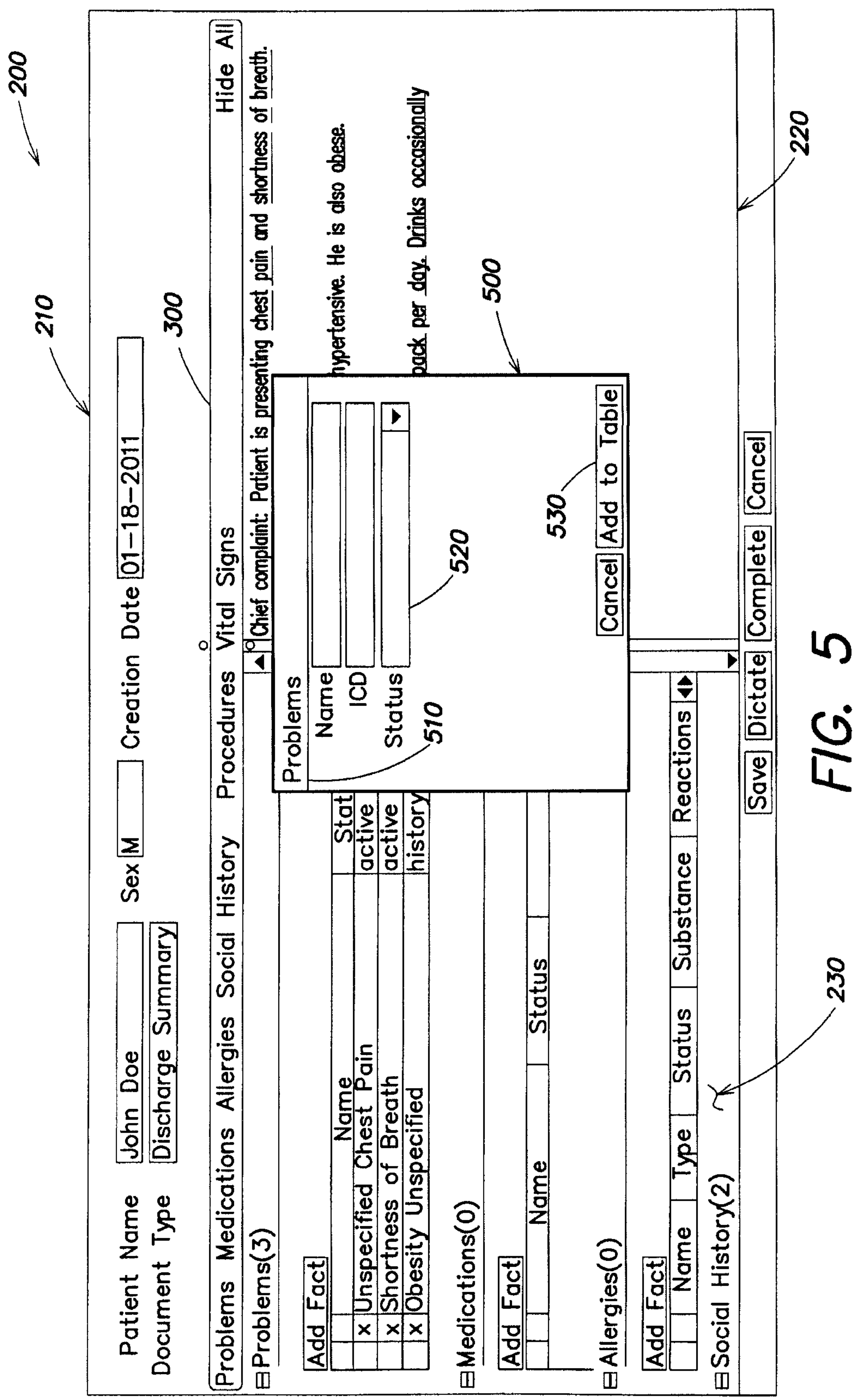
FIG. 5 is a screenshot illustrating an exemplary interface for entering a clinical fact in accordance with some embodiments of the present invention.

In some embodiments, GUI 200 may be configured to provide any of various ways for one or more facts to be added as discrete structured data items. As depicted in FIG. 4, GUI 200 in some embodiments may be configured to provide an add fact button for each fact category appearing in fact panel 230; one such add fact button is add fact button 430. When the user selects add fact button 430, in some embodiments GUI 200 may provide the user with a way to enter information sufficient to populate one or more fields of a new fact in that fact category, for example by displaying pop-up window 500 as depicted in FIG. 5. It should be appreciated that this is merely one example, as aspects of the invention are not limited to the use of pop-up windows or any other particular method for adding a fact. In this example, pop-up window 500 includes a title bar 510 that indicates the fact category ("Problems") to which the new fact will be added. Pop-up window 500 also provides a number of fields 520 in which the user may enter information to define the new fact to be added. Fields 520 may be implemented in any suitable form, including as text entry boxes, drop-down menus, radio buttons and/or checkboxes, as aspects of the invention are not limited to any particular way of receiving input defining a fact. Finally, pop-up window 500 includes add button 530, which the user may select to add the newly defined fact to the set of facts corresponding to the patient encounter, thus entering the fact as a discrete structured data item.

In some embodiments, GUI 200 may alternatively or additionally be configured to allow the user to add a new fact by selecting a (not necessarily contiguous) portion of the text narrative in text panel 220, and indicating that a new fact should be added based on that portion of the text narrative. This may be done in any suitable way. In one example, the user may highlight the desired portion of the text narrative in text panel 220, and right-click on it with a mouse (or perform another suitable input operation), which may cause the designated text to be processed and any relevant facts to be extracted. In other embodiments, the right-click or other input operation may cause a menu to appear. In some embodiments the menu may include options to add the new fact under any of the available fact categories, and the user may select one of the options to indicate which fact category will correspond to the new fact. In some embodiments, an input screen such as pop-up window 500 may then be provided, and the name field may be populated with the words selected by the user from the text narrative. The user may then have the option to further define the fact through one or more of the other available fields, and to add the fact to the set of medical facts for the patient encounter as described above.

As discussed above, in some embodiments when the user makes a correction to the initial set of medical facts automatically extracted from the text narrative, fact review component 106 and/or fact extraction component 104 may learn from the user's correction and may apply it to other texts and/or to other portions of the same text. Any suitable technique(s) may be used for determining which other portions of text are similar enough to the text portion whose extracted fact was corrected by the user to have a similar correction applied to that other portion of text, as aspects of the invention are not limited in this respect. For example, in some embodiments, when the user identifies a fact that should be associated with one portion of the text narrative (e.g., by adding a fact, modifying a fact, or selecting among alternative options for a fact corresponding to that portion of the text narrative), the system may automatically identify features in the corresponding portion of the text to associate with the user's identified fact. Any suitable technique for identifying such features may be used, including any of the feature extraction techniques described above for fact extraction component 104. In some embodiments, the system may then search for one or more other portions of the text that are similar, e.g., because they share the same features (or a suitable subset of those features) as the text portion corresponding to the fact identified by the user. Non-limiting examples of suitable matching features to search for may include matching tokens/words themselves, matching tokens/words in the neighborhood of the token/word being considered (e.g., N-grams to the left and/or right), matching dictionary features, matching regular expressions, and/or matching word clusters or classes. In some embodiments, a statistical model may be trained (e.g., using hand-labeled training data) to apply different weights to different features to determine which particular text portions are similar enough to each other to be considered a match for purposes of propagating user corrections to fact extraction. When a match is found, in some embodiments the system may automatically extract, from the text portion with the matching features, a fact similar to the fact identified by the user for the first portion of the text.

Any suitable technique(s) may be used to automatically apply a user's correction to extract similar facts from other text portions, as aspects of the invention are not limited in this respect. In some embodiments, in response to the user correction, the system may generate one or more rules specifying that a fact of the type corresponding to the user-identified fact should be extracted from text that is similar to the text portion corresponding to the user's correction (e.g., text sharing features with the text portion corresponding to the user's correction). For instance, consider the example given above, in which the user specifies that the fact "myoclonic epileptic seizure" (which is of the "Problem" fact type) should be associated with the text portion "Epileptic myoclonic twitches." In some embodiments, in response to this user correction, the system may identify features of "Epileptic myoclonic twitches," and may generate a rule that when those features appear together in a text portion, a "Problem" fact should be extracted. When the system then identifies the same features in the other text portions “myoclonic seizure” and “Myoclonic jerks,” it may apply the rule to label those text portions with the “Problem” fact type. In some embodiments, further processing may then be performed to determine the specific fact to be extracted from each text portion having a newly applied entity label. For example, in some embodiments, the relation model and the normalization/coding model described above for the initial fact extraction may then be applied in the revision processing to narrow the “Problem” labels to particular facts for the “myoclonic seizure” and “Myoclonic jerks” text portions. In other embodiments, the rule may specify that the particular fact that the user identified (e.g., as opposed to its more general fact type) should be extracted from other text portions having features that match those of the text portion corresponding to the user-identified fact.

In other instances, rather than generating a rule specifying that the automatically extracted features of a text portion for which the user specified a fact should lead to automatic extraction of that fact, in some embodiments the system may instead generate a rule specifying that one or more additional features should be extracted from one or more tokens in the text portion. For example, consider a case in which fact extraction component 104 would have automatically extracted the “myoclonic epileptic seizure” fact from text having a certain set of features, but fact extraction component 104 failed to extract one of the features in the set from the text portion “Epileptic myoclonic twitches.” In response to the user’s correction specifying that “myoclonic epileptic seizure” should be associated with “Epileptic myoclonic twitches,” in some embodiments the system may generate a rule specifying that the missing feature should be extracted from one or more tokens of “Epileptic myoclonic twitches” when that token is encountered in the future. Once the missing feature is extracted by applying the rule, the further fact extraction components may then automatically extract the appropriate fact from such text portions in other parts of the document or in other documents.

In some embodiments, rather than or in addition to generating the deterministic rule corresponding to the user correction to the initial set of extracted facts, the user correction may be used to re-train one or more statistical models used in the fact extraction. For example, in some embodiments, the user’s correction may be treated as a hand-labeling of the input text with a fact label, and the text with the user-supplied fact label may be added to training data to re-train the statistical model(s). In some embodiments, the input text portion, labeled with the fact identified by the user as corresponding to that text portion, may be added to training data (such as the original training data used to train the statistical model(s)) for any or all of the models used by fact extraction component 104, including any or all of the exemplary statistical models described above. Each such model may then be re-trained using the combined training corpus. In some embodiments, when the user-correction labeled text is added to the training data, it may be weighted differently from the original training data. In some embodiments, the user-correction training data may be weighted more heavily than the original training data, to ensure that it has an appreciable effect on the processing performed by the re-trained model. However, any suitable weighting may be used, and embodiments in which no weighting at all is performed may also be used, as aspects of the invention are not limited in this respect.

It should be appreciated that any of the above techniques may alternatively or additionally be used when a user corrects a set of facts by deleting an extracted fact, in which case one or more instances of the same or similar facts may automatically be suppressed from being extracted from one or more other text portions. For example, when a user deletes a fact that was extracted from a first portion of text, in some embodiments the system may then automatically suppress all extractions of that fact or one or more similar facts from other portions of text. In other embodiments, the system may not suppress all extractions of that fact or similar facts, but may only suppress extractions of that fact or similar facts from other portions of text that are sufficiently similar to the first portion of text corresponding to the extracted fact that the user deleted. Exemplary techniques for determining which portions of text are sufficiently similar to each other are described above.

In some embodiments, either one or more deterministic rules or one or more re-trained statistical models (or both) may be used to apply a user’s correction to other portions of the same text for which the user’s correction was received. Alternatively or additionally, in some embodiments either one or more deterministic rules or one or more re-trained statistical models (or both) may be used to apply the user’s correction to texts other than the one for which the user’s correction was received. For example, in some embodiments, the rules and/or model re-trainings learned from a user’s correction may be applied to improve fact extraction for all documents in the future. In other embodiments, the rules and/or model re-trainings learned from a user’s correction may only be applied to future documents generated by that user, or by the same clinician who provided that input text, or for the same institution in which the document was created, or to an appropriate set of future documents selected by any other suitable criteria. In some embodiments, deterministic rules may be used to apply a user’s correction to other portions of the same text, while the statistical model(s) may be re-trained to apply the user’s correction to other texts. However, this is merely one example, as aspects of the invention are not limited to any particular contexts in which to apply deterministic rules or to re-train statistical models.

In some embodiments, the set of medical facts corresponding to the current patient encounter (each of which may have been extracted from the text narrative or provided by the user as a discrete structured data item) may be added to an existing electronic medical record (such as an EHR) for patient 122, or may be used in generating a new electronic medical record for patient 122. In some embodiments, clinician 120 and/or coding specialist (or other user) 150 may finally approve the set of medical facts before they are included in any patient record; however, aspects of the present invention to are not limited in this respect. In some embodiments, when there is a linkage between a fact in the set and a portion of the text narrative, the linkage may be maintained when the fact is included in the electronic medical record. In some embodiments, this linkage may be made viewable by simultaneously displaying the fact within the electronic medical record and the text narrative (or at least the portion of the text narrative from which the fact was extracted), and providing an indication of the linkage in any of the ways described above. Similarly, extracted facts may be included in other types of patient records, and linkages between the facts in the patient records and the portions of text narratives from which they were extracted may be maintained and indicated in any suitable way.

In some embodiments, one or more medical facts, either automatically extracted from a text narrative by fact extraction component 104 or directly entered by a user as discrete structured data items, may be input to fact review component 106 for automatic review. In some embodiments, fact review component 106 may be programmed to identify opportunities for the medical documentation of the patient encounter to be improved, and if any such opportunities are identified, to provide an alert to the user (e.g., clinician 120 or other user 150). Some examples of alerts that may be provided are described above. As discussed, any suitable form of alert, including visual and/or audio alerts, may be used, as aspects of the invention are not limited in this respect. In some embodiments, the review of collected medical facts to determine opportunities for improved medical documentation, and the resulting alerting and/or querying of the user, may be performed entirely automatically by fact review component 106 or any other suitable component. As used herein, performing a process "automatically" refers to having no required human participation between the input to the process and its corresponding output, with all intervening acts performed by machine.

As discussed above, one type of alert that may be provided to a user by fact review component 106 is an alert of a potential opportunity to increase the specificity of the set of facts ascertained from the patient encounter. This can be done in any suitable way. In some embodiments, fact review component may be programmed with a set of deterministic rules to decide when such a potential opportunity exists. For example, in some embodiments, if a clinical term corresponding to one of the facts is linked to a concept in the formal ontology used by fact extraction component 104, and that concept is a parent to one or more more specific child concepts in the ontology, then fact review component 106 may generate an alert to query the user as to whether one of the more specific child concepts can actually be ascertained from the patient encounter. If the user answers in the affirmative, in some embodiments fact review component 106 may cause the more general fact to be replaced by a more specific version indicated by the user. Similarly, if one or more concepts in the formal ontology are linked to clinical terms appearing in the set of facts, and if those concepts have relationships in the ontology to a fact that could add specificity to the set of facts, and alert and/or query may be generated. As an example, if one or more conditions documented in the set of facts are known through ontological relationships to be symptoms of a specific diagnosis, in some embodiments fact review component 106 may query clinician 120 or other user 150 as to whether the specific diagnosis may be ascertained from the patient encounter and added to the facts. In some embodiments, as an alternative or in addition to the set of deterministic rules, a statistical model may be used to identify situations in which a potential opportunity to increase the specificity of the set of facts exists.

In another example, one or more of the facts in the set collected (either by fact extraction from a text narrative or by direct entry as one or more discrete structured data items) from the patent encounter may correspond to one or more standard codes used for billing, ordering, evaluating quality of care, or the like. Such standard codes may be specific to the healthcare institution or may be a standard shared by multiple institutions. Examples of such standard coding systems include, but are not limited to, ICD codes, CPT (Current Procedural Terminology) codes, E&M (Evaluation and Management) codes, MedDRA (Medical Dictionary for Regulatory Activities) codes, SNOMED codes, LOINC (Logical Observation Identifiers Names and Codes) codes, RxNorm codes, NDC (National Drug Code) codes and RadLex codes. Some such standard coding systems are hierarchical, in that certain codes within the system are more specific versions of other codes within the system. For example, in the ICD-10 coding system, code I20 represents "angina pectoris" (chest pain due to lack of blood and oxygen to the heart muscle). More specific versions of ICD-10 code I20 include I20.0 ("unstable angina"), I20.1 ("angina pectoris with documented spasm"), I20.8 ("other forms of angina pectoris") and I20.9 ("angina pectoris, unspecified"). In some embodiments, if one of the set of facts collected from the patient encounter includes a general-level code such as ICD-10 I20, fact review component 106 may be programmed to automatically query the user as to whether one of the corresponding specific-level codes could be ascertained from the patient encounter instead. In some embodiments, fact review component 106 may present the user with a structured choice among the available specific-level codes, and may allow the user to choose among the available options.

In another example, fact review component 106 may be programmed to alert the user when a specific fact may be implied by the combination of two or more facts appearing together in the set of facts collected from the patient encounter. One example is a set of facts that included a diagnosis of pneumonia as well as a test result indicating that pseudomonas was found in a sputum culture. Based on a deterministic rule, or a statistical model result, indicating that these two facts in combination may imply a more specific form of pneumonia due to the presence of an organism, fact review component 106 may query the user as to whether the more specific diagnosis can be ascertained from the patient encounter.

In some embodiments, an alert that would otherwise be generated from the current patient encounter may be suppressed if there is information in the patient's medical history that already provides the additional specificity. To this end, in some embodiments fact review component 106 may have access to a data set of patient history records 160 for patient 122, and may query patient history records 160 for such information prior to generating an alert to the user. For example, if the set of facts from the current patient encounter specifies a condition but does not specify whether it is "acute" or "chronic," but a previous record in patient history records 160 already specifies that the condition is "chronic," then fact review component 106 in some embodiments may automatically edit the set of facts for the current patient encounter to specify that the condition is "chronic," without bothering the user with an alert. However, in some embodiments, even if fact review component 106 can obtain such specificity enhancing information automatically, a message may still be generated to inform the user that the information is being automatically added, and to allow the user to reject the change if desired, or to ask the user to approve of the change being made.

In some embodiments, if it is a user 150, and not clinician 122, who responds to an alert to increase the specificity of a set of clinical facts for a patient encounter, clinician 120 may be prompted to approve any additional information provided by the other user 150 prior to finally approving the set of facts for the patient encounter. For example, in some embodiments user 150 may be a coding specialist who is assigned the task of reviewing and editing the set of clinical facts (which may include billing codes) into a version fit to be incorporated into an electronic medical record, patient reports, order forms, or other document types. In such a "back-end" arrangement, the set of clinical facts settled upon by coding specialist 150 may then in some embodiments be transmitted to clinician 120 to give final approval to the set of facts. In some other embodiments, coding specialist 150 may not be required. For example, in a "front-end" arrangement, clinician 120 may review and possibly edit the set of clinical facts himself, and finally approve the set of facts when he is satisfied. This may occur during the patient encounter in some embodiments, or at some time thereafter (e.g., before clinician 120 finally approves or signs off on the report) in other embodiments. In either type of arrangement, in some embodiments, processing by fact review component 106 or any other component to provide alerts, decision support, workflow tools or the like in relation to the set of facts may be performed prior to the clinician's final approval of the set of facts.

In some embodiments, similar processing may be performed by fact review component 106 to alert the user when it is determined that an unspecified diagnosis may possibly be ascertained from the patient encounter. As discussed above, examples of such unspecified diagnoses include comorbidities of one or more already specified diagnoses, and identification of one or more already specified diagnoses as complications of one or more other specified diagnoses and/or procedures. For example, if the set of facts collected for the patient encounter specified a diagnosis of pneumonia, and the patient's oxygen saturation is also low, it may be determined that respiratory failure, a comorbidity of pneumonia, may possibly be ascertained from the patient encounter. In such a case, fact review component 106 may generate an alert to the user. In some embodiments, such determinations may be made based on knowledge of best practices, with deterministic rules providing reminders of diagnoses that should be investigated, for best quality of care, when other related conditions are present. In other embodiments, such determinations may be made statistically, by inputting the collected set of facts and/or facts from the patient's medical history to a statistical model trained on past clinical reports and/or medical literature. In this way, patterns of diagnoses that tend to be related may be identified statistically, and alerts may be generated based on the likelihood that relationships observed in the past will surface in the current patient encounter. To this end, in some embodiments, fact review component 106 may have access to a data set of medical literature/documents 170 (such as past clinical reports from the healthcare institution and/or from other sources) from which statistical models may be built and updated.

In some embodiments, as discussed above, fact review component 106 may be programmed to generate an alert when it determines that two or more of the facts in the set collected from the patient encounter conflict with each other in some way, or when it determines that one or more of the facts in the set conflict with one or more facts in patient history records 160. In some embodiments, fact review component 106 may be programmed to automatically generate such alerts based on a known set of combinations of facts that have undesirable interactions. For example, an alert may be generated when the set of facts indicate that patient 122 has been prescribed a certain medication (drug A) in addition to a certain other medication (drug B) with which it negatively interacts, such that the two medications should not be prescribed together. In some embodiments, the prescriptions of both drug A and drug B may be specified in the set of facts collected from the current patient encounter, while in other embodiments, the prescription of drug A may be specified in a fact from the current patient encounter, and the prescription of drug B may be specified in a fact contained in patient history records 160. In some embodiments the known set of undesirable interactions may be represented in a data set locally accessible to fact review component 106, while in other embodiments, fact review component 106 may query one or more external data sets (such as those maintained by pharmacies) to determine whether given facts for patient 122 demonstrate any contraindications. In some embodiments, fact review component 106 or another suitable processing component may both maintain an internal data set and also query external data sets, for instance for periodic updates to the internal data set.

In some embodiments, an alert to a conflict may be triggered by a combination of facts, at least one of which does not correspond to a medication. For example, fact review component 106 may generate alerts for contraindications related to a combination of a medication with an allergy, a medication with a diagnosis, a medication with a patient's age or gender, a medication with a condition indicated in the patient's history, a medical procedure with any of the foregoing characteristics, or any other combination of a planned treatment with another clinical fact from the current patient encounter or from the patient's history for which the planned treatment is known to be contraindicated.

In some embodiments, as discussed above, fact review component 106 may generate an alert when it determines that there is an opportunity to add to the clinical documentation of the patient encounter for quality review purposes. In some embodiments, fact review component 106 may be programmed with a set of deterministic rules to generate automatic alerts in response to certain facts or certain combinations of facts, based on a standard set of quality of care measures. Such a quality of care standard may be proprietary and unique to the specific healthcare institution or may be a standard that is not institution specific, such as the PQRI standard or the JCAHO standard. Any suitable quality of care standard may be used, as aspects of the present invention are not limited to any particular quality of care standard. In some embodiments, when a collected fact or combination of facts is associated with a certain recommended action on the part of the clinician according to the quality of care standard, an alert may be provided to query the user as to whether the recommended action was performed. For example, if the set of facts specify that patient 122 is a smoker, in some embodiments fact review component 106 may generate an alert to remind clinician 120 to counsel patient 122 about quitting smoking, and to document the counseling in the patient record. In another example, if the set of facts specify that patient 122 presented with a heart attack, in some embodiments fact review component 106 may prompt clinician 120 to document how quickly aspirin was prescribed and/or administered, such that proof of compliance with the applicable quality of care standards may be documented. In some embodiments, fact review component 106 may be used to generate PQRI score reports, or the like, to send to insurance companies as compliance evidence to support reimbursement.

In some embodiments, as discussed above, fact review component 106 or another suitable component may generate an alert to the user when it determines that disambiguation is desired between multiple facts that could potentially be extracted from the same portion of the text narrative. For example, a term in the free-form narration might be linked to two different concepts in the formal ontology used by fact extraction component 104, and it might not be likely that both of those concepts were intended to coexist in the free-form narration. For example, if the text narrative contains the word "cold," it may be difficult in some cases for fact extraction component 104 to determine whether clinician 120 intended that word to mean that patient 122 is cold to the touch, that patient 122 has a runny nose, or that patient 122 has chronic obstructive lung disease (COLD). In other examples, as discussed above, multiple alternative hypotheses for a fact to be extracted from a portion of the text may be identified, e.g., as the text is processed by one or more statistical fact extraction models. In such situations, fact review component 106 in some embodiments may provide a structured choice to the user to disambiguate between multiple facts tentatively extracted by fact extraction component 104. In some embodiments, each of the options provided in the structured choice may correspond to one of the multiple tentative facts, and the user may choose one of the options to specify which fact should actually be extracted from the free-form narration. As discussed above, if the user choosing among the facts is a person other than clinician 120, such as coding specialist 150, then in some embodiments clinician 120 may be prompted to approve the user's choice before finally approving the set of facts for the patient encounter. In other embodiments, the user may be prompted to provide disambiguating information in free-form, rather than as a structured choice, as aspects of the invention relating to prompting for disambiguating information are not limited to any particular implementation.

In various situations, as discussed above, fact review component 106 may be programmed to generate an alert including a structured choice among a number of options corresponding to medical facts that could possibly be ascertained from the patient encounter. Such a structured choice could include a choice among facts that could add specificity to a set of clinical facts already collected for the patient encounter, a choice among facts potentially implied by one or more combinations of facts already collected for the patient encounter, a choice to disambiguate between facts, or any other choice in which one or more structured options are presented to the user, from which the user may choose. Such a structured choice may be provided in any suitable way, including as a visual and/or audio listing of the options in the structured choice, as aspects of the invention are not limited in this respect. Similarly, the user's selection of an option from the structured choice may be received in any suitable way, including as manual input and/or spoken input, as aspects of the invention are not limited in this respect.

In some embodiments, in response to the user's selection of one of the options, fact review component 106 may, for example through use of fact extraction component 104, perform an update to the text narrative to make it explicitly state information corresponding to the selected fact. For example, in some embodiments, fact extraction component 104 may in a sense work backward from the selected fact to generate natural language text from which that fact could have been extracted in the forward sense. In some embodiments, the generated text may then be added to the text narrative. When the fact selected by the user through the structured choice is a replacement for or a disambiguation of a fact already extracted from the text narrative, the generated text may in some embodiments be used to replace the portion of the text narrative from which the original fact was extracted. In some embodiments, to determine where in the text narrative to add the generated text when no other text is to be replaced, fact extraction component 104 may again work backward based on how the selected fact would have been extracted from the narrative. For example, in some embodiments fact extraction component 104 may identify a section heading in the text narrative corresponding to the selected fact, and the generated text may be added to that section. (e.g., because a selected fact with a status of "history" would have been extracted from a section with a "history" heading, the corresponding generated text may be added to such a section in the text narrative.) In other embodiments, generated text may simply be added to a predetermined location in the text narrative, such as at the beginning or end of the narrative, regardless of the semantic content of the generated text.

In some embodiments, fact review component 106 may allow the user to specify a location in the text narrative where the generated text should be inserted, or may allow the user to correct the location initially determined automatically. In some embodiments, fact extraction component 104 or another suitable component may be used to update the generated text in response to the user's indication of a new location at which to insert it in the text narrative. For example, based on whether the user selects a location that is sentence-initial, sentence-medial or sentence-final, or a location that is its own sentence or is within another sentence, the generated text may be adjusted in terms of capitalization, spacing, punctuation, etc., to fit the selected location syntactically. In another example, if a selected fact specifies a family history of a certain condition, the gender of one or more pronouns within the generated text may be adjusted based on whether the user selects a location in a sentence about a female relative or about a male relative. As in other situations, if the user selecting an option from a structured choice and/or specifying a location in the text narrative is a person other than clinician 120, in some embodiments clinician 120 may be prompted to approve the user's selections prior to finally approving the set of clinical facts.

Figure 6:
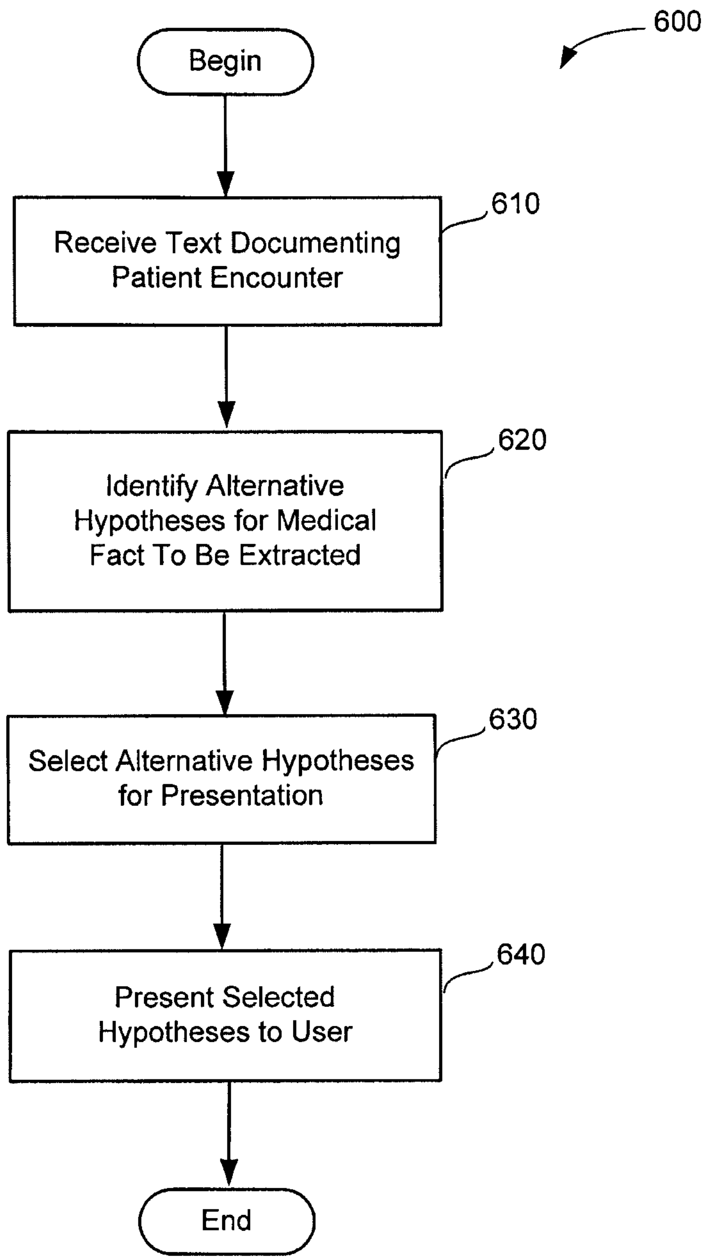
FIG. 6 is a flowchart illustrating an exemplary method for presenting alternative hypotheses for a medical fact in accordance with some embodiments of the present invention.

It should be appreciated from the foregoing that one embodiment of the invention is directed to a method 600 for presenting alternative hypotheses for a medical fact, as illustrated in FIG. 6. Method 600 may be performed, for example, by one or more components of a medical documentation system such as fact extraction component 104 and/or fact review component 106, although other implementations are possible and method 600 is not limited in this respect. Method 600 begins at act 610, at which text documenting a patient encounter may be received. As discussed above, such text may be received in any suitable way, as aspects of the invention are not limited in this respect. In some embodiments, the text may be manually input, e.g., via a keyboard, by medical personnel documenting the patient encounter. In other embodiments, the text may be dictated by medical personnel using speech, and a text transcription of the dictation may be created by a transcriptionist, and/or automatic speech recognition (ASR) techniques may be used to automatically convert the dictated speech to text, and/or to format the dictation in any of various ways, examples of which are discussed above.

At act 620, a plurality of alternative hypotheses for a medical fact to be extracted from a portion of the text may be identified. As discussed above, in some embodiments such alternative hypotheses may be identified through processing the text using one or more statistical fact extraction models. Exemplary techniques are described above. At act 630, two or more of the identified alternative hypotheses may be selected for presentation to the user. As discussed above, any suitable technique for selecting among the alternative hypotheses may be used, as aspects of the invention are not limited in this respect. In some embodiments, as discussed above, the selected hypotheses may be the N-best alternative hypotheses, and/or may have calculated likelihoods above a threshold value. Method 600 ends at act 640, at which the selected alternative hypotheses may be presented to the user. Exemplary techniques for presenting alternative hypotheses to the user are described above, although any suitable technique(s) may be used, as aspects of the invention are not limited in this respect.

Figure 7:
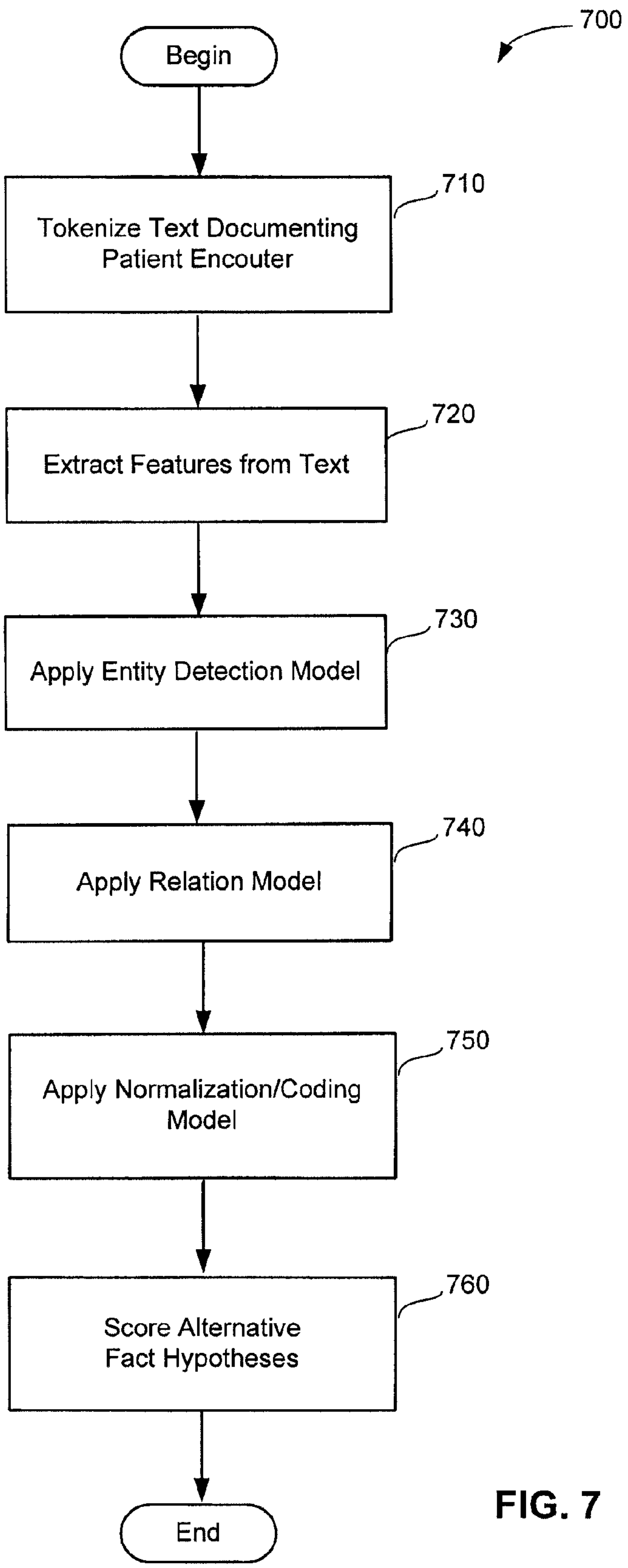
FIG. 7 is a flowchart illustrating an exemplary method for identifying alternative hypotheses for a medical fact to be extracted in accordance with some embodiments of the present invention.

It should be appreciated from the foregoing that another embodiment of the invention is directed to a method 700 for identifying alternative hypotheses for a medical fact, as illustrated in FIG. 7. Method 700 may represent, for example, an exemplary process for performing act 620 in method 600 discussed above. Method 700 may be performed, for example, by one or more components of a medical documentation system such as fact extraction component 104, although other implementations are possible and method 700 is not limited in this respect. Method 700 begins at act 710, at which text documenting a patient encounter may be tokenized. Exemplary techniques for performing tokenization are discussed above. At act 720, features may be extracted from the tokenized text. Exemplary techniques for feature extraction are also discussed above. As discussed above, any suitable set of features may be used, as aspects of the invention are not limited in this respect.

Exemplary method 700, as illustrated in FIG. 7, applies three different models or model components to the featurized text. As discussed above, however, this is not required. In some embodiments, a single model may be used to perform the functionality of any or all of the models depicted in the example of FIG. 7. Furthermore, in some embodiments, the same set of features may be used by each of the models and/or model components. In other embodiments, however, one or more different models may use one or more different feature sets than one or more other models. As discussed above, any suitable set(s) of features may be used, as aspects of the invention are not limited in this respect.

At act 730 of exemplary method 700, an entity detection model may be applied to the featurized text to automatically label text portions with entity labels corresponding to fact types/categories. Exemplary techniques for performing such entity detection, and for creating and/or training an entity detection model, are discussed above. As discussed above, in some embodiments an entity detection model may be rule-based, while in other embodiments an entity detection model may be statistically trained, or may utilize a combination of rules and statistical techniques.

At act 740, a relation model may be applied to the text labeled with fact types, to relate various entity mentions to specific medical facts. Exemplary techniques for performing such relation identification, and for creating and/or training a relation model, are discussed above. As discussed above, in some embodiments a relation model may be rule-based, while in other embodiments a relation model may be statistically trained, or may utilize a combination of rules and statistical techniques.

At act 750, a normalization/coding model may be applied to the specific medical facts identified by the relation model, to map them to their standard forms and/or codes. Exemplary techniques for performing such normalization/coding are discussed above. As discussed above, in some embodiments a normalization/coding model may be rule-based.

Method 700 ends at act 760, at which alternative hypotheses generated in any of the foregoing acts for a medical fact to be extracted from the text may be scored. Exemplary techniques for scoring alternative hypotheses for a medical fact are discussed above. As discussed above, in some embodiments, scoring alternative hypotheses may involve determining an estimated likelihood that each alternative hypothesis accurately represents an intended semantic meaning of the text portion from which it was extracted. Also as discussed above, the scores for alternative hypotheses determined in act 760 may be used in any of various ways to select two or more of the alternative hypotheses for presentation to the user.

Figure 8:
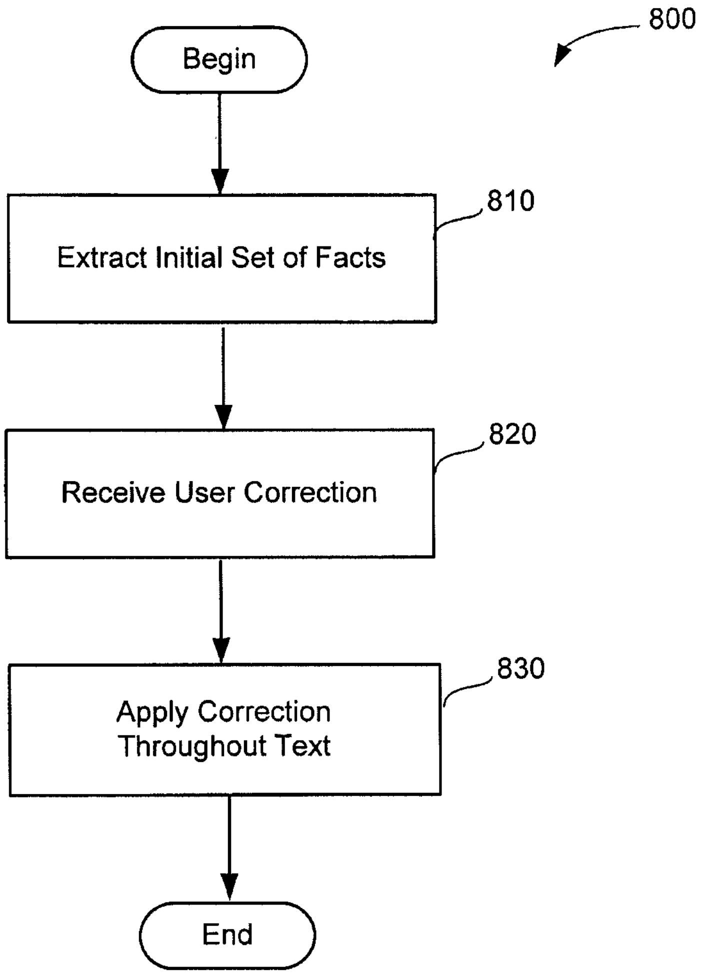
FIG. 8 is a flowchart illustrating an exemplary method for applying a user correction to extracted facts in accordance with some embodiments of the present invention.

It should be appreciated from the foregoing that another embodiment of the invention is directed to a method 800 for applying a user correction to extracted facts, as illustrated in FIG. 8. Method 800 may be performed, for example, by one or more components of a medical documentation system such as fact extraction component 104 and/or fact review component 106, although other implementations are possible as method 800 is not limited in this respect. Method 800 begins at act 810, at which an initial set of medical facts may be extracted from narrative text documenting a patient encounter. As discussed above, the initial set of facts may include a first set of one or more facts automatically extracted from a first portion of the text. At act 820, a user correction to the first set of facts may be received. As discussed above, in some embodiments, the user correction may identify a fact that should be associated with the first portion of the text. In other cases, the user correction may remove a fact from the initial set of facts that were automatically extracted. Method 800 ends at act 830, at which the user's correction may automatically be applied throughout the text. As discussed above, when the user correction identifies a fact that should be associated with the first portion of the text, applying the user's correction may involve extracting one or more similar facts from one or more other portions of the text. When the user correction removes a fact from the initial set of automatically extracted facts, applying the user's correction may involve removing the same or similar facts that were initially automatically extracted from one or more other portions of the text.

Figure 9:
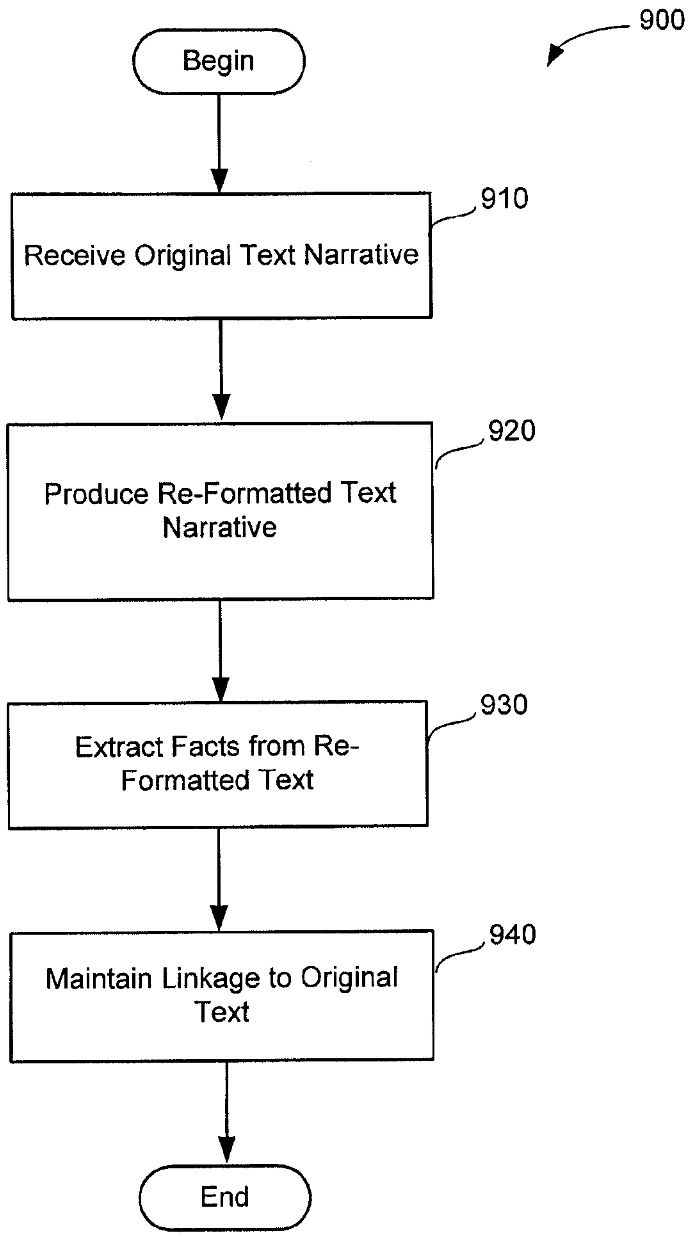
FIG. 9 is a flowchart illustrating an exemplary method for formatting text for clinical fact extraction in accordance with some embodiments of the present invention.

It should be appreciated from the foregoing that another embodiment of the invention is directed to a method 900 for formatting text for clinical fact extraction, as illustrated in FIG. 9. Method 900 may be performed, for example, by one or more components of a fact review system such as ASR engine 102 and/or fact extraction component 104, although other implementations are possible as method 900 is not limited in this respect. Method 900 begins at act 910, at which an original text narrative (e.g., a textual representation of a narration of a patient encounter provided by a clinician) may be received. At act 920, the original text may be re-formatted to produce a formatted text narrative. At act 930, one or more clinical facts may be extracted from the formatted text. Method 900 ends at act 940, at which a linkage between at least one of the clinical facts and a corresponding portion of the original text may be maintained.

Figure 10:
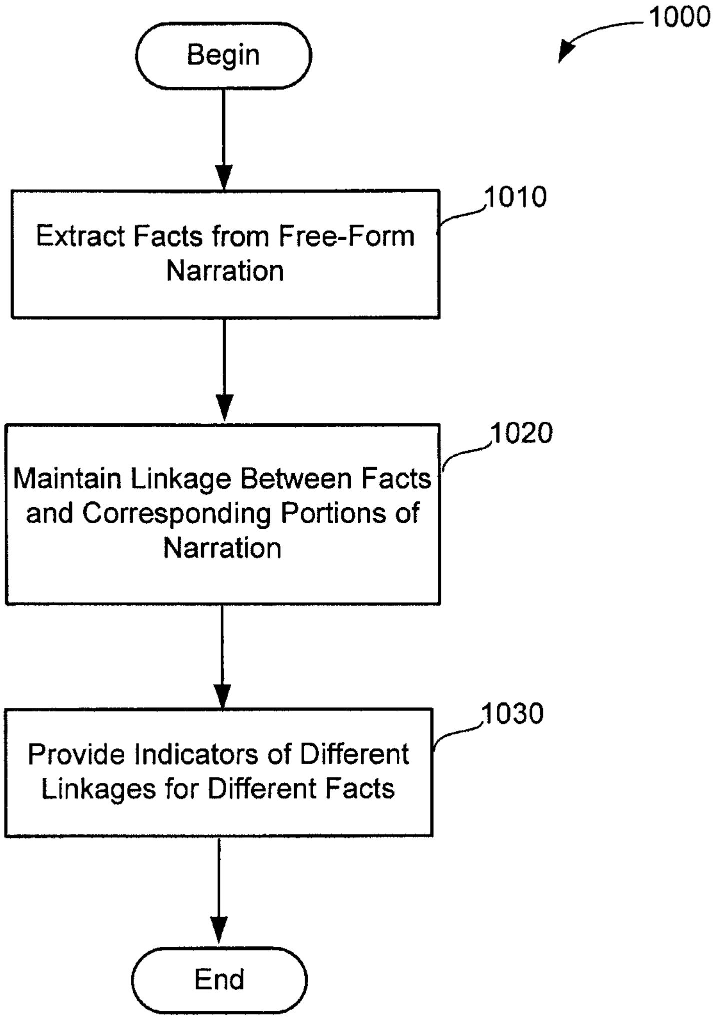
FIG. 10 is a flowchart illustrating an exemplary method for linking extracted clinical facts to text in accordance with some embodiments of the present invention.

It should be appreciated from the foregoing that another embodiment of the invention is directed to a method 1000 for linking extracted clinical facts to text, as illustrated in FIG. 10. Method 1000 may be performed, for example, by one or more components of a fact review system such as fact extraction component 104 and/or fact review component 106, although other implementations are possible and method 1000 is not limited in this respect. Method 1000 begins at act 1010, at which a plurality of facts may be extracted from a free-form narration of a patient encounter provided by a clinician. At act 1020, a linkage may be maintained between each fact (or at least two of the facts) and the corresponding portion of the free-form narration from which it was extracted. Method 1000 ends at act 1030, at which a different indicator may be provided for each fact, to indicate the linkage between that fact and its corresponding portion of the free-form narration.

Figure 11:
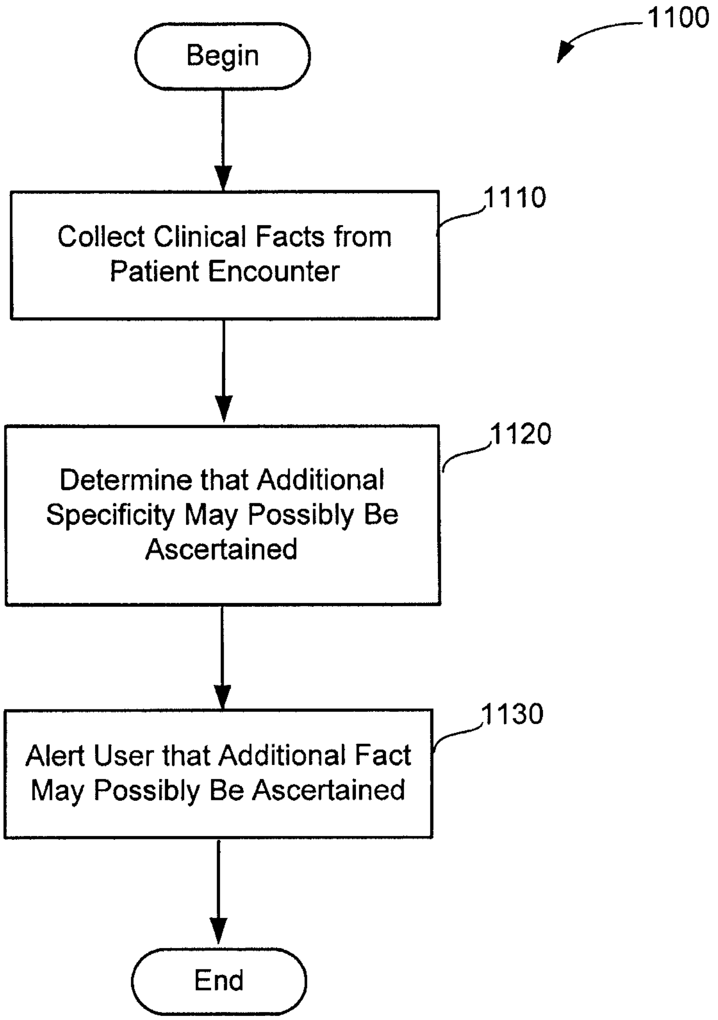
FIG. 11 is a flowchart illustrating an exemplary method for analyzing specificity in accordance with some embodiments of the present invention.

It should be appreciated from the foregoing that another embodiment of the invention is directed to a method 1100 for analyzing specificity in clinical documentation, as illustrated in FIG. 11. Method 1100 may be performed, for example, by one or more components of a fact review system such as ASR engine 102, fact extraction component 104 and/or fact review component 106, although other implementations are possible and method 1100 is not limited in this respect. Method 1100 begins at act 1110, at which a set of one or more clinical facts may be collected from a clinician's encounter with a patient. At act 1120, it may be determined from the set of facts that additional specificity may possibly be ascertained from the patient encounter. Method 1100 ends at act 1130, at which a user may be alerted that an additional fact adding specificity to the set of facts may possibly be ascertained from the patient encounter.

Figure 12:
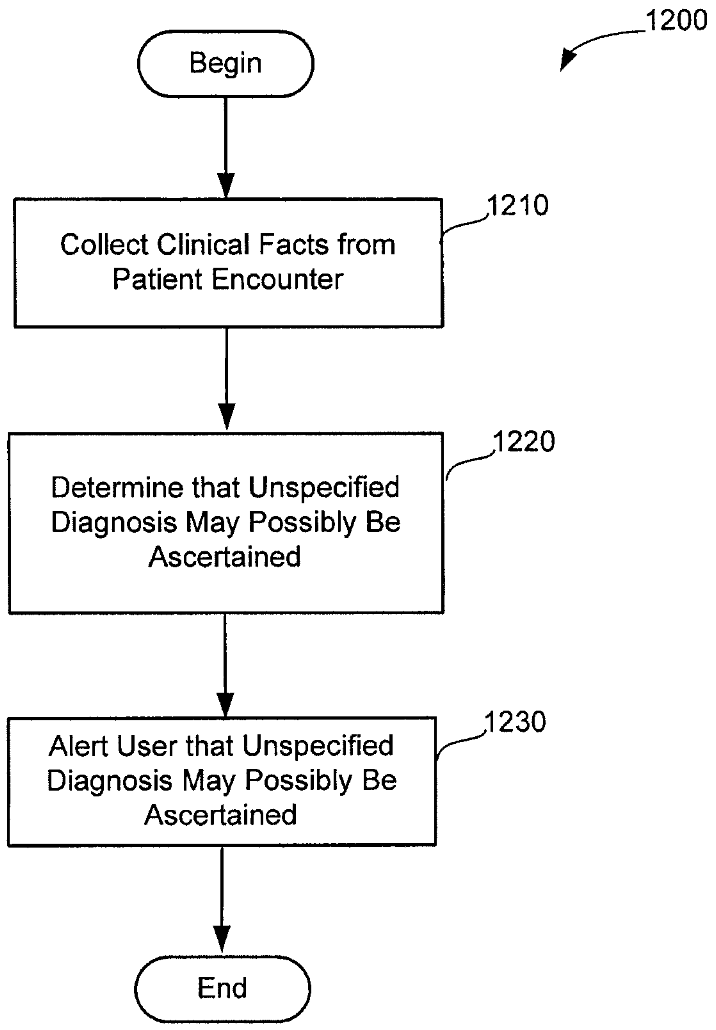
FIG. 12 is a flowchart illustrating an exemplary method for identifying an unspecified diagnosis in accordance with some embodiments of the present invention.

It should be appreciated from the foregoing that another embodiment of the invention is directed to a method 1200 for identifying unspecified diagnoses in clinical documentation, as illustrated in FIG. 12. Method 1200 may be performed, for example, by one or more components of a fact review system such as ASR engine 102, fact extraction component 104 and/or fact review component 106, although other implementations are possible and method 1200 is not limited in this respect. Method 1200 begins at act 1210, at which a set of one or more clinical facts may be collected from a clinician's encounter with a patient. At act 1220, it may be determined from the set of facts that an unspecified diagnosis may possibly be ascertained from the patient encounter. Method 1200 ends at act 1230, at which a user may be alerted that the unspecified diagnosis may possibly be ascertained from the patient encounter.

Figure 13:
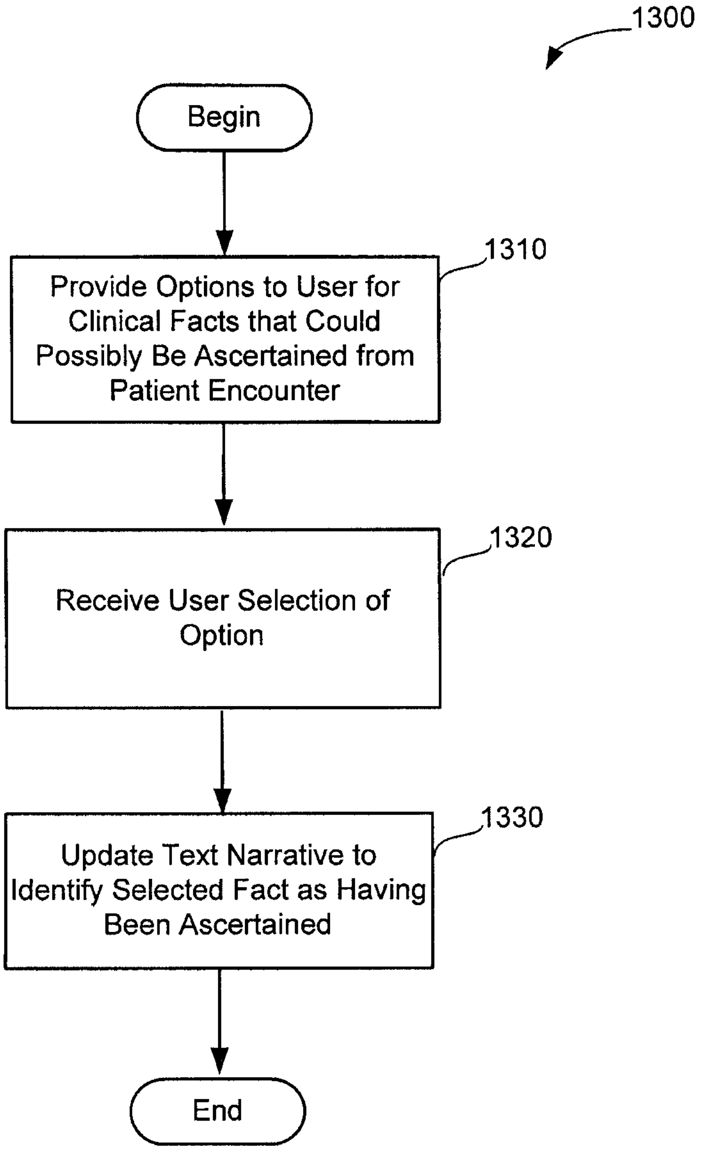
FIG. 13 is a flowchart illustrating an exemplary method for updating text in accordance with some embodiments of the present invention.

It should be appreciated from the foregoing that another embodiment of the invention is directed to a method 1300 for updating text in clinical documentation, as illustrated in FIG. 13. Method 1300 may be performed, for example, by one or more components of a fact review system such as fact extraction component 104 and/or fact review component 106, although other implementations are possible and method 1300 is not limited in this respect. Method 1300 begins at act 1310, at which one or more options may be provided to a user, the one or more options corresponding to one or more clinical facts that could possibly be ascertained from a patient encounter. At act 1320, a user selection of one of the options may be received. Method 1300 ends at act 1330, at which a text narrative (e.g., a textual representation of a free-form narration of the patient encounter provided by a clinician) may be updated to identify the fact corresponding to the selected option as having been ascertained from the patient encounter.

Figure 14:
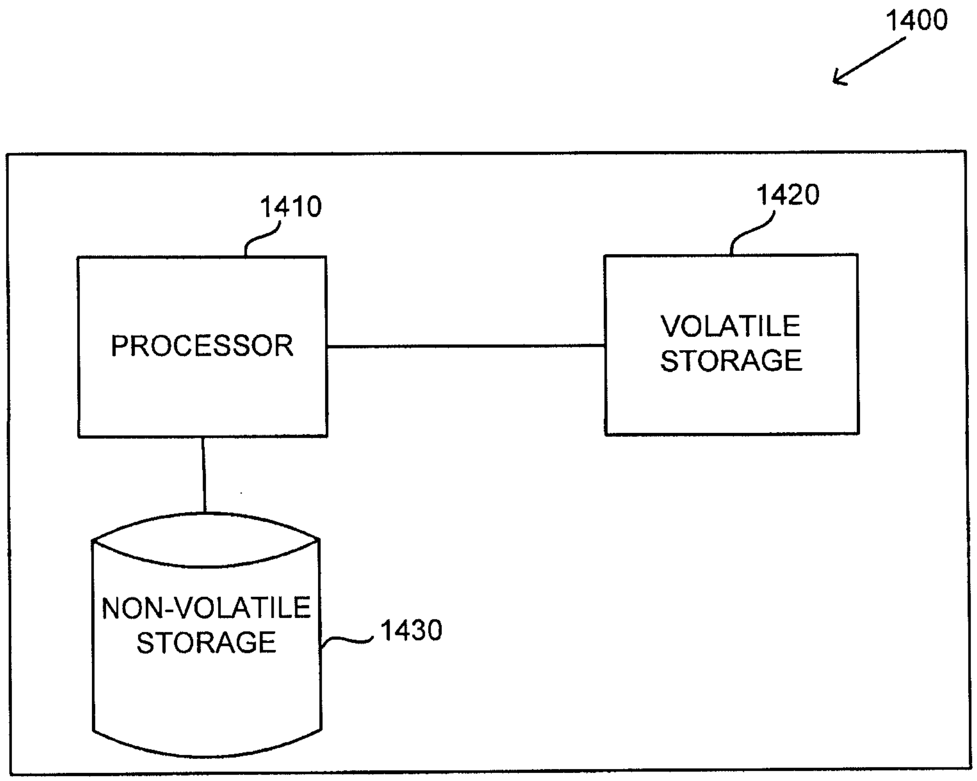
FIG. 14 is a block diagram of an exemplary computer system on which aspects of the present invention relating a medical documentation system may be implemented.

A medical documentation system 100 in accordance with the techniques described herein may take any suitable form, as aspects of the present invention are not limited in this respect. An illustrative implementation of a computer system 1400 that may be used in connection with some implementations of a medical documentation system 100 is shown in FIG. 14. One or more computer systems such as computer system 1400 may be used to implement any of the functionality of the medical documentation system 100 described above. The computer system 1400 may include one or more processors 1410 and one or more tangible, non-transitory computer-readable storage media (e.g., volatile storage 1420 and one or more non-volatile storage media 1430, which may be formed of any suitable non-volatile data storage media). The processor 1410 may control writing data to and reading data from the volatile storage 1420 and the non-volatile storage device 1430 in any suitable manner, as the aspects of the present invention are not limited in this respect. To perform any of the functionality described herein, the processor 1410 may execute one or more instructions stored in one or more computer-readable storage media (e.g., volatile storage 1420), which may serve as tangible, non-transitory computer-readable storage media storing instructions for execution by the processor 1410.

CDI System

As briefly noted above, a CDI system, such as the CDMP Guide product offered by JATA, provides a tool for a user to examine patient specific records for compliance with standard formats and protocols, to issue clarification requests to clinicians or others for clarification or supplementation of factual data, and to otherwise ensure that medical records are as complete and accurate as possible. Such accuracy and completeness may be important, for example, to ensure that appropriate codes may be assigned for billing and record keeping purposes, such as Diagnosis Related Group (DRG) codes or ICD-9-CM Diagnosis Codes used for Medicare or other billing purposes.

Figure 15:
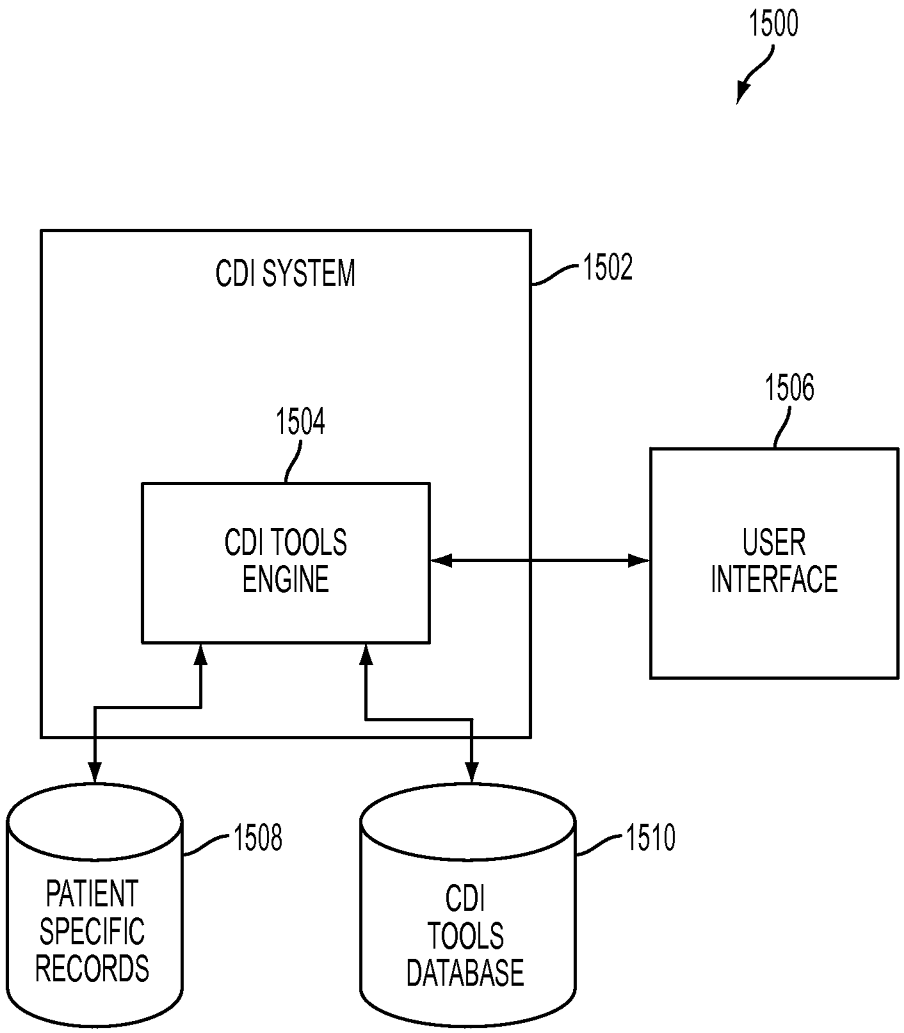
FIG. 15 is a block diagram illustrating an exemplary implementation of a CDI system that may be employed in connection with some embodiments of the invention.

An example of a CDI system architecture 1500 that may be employed in various embodiments of the invention is shown in FIG. 15. As shown, the architecture 1500 may include a CDI system 1502, including a CDI tools engine 1504, a user interface 1506, a database 1508 for storing patient specific records, and a database 1510 for storing documentation and data the CDI tools engine 1504 may use to implement the CDI process. In other embodiments, only a single database or other storage mechanism, or one or more databases in addition to those illustrated, may alternatively be used both for storing patient specific records and for providing resources for the CDI process.

The database 1510 may, for example, contain data reflecting nested menus of diagnosis possibilities corresponding to DRG, ICD-9-CM or other codes, as well as corresponding descriptive material, that allow a CDS to drill down to a specific diagnosis that can be used for billing and record keeping purposes. Should more detail be required in order to pinpoint a particular diagnosis, to clarify an ambiguity, or to fill in gaps in a record of a patient encounter, the CDS can use the CDI system 1502 to generate a request for clarification or additional detail from the clinician.

The user interface 1506 may take on any of numerous forms, and the invention is not limited to any particular implementation. Like the user interfaces for the medical documentation system 100 described above, the user interface 1506 may provide tools that allow a CDS to interact with the CDI system 1502 in any suitable form, including visual forms, audio forms, combined forms, or any other form providing the functionality described herein, as aspects of the present invention are not limited in this respect. When the tools are provided in visual form, their functionality may be accessed through a graphical user interface (GUI). In some embodiments, the GUI may be organized in a way to allow the human user(s) to efficiently process the information displayed. For example, in some embodiments, text narratives, facts, alerts, diagnoses possibilities and selection options, and tools to request clarifications or additional information from clinicians may be displayed in consistent locations within the user interface and organized by type and/or priority. Different colors, textual styles, and/or graphical styles may be utilized to direct the user's attention to high-priority alerts, and/or to make linkages between related items in the display easily recognizable. In some embodiments, the organization and/or composition of such a visual display may be determined in accordance with principles used in the development of heads-up displays (HUDs).

Figure 16:
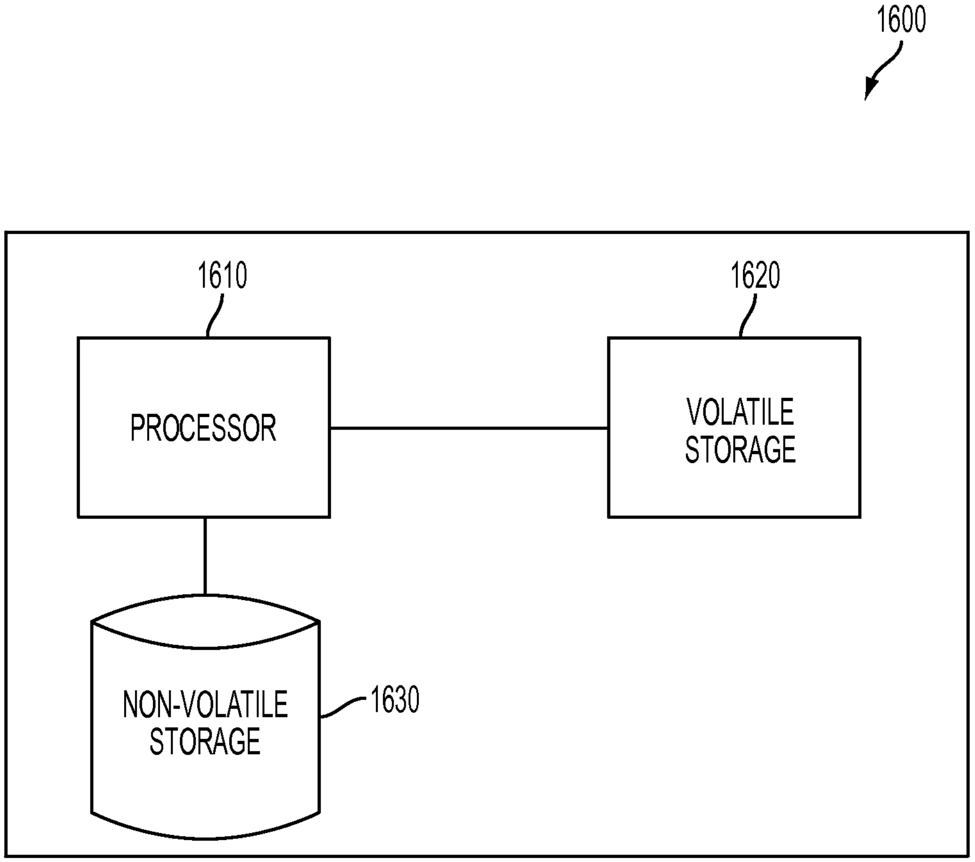
FIG. 16 is a block diagram of an exemplary computer system on which aspects of the present invention relating a CDI system may be implemented.

Like the embodiments of the medical documentation system 100 described above, the CDI system 1502 in accordance with the techniques described herein may take any suitable form, as aspects of the present invention are not limited in this respect. An illustrative implementation of a computer system 1600 that may be used in connection with some implementations of a CDI system 1502 is shown in FIG. 16. One or more computer systems such as computer system 1600 may be used to implement any of the functionality of the CDI system 1502 described above. As shown, the computer system 1600 may include one or more processors 1610 and one or more tangible, non-transitory computer-readable storage media (e.g., volatile storage 1620 and one or more non-volatile storage media 1630, which may be formed of any suitable non-volatile data storage media). The processor 1610 may control writing data to and reading data from the volatile storage 1620 and the non-volatile storage media 1630 in any suitable manner, as the aspects of the present invention are not limited in this respect. To perform any of the functionality described herein, the processor 1610 may execute one or more instructions stored in one or more computer-readable storage media (e.g., volatile storage 1620), which may serve as tangible, non-transitory computer-readable storage media storing instructions for execution by the processor 1610.

Examples of Integration Techniques and Benefits

Figure 17:
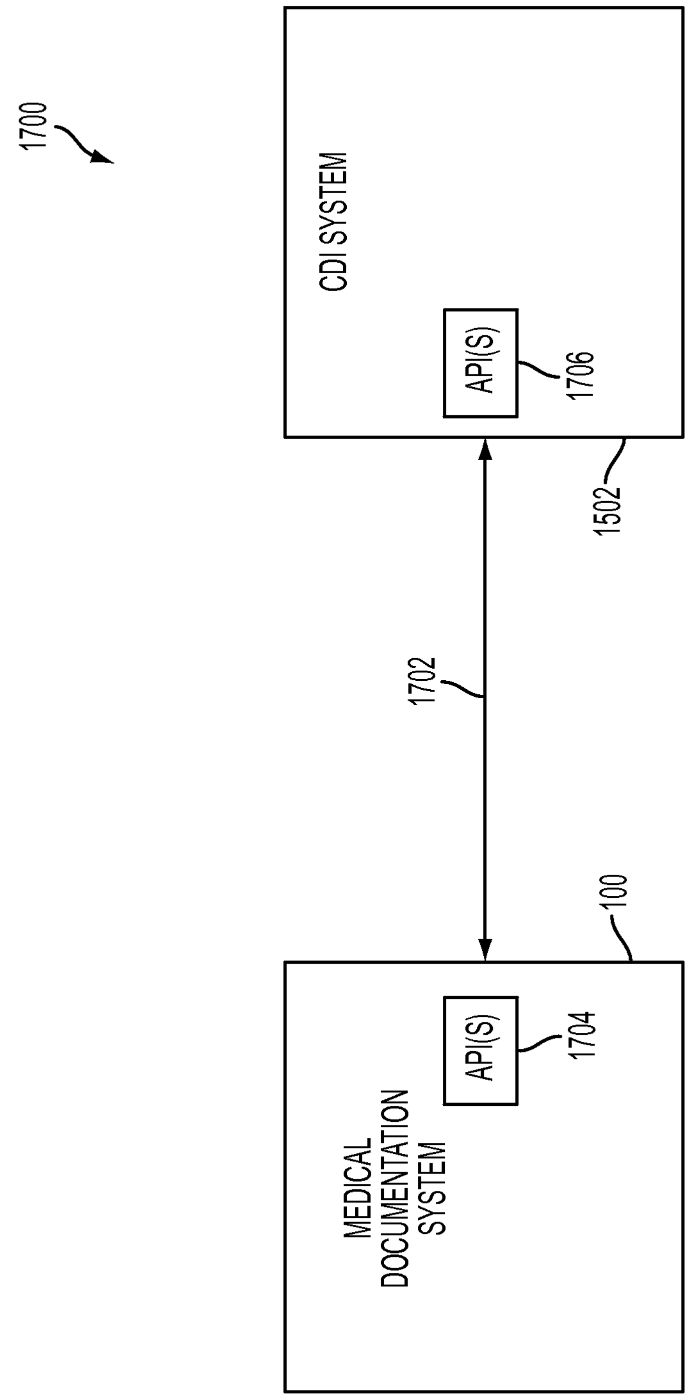
FIG. 17 is a block diagram illustrating an exemplary implementation in which a medical documentation system and a CDI system are integrated.

As noted above, in some embodiments, a medical documentation system 100 and a CDI system 1502 may be interlinked to allow information and messages to be shared between the two platforms. FIG. 17 shows an example implementation of an architecture 1700 in which a medical documentation system 100, such as that described above in connection with FIGS. 1-14, is integrated with a CDI system, such as that described above in connection with FIGS. 15-16, via a link 1702. The link 1702 may be implemented in any of numerous ways, and the invention is not limited to any particular type of interlinking mechanism. In some embodiments, for example, the systems 100, 1502 may communicate over a network via one or more Application Programming Interfaces (APIs) 1704, 1706, such as Web Services APIs, implemented in the software of the two systems. Such implementations may, for example, employ Simple Object Access Protocol (SOAP) messages formatted in Extensible Markup Language (XML) and sent using the Hypertext Transfer Protocol (HTTP). In other embodiments, the systems 100, 1502 may additionally or alternatively employ Representative State Transfer (REST) to exchange messages, and the transferred data may be formatted using JavaScript Object Notation (JSON), XML, or any other suitable structured data format. In yet other embodiments, the systems 100, 1502 may additionally or alternatively exchange messages using HTTP POST and/or GET request methods, and/or may employ APIs with traditional HTTP endpoints.

In some embodiments, upon opening of a patient case within the CDI system 1502, a call may, for example, be made to an API 1704 of the medical documentation system 100 requesting the transfer of a structured data set for the patient from a database accessible by the system 100 to the CDI system 1502. As noted above, the structured data set may be formatted using a suitable structured data format, such as XML, JSON, etc. In response to such a Web Services API call, the medical documentation system 100 may return such a structured data set containing some or all of the activities for the patient case that have been generated by the medical documentation system 100 as of the time of the request.

The interface between the medical documentation system 100 and the CDI system 1502 thus allows information of various types to be transmitted to the CDI system 1502 where it may be accessed and acted upon by the CDS operating the CDI system 1502. In some embodiments, for example, the transferred information may include information about clarification requests that were generated automatically by the medical documentation system 100 and forwarded to the clinician for review. Upon reviewing such requests, the CDS operating the CDI system 1502 may in some circumstances respond to the request without receiving input from the clinician. For example, the CDS may access and review lab results and/or may review handwritten clinician notes not considered by the medical documentation system 100 that allow the CDS to respond to the request without clinician input. Once the CDS has responded to such a request, the CDI system 1502 may, for example, make a call to an API 1704 of the medical documentation system 100, instructing the medical documentation system to identify the clarification request as addressed, and indicating that the clinician no longer needs to address the inquiry, thus reducing the clinician's workload.

Additionally or alternatively, the system 1700 may be configured such that, upon receiving a clarification request, the CDS may elevate the urgency of the request so as to cause the CDI system 1502 to make a call to an API 1704 of the medical documentation system 100 that, in turn, causes the priority of the clarification request provided to the clinician via the medical documentation system 100 to be escalated. For such an escalated request, the message may, for example, be moved to the head of the clinician's message queue or flagged in some way to indicate its urgency. In some embodiments, the clinician may even be paged or otherwise notified via an instant messaging system that an issue needs urgent attention.

In some embodiments, the medical documentation system 100 may assign a confidence score to each determination that a particular medical fact requires clarification or further input by a clinician, and such confidence scores may be transferred to the CDI system 1502 as a part of the structured data set transferred therebetween. Such confidence scores may then be used, for example, to identify certain facts that require review by a CDS via the CDI system 1502 before being passed to the clinician for review via an API 1704 of the medical documentation system 100. The medical documentation system 100 may, for example, refrain from passing clarification requests having confidence scores below a certain threshold level to the responsible clinician, and instead may rely upon the CDS performing a first level review of such entries via the CDI system 1502 and requesting clarification from the clinician via the medical documentation system 100 only when necessary. Should the CDS determine that such a low confidence score inquiry requires clinician attention, the CDS may instruct the CDI system 1502 to make a call to an API 1704 of the medical documentation system 100 that causes the system 100 to issue a clarification request to the clinician.

In some embodiments, the medical documentation system 100 may additionally or alternatively assign a confidence score to each extracted medical fact indicating the confidence of the system 100 in the accuracy of the fact, and such confidence scores may be transmitted to the CDI system 1502 as a part of the structured data set transferred therebetween. Either or both of the medical documentation system 100 and the CDI system 1502 may then treat the fact in a manner dependent on the assigned confidence score. In some embodiments, for example, the medical documentation system 100 may present only extracted facts having a confidence score above a certain threshold to a clinician for review and approval for entry into an EHR. The CDI system 1502 may, on the other hand, present extracted facts having confidence scores that do not exceed the threshold for clinician review to the CDS operating the CDI system 1502 for initial review. The CDS may then, for example, approve or correct the extracted medical fact using the CDI system 1502, and then may make a call to an API 1704 of the medical documentation system 100 requesting physician approval of the fact approved or corrected by the CDS, or perhaps requesting clarification or further input from the clinician.

As noted above, in some embodiments, in response to input by the CDS, the CDI system 1502 may communicate requests for clinician clarification to the medical documentation system 100 via an API 1704 that causes the medical documentation system 100 to generate a clarification request to the clinician. The general format of the clarification requests generated by the medical documentation system 100 may be the same as those generated automatically by the system 100, such that the clinician need only use a single interface to respond to clarification requests generated by either the medical documentation system 100 or the CDI system 1502. In some embodiments, the clarification requests received from the different sources may by identified and/or displayed in different ways, such as by highlighting the requests received from the respective sources using different colors and/or displaying the requests in different locations on the screen.

In some embodiments, some or all state changes in and/or events that occur with respect to records maintained by or accessible to the medical documentation system 100 may be automatically communicated to the CDI system 1502 by the medical documentation system 100 making a call to an API 1706 of the CDI system 1502. For example, when a clinician responds to a clarification request and updates a record using the medical documentation system 100, the medical documentation system 100 may make a call to an API 1706 of the CDI system 1502 to communicate the occurrence of such an event and/or record update to the CDI system 1502. Corresponding patient specific records of the CDI system 1502, e.g., records stored in the database 1508, can thus be updated accordingly to reflect such events and/or record updates. In other embodiments, the medical documentation system 100 may additionally or alternatively automatically push information to the CDI system 1502 using some other suitable technique, such as an HTTP POST request method, so as to ensure that the CDI system 1502 has access to up-to-date audit information from the documentation management system 100. Such updates may, for example, be communicated periodically and/or in response to detected state changes in the data maintained by the medical documentation system 100.

Figure 18:
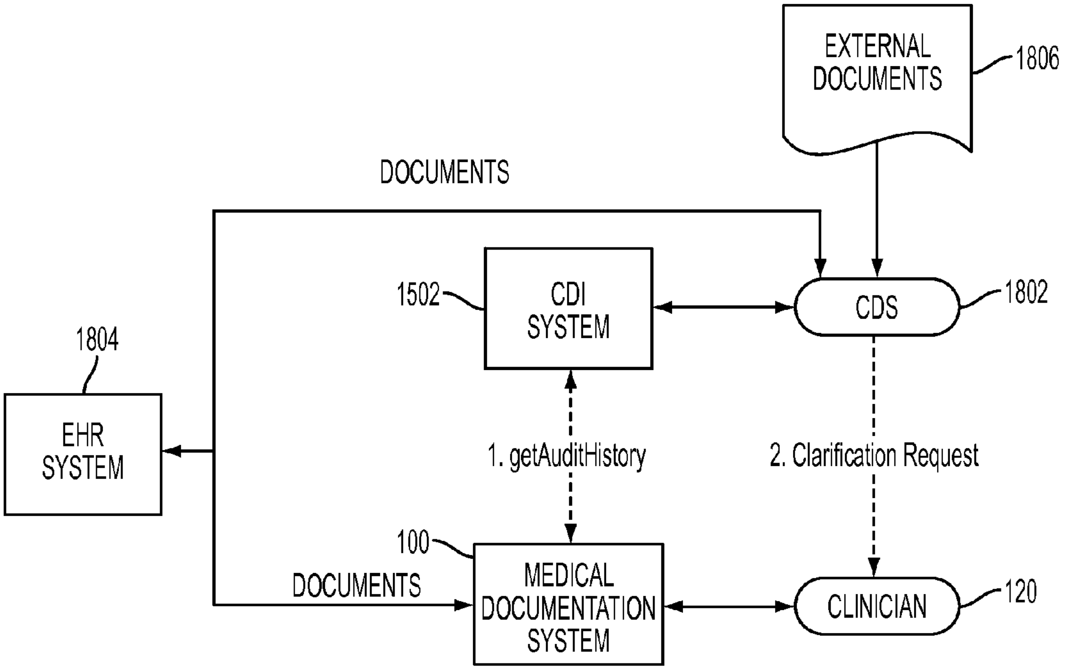
FIGS. 18-20 illustrate examples of workflows in which the interface disclosed herein between the CDI system 1502 and the medical documentation system 1502 may be exploited to achieve certain benefits.
Figure 19:
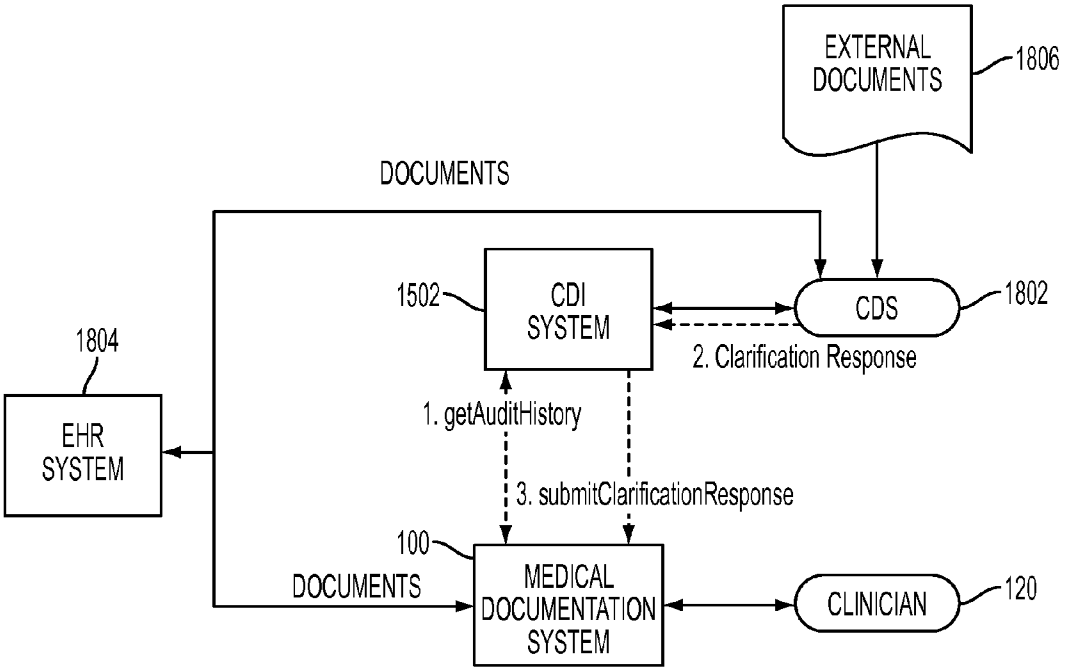
Figure 20:
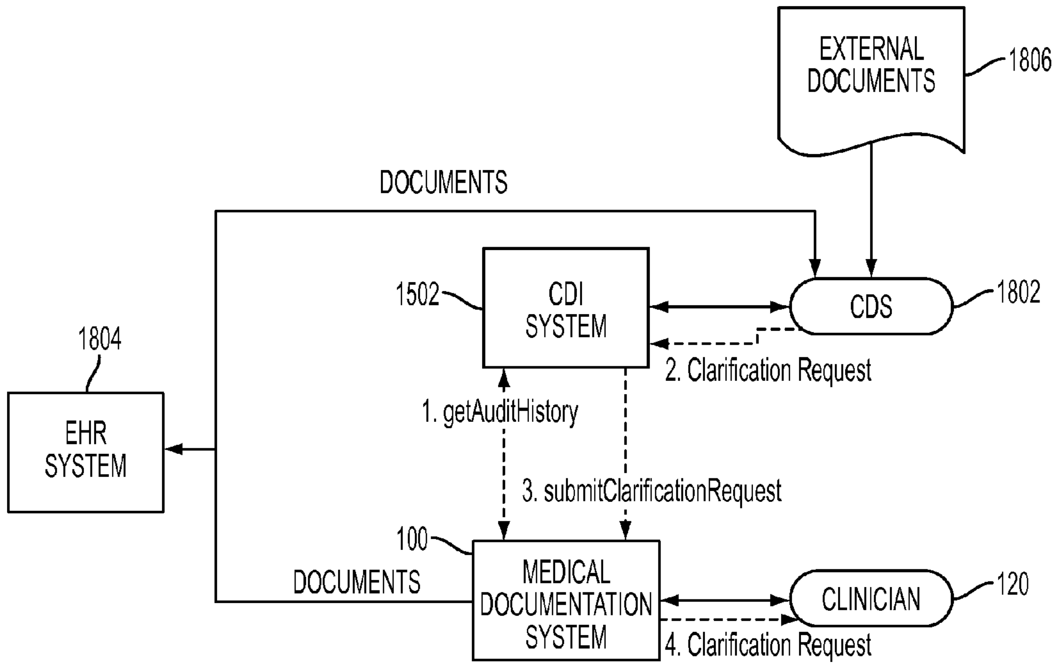

FIGS. 18-20 illustrate examples of workflows in which the interface disclosed herein between the CDI system 1502 and the medical documentation system 100 may be exploited to achieve certain benefits. For each of the illustrated examples, in some embodiments, a CDS 1802 may interact with the CDI system 1502, and a clinician 120 may interact with the medical documentation system 100 in any of the ways and for any of the purposes discussed above. In some embodiments, for example, the CDS 1802 may operate a user interface such as the user interface 1506 shown in FIG. 15, and the clinician may operate a user interface such as the user interface 110 shown in FIG. 1. The clinician 120 may, for example, use the medical documentation system 100 to create and modify one or more medical records for storage in the EHR system 1804, which may, for example, include the patient history records database 160 discussed above in connection with FIG. 1. The CDS 1802 may also access the EHR system 1804 so as to review one or more EHRs for a particular patient as a part of the CDI process. As shown, the CDS may, in some embodiments, also have access to other external documents 1806, which may, for example, include laboratory records, handwritten clinician notes, etc., that are not received by or considered by the medical documentation system 100.

As shown in FIG. 18, in some embodiments, upon the CDS 1802 creating and/or accessing a patient specific record using the CDI system 1502, the CDI system 1502 may make a call to a “getAuditHistory” API on the medical documentation system 100. In response to such an API call, the medical documentation system 100 may transmit a structured data set for the patient to the CDI system 1502. The CDS 1802 is then able to use the transmitted data reflecting some or all of the activity of the medical documentation system 100 relating to the patient for the purpose of formulating new clarification requests to be communicated to the clinician 120 based on the data and/or to refrain from making clarification requests that have already been asked and responded to by the clinician. As shown in FIG. 18, new clarification requests may be communicated from the CDS 1802 to the clinician 120 in any suitable way, including any of the conventional techniques noted above. Alternatively, as discussed below in connection with FIG. 20, new clarification requests may additionally or alternatively be communicated to the clinician via a call to an API 1704 on the medical documentation system 100.

In some embodiments, the structured data set the CDI system 1502 receives pursuant to a call to the “getAuditHistory” API 1704 of the medical documentation system 100 may include one or more clarification requests the medical documentation system 100 had automatically formulated for response by the clinician 120. In some circumstances, the CDS 1802 may have access to sufficient information to respond to such a clarification request without requiring input from the clinician 120. For example, the external documents 1806 (e.g., lab records and/or handwritten notes) may provide sufficient detail to allow the CDS 1802 to formulate a proper response, or the CDS may otherwise have access to sufficient data, e.g., by way of the received structured data set and/or the EHR system, to confidently formulate an accurate response. As shown in FIG. 19, in some embodiments, the CDS 1802 in such circumstances may submit a clarification response to the CDI system 1502, and the CDI system 1502 may, in turn, make a call to a “submitClarificationResponse” API 1504 of the medical documentation system 100. The making of such an API call will effectively input the clarification response into the medical documentation system 100, and will thus obviate the need for the clinician 120 to respond to that particular clarification request.

In some embodiments, the CDS 1802 interfacing with the CDI system 1502 may wish to formulate and communicate new clarification requests to the clinician 120. Such new clarification requests may, for example, be based upon the structured data set for a patient received from the medical documentation system 100, or may additionally or alternatively be based upon one or more EHRs accessed from the EHR system 1804 and/or one or more external documents 1806. In some embodiments, CDI system 1502 may allow such new clarification requests formulated by the CDS 1802 to be communicated to the medical documentation system 100, so as to cause them to be communicated to the clinician 120 in the same manner that clarification requests automatically generated by the medical documentation system 100 are presented to the clinician 120. As shown in FIG. 20, in some embodiments, such new clarification requests may be communicated to the medial documentation system 100 by calling a "submitClarificationRequest" API 1504 on the medical documentation system 100. In some embodiments, in addition to communicating such a clarification request to the clinician 120, the medical documentation system 100 may incorporate the new clarification request into the case model it builds so that the new clarification request and subsequent responses from the clinician 120 can be included in the analysis of the patient visit for all future analyses.

The above-described embodiments of the present invention can be implemented in any of numerous ways. For example, the embodiments may be implemented using to hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above.

In this respect, it should be appreciated that one implementation of embodiments of the present invention comprises at least one computer-readable storage medium (i.e., a tangible, non-transitory computer-readable medium, such as a computer memory, a floppy disk, a compact disk, a magnetic tape, or other tangible, non-transitory computer-readable medium) encoded with a computer program (i.e., a plurality of instructions), which, when executed on one or more processors, performs above-discussed functions of embodiments of the present invention. The computer-readable storage medium can be transportable such that the program stored thereon can be loaded onto any computer resource to implement aspects of the present invention discussed herein. In addition, it should be appreciated that the reference to a computer program which, when executed, performs any of the above-discussed functions, is not limited to an application program running on a host computer. Rather, the term "computer program" is used herein in a generic sense to reference any type of computer code (e.g., software or microcode) that can be employed to program one or more processors to implement above-discussed aspects of the present invention.

The phraseology and terminology used herein is for the purpose of description and should not be regarded as limiting. The use of "including," "comprising," "having," "containing," "involving," and variations thereof, is meant to encompass the items listed thereafter and additional items. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements from each other.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. A method for use with a Clinical Documentation Improvement (CDI) system implemented via at least one first processor and processing medical documentation input at least in part by a clinician, the CDI system configured to communicate with a medical documentation system that also processes the medical documentation and is implemented via at least one second processor, wherein the CDI system includes a user interface by which to present the medical documentation to a CDI specialist and receive from the CDI specialist new information to include in the medical documentation to clarify the medical documentation and to receive from the CDI specialist identification of opportunities for clarification of the medical documentation, the CDI specialist being a human user of the CDI system, and wherein the medical documentation system implemented via the at least one processor analyzes text included in the medical documentation to extract medical facts expressed in the medical documentation and identify opportunities for clarification of the medical documentation, the method comprising:

with the CDI system implemented via the at least one processor, receiving from the medical documentation system a structured data set including at least some information relating to one or more medical facts and including information indicating that the medical documentation system automatically extracted the one or more medical facts from text documenting a patient encounter, wherein the information related to the one or more medical facts comprises a first medical fact and a first confidence score produced by the medical documentation system indicating a confidence of the medical documentation system that the first medical fact was accurately extracted from the text documenting the patient encounter, the information relating to one or more medical facts further comprising at least one clarification request generated by the medical documentation system, the at least one clarification request requesting clarification regarding at least the first medical fact of the one or more medical facts and/or regarding at least a portion of the text documenting the patient encounter;

in response to determining that the first confidence score is below a first threshold, prompting a user of the CDI system regarding the at least one clarification request;

receiving from the user of the CDI system, in response to the prompt regarding the at least one clarification request, at least one input providing clarification regarding the first medical fact and/or the at least the portion of the text documenting the patient encounter; and in response to receiving the at least one input, transmitting a clarification response to the medical documentation system addressing the at least one clarification request, the clarification response comprising an indication of whether to prompt the clinician regarding the at least one clarification request.

2. The method of claim 1, further comprising an act of:

with the CDI system, transmitting a request to the medical documentation system that causes the medical documentation system to transmit the structured data set to the CDI system.

3. The method of claim 2, wherein the request transmitted by the CDI system comprises a call to an API of the medical documentation system.

4. The method of claim 1, wherein transmitting the clarification response comprising the indication of whether to prompt the clinician comprises instructing the medical documentation system not to prompt a clinician regarding the at least one clarification request.

5. The method of claim 1, wherein transmitting the clarification response comprising the indication of whether to prompt the clinician comprises instructing the medical documentation system to prompt a clinician regarding the at least one clarification request.

6. The method of claim 5, wherein instructing the medical documentation system to prompt the clinician comprises identifying an urgency with which the medical documentation system is to prompt the clinician.

7. The method of claim 1, further comprising an act of:

(b) receiving, at the CDI system from a user of the CDI system, a request for clarification of at least a portion of a medical record; and (c) transmitting, with the CDI system, at least one second clarification request to the medical documentation system, the at least one second clarification request identifying the at least the portion of the medical record.

8. The method of claim 1, wherein the at least one first processor and the at least one second processor are the same at least one processor.

9. An apparatus comprising:

at least one processor; and at least one storage medium having encoded thereon executable instructions that, when executed by the at least one processor, cause the at least one processor to carry out a method for use with a Clinical Documentation Improvement (CDI) system implemented via the at least one processor and processing medical documentation input at least in part by a clinician, the CDI system configured to communicate with a medical documentation system that also processes the medical documentation and is implemented via at least one second processor, wherein the CDI system includes a user interface by which to present the medical documentation to a CDI specialist and receive from the CDI specialist new information to include in the medical documentation to clarify the medical documentation and to receive from the CDI specialist identification of opportunities for clarification of the medical documentation, the CDI specialist being a human user of the CDI system, and wherein the medical documentation system implemented via the at least one processor analyzes text included in the medical documentation to extract medical facts expressed in the medical documentation and identify opportunities for clarification of the medical documentation, the method comprising:

with the CDI system, receiving from the medical documentation system a structured data set including at least some information relating to one or more medical facts and including information indicating that the medical documentation system automatically extracted the one or more medical facts from text documenting a patient encounter, wherein the information related to the one or more medical facts comprises a first medical fact and a first confidence score produced by the medical documentation system indicating a confidence of the medical documentation system that the first medical fact was accurately extracted from the text documenting the patient encounter, the information relating to one or more medical facts further comprising at least one clarification request generated by the medical documentation system, the at least one clarification request requesting clarification regarding at least the first medical fact of the one or more medical facts and/or regarding at least a portion of the text documenting the patient encounter;

in response to determining that the first confidence score is below a first threshold, prompting a user of the CDI system regarding the at least one clarification request;

receiving from the user of the CDI system, in response to the prompt regarding the at least one clarification request, at least one input providing clarification regarding the first medical fact and/or the at least the portion of the text documenting the patient encounter; and in response to receiving the at least one input, transmitting a clarification response to the medical documentation system addressing the at least one clarification request, the clarification response comprising an indication of whether to prompt the clinician regarding the at least one clarification request.

10. The CDI system of claim 9, wherein the method comprises, with the CDI system, transmitting a request to the medical documentation system that causes the medical documentation system to transmit the structured data set to the CDI system.

11. The CDI system of claim 10, wherein transmitting the request comprises making a call to an API of the medical documentation system.

12. The CDI system of claim 9, wherein the receiving comprises receiving at least one clarification request generated by the medical documentation system as at least a part of the structured data set.

13. The CDI system of claim 9, wherein the method comprises, with the CDI system, transmitting a clarification request to the medical documentation system concerning the one or more automatically extracted medical facts.

14. At least one non-transitory, computer-readable medium having a plurality of instructions encoded thereon which, when executed by at least one processor, cause the at least one processor to carry out a method for use with a Clinical Documentation Improvement (CDI) system implemented via the at least one processor and processing medical documentation input at least in part by a clinician, the CDI system configured to communicate with a medical documentation system that also processes the medical documentation and is implemented via at least one second processor, wherein the CDI system includes a user interface by which to present the medical documentation to a CDI specialist and receive from the CDI specialist new information to include in the medical documentation to clarify the medical documentation and to receive from the CDI specialist identification of opportunities for clarification of the medical documentation, the CDI specialist being a human user of the CDI system, and wherein the medical documentation system implemented via the at least one processor analyzes text included in the medical documentation to extract medical facts expressed in the medical documentation and identify opportunities for clarification of the medical documentation, the method comprising:

with the CDI system, receiving from the medical documentation system a structured data set including at least some information relating to one or more medical facts and including information indicating that the medical documentation system automatically extracted the one or more medical facts from text documenting a patient encounter, wherein the information related to the one or more medical facts comprises a first medical fact and a first confidence score produced by the medical documentation system indicating a confidence of the medical documentation system that the first medical fact was accurately extracted from the text documenting the patient encounter, the information relating to one or more medical facts further comprising at least one clarification request generated by the medical documentation system, the at least one clarification request requesting clarification regarding at least the first medical fact of the one or more medical facts and/or regarding at least a portion of the text documenting the patient encounter;

in response to determining that the first confidence score is below a first threshold, prompting a user of the CDI system regarding the at least one clarification request;

receiving from the user of the CDI system, in response to the prompt regarding the at least one clarification request, at least one input providing clarification regarding the first medical fact and/or the at least the portion of the text documenting the patient encounter; and in response to receiving the at least one input, transmitting a clarification response to the medical documentation system addressing the at least one clarification request, the clarification response comprising an indication of whether to prompt the clinician regarding the at least one clarification request.

15. The computer-readable medium of claim 14, wherein the method further comprises, with the CDI system, transmitting a request to the medical documentation system that causes the medical documentation system to transmit the structured data set to the CDI system.

16. The computer-readable medium claim 15, wherein transmitting the request comprises making a call to an API of the medical documentation system.

17. The computer-readable medium of claim 14, wherein the method further comprises, with the CDI system, transmitting a clarification request to the medical documentation system concerning the one or more automatically extracted medical facts.

* * * * *